(12) United States Patent
Frank et al.

(10) Patent No.: US 9,955,902 B2
(45) Date of Patent: May 1, 2018

(54) NOTIFYING A USER ABOUT A CAUSE OF EMOTIONAL IMBALANCE

(71) Applicant: Affectomatics Ltd., Kiryat Tivon (IL)

(72) Inventors: Ari M Frank, Haifa (IL); Gil Thieberger, Kiryat Tivon (IL)

(73) Assignee: Affectomatics Ltd., Kiryat Tivon (IL)

( * ) Notice: Subject to any disclaimer, the term of this patent is extended or adjusted under 35 U.S.C. 154(b) by 0 days. days.

(21) Appl. No.: 15/193,091

(22) Filed: Jun. 26, 2016

(65) Prior Publication Data

US 2016/0302711 A1 Oct. 20, 2016

Related U.S. Application Data

(63) Continuation-in-part of application No. 15/184,401, filed on Jun. 16, 2016, which is a continuation-in-part of application No. 15/010,412, filed on Jan. 29, 2016.

(60) Provisional application No. 62/109,456, filed on Jan. 29, 2015, provisional application No. 62/185,304, filed on Jun. 26, 2015.

(51) Int. Cl.
| | |
|---|---|
| G08B 23/00 | (2006.01) |
| A61B 5/16 | (2006.01) |
| A61B 5/00 | (2006.01) |
| G06F 21/62 | (2013.01) |
| G06F 17/30 | (2006.01) |

(52) U.S. Cl.
CPC ........... *A61B 5/165* (2013.01); *A61B 5/7267* (2013.01); *A61B 5/7275* (2013.01); *A61B 5/7282* (2013.01); *A61B 5/746* (2013.01); *G06F 17/3053* (2013.01); *G06F 21/6245* (2013.01)

(58) Field of Classification Search
CPC ................................................ G06F 2203/011
See application file for complete search history.

(56) References Cited

U.S. PATENT DOCUMENTS

| | | |
|---|---|---|
| 8,676,230 B2 | 3/2014 | Alexander et al. |
| 8,764,652 B2 | 7/2014 | Lee et al. |
| 9,165,216 B2 | 10/2015 | Angell et al. |
| 2007/0048707 A1 | 3/2007 | Caamano et al. |
| 2007/0150916 A1 | 6/2007 | Begole et al. |
| 2008/0221401 A1 | 9/2008 | Derchak et al. |

(Continued)

OTHER PUBLICATIONS

Banaee, et al. "Data mining for wearable sensors in health monitoring systems: a review of recent trends and challenges." Sensors 13.12 (2013): 17472-17500.

(Continued)

*Primary Examiner* — Omeed Alizada
(74) *Attorney, Agent, or Firm* — Active Knowledge Ltd.

(57) ABSTRACT

Some aspects of this disclosure include systems, methods, and/or computer programs that may be used to notify a user about a cause of emotional imbalance. Some embodiments described herein involve determining when a user is in a state of emotional imbalance based on a measurement of affective response of the user, which is taken with a sensor. Factors characterizing an event to which the measurement corresponds are examined in order to select a certain factor that, based on a model of the user, has an effect on the user that is congruous with the measurement of affective response. The user is notified about the certain factor in order to make the user more aware of the certain factor and its effect on the user.

21 Claims, 6 Drawing Sheets

(56) References Cited

U.S. PATENT DOCUMENTS

| | | | |
|---|---|---|---|
| 2008/0319272 A1* | 12/2008 | Patangay | A61B 5/0002 600/300 |
| 2011/0046502 A1 | 2/2011 | Pradeep et al. | |
| 2011/0106750 A1 | 5/2011 | Pradeep et al. | |
| 2011/0004110 A1 | 6/2011 | Shusterman | |
| 2012/0290266 A1 | 11/2012 | Jain et al. | |
| 2014/0200463 A1 | 7/2014 | el Kaliouby et al. | |
| 2014/0221858 A1 | 8/2014 | Myr | |
| 2014/0280529 A1 | 9/2014 | Davis et al. | |
| 2014/0324749 A1* | 10/2014 | Peters | G09B 7/04 706/46 |
| 2014/0350349 A1 | 11/2014 | Geurts et al. | |
| 2014/0366049 A1* | 12/2014 | Lehtiniemi | H04N 21/44218 725/12 |
| 2015/0142553 A1 | 5/2015 | Kodra et al. | |
| 2015/0289800 A1 | 10/2015 | Pacione et al. | |
| 2015/0313530 A1 | 11/2015 | Kodra et al. | |

OTHER PUBLICATIONS

Conati, Cristina, and Heather Maclaren. "Empirically building and evaluating a probabilistic model of user affect." *User Modeling and User-Adapted Interaction* 19.3 (2009): 267-303.

Ertin, Emre, et al. "AutoSense: unobtrusively wearable sensor suite for inferring the onset, causality, and consequences of stress in the field." *Proceedings of the 9th ACM Conference on Embedded Networked Sensor Systems*. ACM, 2011.

Ohme, Rafal, et al. "Analysis of neurophysiological reactions to advertising stimuli by means of EEG and galvanic skin response measures." *Journal of Neuroscience, Psychology, and Economics* 2.1 (2009): 21.

Scheirer, Jocelyn, et al. "Frustrating the user on purpose: a step toward building an affective computer." *Interacting with computers* 14.2 (2002): 93-118.

Sherman, Ryne A., Christopher S. Nave, and David C. Funder. "Situational similarity and personality predict behavioral consistency." *Journal of personality and social psychology* 99.2 (2010): 330.

Soleymani, Mohammad, Maja Pantic, and Thierry Pun. "Multimodal emotion recognition in response to videos." *IEEE transactions on affective computing* 3.2 (2012): 211-223.

Sun, Feng-Tso, et al. "Activity-aware mental stress detection using physiological sensors." *International Conference on Mobile Computing, Applications, and Services*. Springer, Berlin, Heidelberg, 2010.

* cited by examiner

NOTIFYING A USER ABOUT A CAUSE OF EMOTIONAL IMBALANCE

CROSS-REFERENCE TO RELATED APPLICATIONS

This Application is a Continuation-In-Part of U.S. application Ser. No. 15/184,401, filed Jun. 16, 2016, which is incorporated herein by reference in its entirety. U.S. application Ser. No. 15/184,401 is a Continuation-In-Part of U.S. application Ser. No. 15/010,412, filed Jan. 29, 2016, which claims the benefit of U.S. Provisional Patent Application Ser. No. 62/109,456, filed Jan. 29, 2015. This Application also claims the benefit of U.S. Provisional Patent Application Ser. No. 62/185,304, filed Jun. 26, 2015.

BACKGROUND

In order to help people manage their day-to-day lives and improve their emotional health, coaches and phycologists often analyze events people have in order to help determine causes that may lead to emotional imbalance and/or causes that may contribute to emotional balance. Being aware of these causes can help the people cope with challenging events in their lives and help them make better choices to benefit their emotional wellbeing.

However, analysis by coaches and psychologists is typically done after the fact, possibly after much time has elapsed since the relevant events. This analysis also relies on the recollection of the relevant events by the people, which may be incomplete and/or inaccurate.

Thus, there is a need for a way to provide people with analysis of events in order to increase their awareness of causes contributing to emotional balance or imbalance in their day-to-day lives, which may be provided in a timely and accurate fashion.

SUMMARY

The pervasiveness of various types of wearables with sensors enables collection of many measurements of affective response of users on a daily basis, in real world scenarios, and corresponding to events involving various types of experiences. This abundance of data may be utilized for various applications, such as learning models of the users, which may be utilized to better understand the users (such as understating their biases). Additionally, various sensors and data sources may be utilized to determine what factors characterize the various events the users are involved in. Such data is utilized in some of the embodiments described herein in order to determine causes (factors) that may contribute to emotional balance or to emotional imbalance of the users.

One aspect of this disclosure involves systems that are configured to notify a user about a cause of a certain emotional state. For example, a system described herein may notify the user about a certain factor that can lead the user to a state of emotional imbalance. In another example, a system described herein may notify the user about a certain factor that can lead the user to a state of emotional balance.

In some embodiments, a system described above may include the following computer-executable modules: an emotional state analyzer module, an event analyzer module, and an awareness module. The emotional state analyzer module is configured to receive a measurement of affective response of the user, which corresponds to an event, and to make a determination of whether the measurement indicates a state of emotional state of the user (e.g., a state of emotional balance or a state of emotional imbalance). Optionally, the measurement is taken with a sensor, coupled to the user, and the measurement comprises at least one of the following values: a physiological signal of the user, a behavioral cue of the user. The event analyzer module is configured to receive factors characterizing the event and to select a certain factor that, based on a model of the user, has an effect on the user that is congruous with the measurement of affective response of the user. The awareness module is configured to notify the user about the certain factor that characterizes the event, responsive to a determination that the measurement indicates the certain emotional state (e.g., emotional imbalance of the user or emotional balance of the user).

The certain factor that the user is made aware of may be any of the factors that may be relevant to an event, such as a factor that is related to the user, a factor that is related to an experience the user has as part of the event, and/or a factor relevant to the instantiation of the event (e.g., a factor related to the conditions in which the user had the experience). For example, the certain factor may represent having a certain person (other than the user) be part of the experience, the certain factor may represent a certain activity that was part of the event and/or a certain characteristic of the event, the certain factor may represent the fact that the event involves being at a certain location, and/or the certain factor may represent a certain situation the user is in during the event (e.g., tiredness, hunger, being late, etc.).

The experience corresponding to the event may be any of the various experiences described in this disclosure. In one embodiment, having the experience may involve doing at least one of the following: spending time at a certain location, consuming certain digital content, having a social interaction with a certain entity in the physical world, having a social interaction with a certain entity in a virtual world, viewing a certain live performance, performing a certain exercise, traveling a certain route, and consuming a certain product.

Emotional imbalance is typically considered herein to be a negative emotional state of the user. Optionally, when the user is in the state of emotional imbalance, a measurement (and/or a prediction) of affective response of the user indicates that an extent to which the user felt a certain emotion reaches a threshold (where the certain emotion is at least one of the following emotions: anger, contempt, disgust, distress, and fear). Optionally, when the user is in the state of emotional imbalance, a measurement (and/or a prediction) of affective response of the user indicates that a level of stress felt by the user reaches a threshold.

Emotional balance is typically considered herein to be a positive emotional state of the user. Optionally, when the user is in the state of emotional balance, a measurement (and/or a prediction) of affective response corresponding to the event indicates that an extent to which the user felt a certain emotion reaches a threshold (where the certain emotion is at least one of the following emotions: happiness, and contentment). Optionally, when the user is in the state of emotional balance, a measurement (and/or a prediction) of affective response corresponding to the event indicates that an extent to which the user felt a certain emotion does not reach a threshold (where the certain emotion is at least one of the following emotions: anger, contempt, disgust, distress, and fear). Optionally, when the user is in the state of emotional balance, a measurement (and/or a prediction) of affective response corresponding to the event indicates that a level of stress felt by the user does not reach a threshold.

Another aspect of this disclosure involves a method for notifying a user about a cause of a certain emotional state (e.g., the certain emotional state may correspond to emotional imbalance or emotional balance). In some embodiments, such a method includes at least the following steps: receiving, by a system comprising a processor and memory, a measurement of affective response of the user, which corresponds to an event; determining whether the measurement indicates the certain emotional state of the user; receiving factors that characterize the event; selecting a certain factor that characterizes the event which, based on a model of the user, has an effect on the user that is congruous with the measurement; and responsive to a determination that the measurement indicates the certain emotional state, notifying the user about the certain factor.

Yet another aspect of this disclosure involves a computer-readable medium that stores instructions for implementing the method described above. Optionally, the computer-readable medium is a non-transitory computer-readable medium. In response to execution by a system including a processor and memory, the instructions cause the system to perform operations that are part of the method.

Selecting the certain factor mentioned above based on a measurement of affective response corresponding to an event requires that the user be involved in the event (i.e., the user has the experience corresponding to the event). However, given a model of the user, in some embodiment, the affective response corresponding to the event may be predicted. Using a predicted affective response instead of a measurement of affective response may, in some embodiments, have advantages in terms of being able to help identify future events to participate in or avoid, and making the user aware of factors in events involving experiences the user has yet to have.

One aspect of this disclosure involves systems that are configured to utilize a predicted affective response to notify a user about a cause of a certain emotional state. For example, a system described herein may notify the user about a certain factor that can lead the user to a state of emotional imbalance. In another example, a system described herein may notify the user about a certain factor that can lead the user to a state of emotional balance.

In some embodiments, a system described above may include the following computer-executable modules: a feature generator, an Emotional Response Predictor (ERP), an emotional state analyzer module, and an awareness module. The feature generator configured to: receive a description indicative of factors characterizing an event that involves the user having an experience, and to utilize the description to generate feature values. Optionally, each of the factors corresponds to at least one of the following: the user, the experience, and the instantiation of the event. The ERP is configured to utilize a first model of the user to predict, based on the feature values, a predicted affective response corresponding to the event. The emotional state analyzer module is configured to receive the predicted affective response of the user and to determine whether the user is expected to be in a certain emotional state (e.g., a state corresponding to emotional imbalance or a state corresponding to emotional balance). The event analyzer module is configured to select a certain factor, from among the factors, that, based on a second model of the user, has an effect on the user that is congruous with the predicted affective response of the user. Optionally, the first model of the user and the second model of the user are the same. The awareness module is configured to notify the user about the certain factor, responsive to a determination that the predicted affective response indicates the state of emotional imbalance.

Another aspect of this disclosure involves a method for utilizing a predicted affective response to notify a user about a cause of a certain emotional state (e.g., the certain emotional state may correspond to emotional imbalance or emotional balance). In some embodiments, such a method includes at least the following steps: receiving, by a system comprising a processor and memory, a description indicative of factors characterizing an event that involves the user having an experience (where each of the factors corresponds to at least one of the following: the user, the experience, and the instantiation of the event); computing, from an input based on the description and utilizing a first model of the user, a predicted affective response corresponding to the event; determining whether predicted affective response corresponding to the event indicates the certain emotional state; selecting a certain factor from among the factors (where based on a second model of the user, the certain factor has an effect on the user that is congruous with the predicted affective response); and responsive to determining that the predicted affective response indicates the certain emotional state, notifying the user about the certain factor.

Yet another aspect of this disclosure involves a computer-readable medium that stores instructions for implementing the method described above. Optionally, the computer-readable medium is a non-transitory computer-readable medium. In response to execution by a system including a processor and memory, the instructions cause the system to perform operations that are part of the method.

BRIEF DESCRIPTION OF THE DRAWINGS

The embodiments are herein described, by way of example only, with reference to the accompanying drawings. In the drawings.

DETAILED DESCRIPTION

Figure 1:
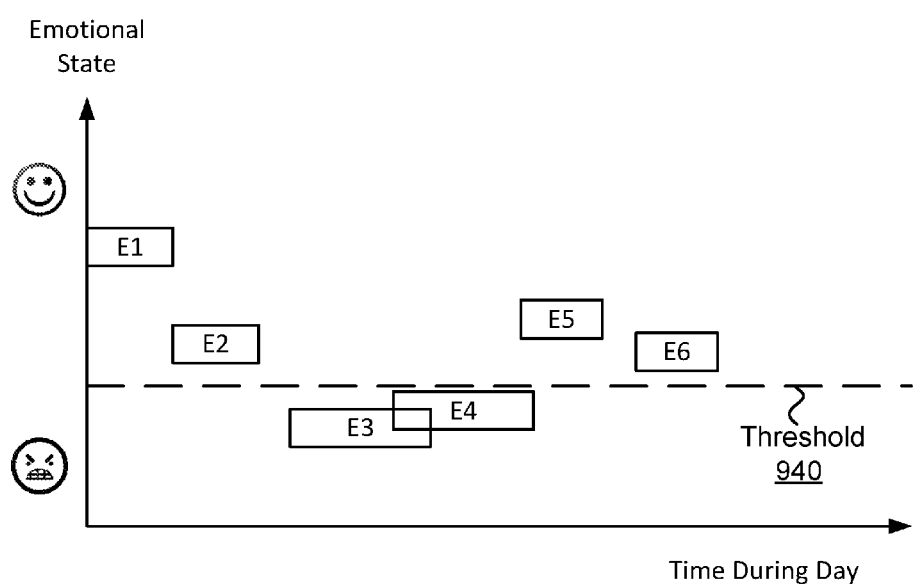
FIG. 1 illustrates an example of emotional states a user was in during a certain day at times corresponding to various events.

A measurement of affective response of a user is obtained by measuring a physiological signal of the user and/or a behavioral cue of the user. A measurement of affective response may include one or more raw values and/or processed values (e.g., resulting from filtration, calibration, and/or feature extraction). Measuring affective response may be done utilizing various existing, and/or yet to be invented, measurement devices such as sensors. Optionally, any device that takes a measurement of a physiological signal of a user and/or of a behavioral cue of a user, may be considered a sensor. A sensor may be coupled to the body of a user in various ways. For example, a sensor may be a device that is implanted in the user's body, attached to the user's body, embedded in an item carried and/or worn by the user (e.g., a sensor may be embedded in a smartphone, smartwatch, and/or clothing), and/or remote from the user (e.g., a camera taking images of the user).

Herein, "affect" and "affective response" refer to physiological and/or behavioral manifestation of an entity's emotional state. The manifestation of an entity's emotional state may be referred to herein as an "emotional response", and may be used interchangeably with the term "affective response". Affective response typically refers to values obtained from measurements and/or observations of an entity, while emotional states are typically predicted from models and/or reported by the entity feeling the emotions. For example, according to how terms are typically used herein, one might say that a person's emotional state may be determined based on measurements of the person's affective response. In addition, the terms "state" and "response", when used in phrases such as "emotional state" or "emotional response", may be used herein interchangeably. However, in the way the terms are typically used, the term "state" is used to designate a condition which a user is in, and the term "response" is used to describe an expression of the user due to the condition the user is in, and/or due to a change in the condition the user is in.

It is to be noted that as used herein in this disclosure, a "measurement of affective response" may comprise one or more values describing a physiological signal and/or behavioral cue of a user which were obtained utilizing a sensor. Optionally, this data may also be referred to as a "raw" measurement of affective response. Thus, for example, a measurement of affective response may be represented by any type of value returned by a sensor, such as a heart rate, a brainwave pattern, an image of a facial expression, etc.

Additionally, as used herein a "measurement of affective response" may refer to a product of processing of the one or more values describing a physiological signal and/or behavioral cue of a user (i.e., a product of the processing of the raw measurements data). The processing of the one or more values may involve one or more of the following operations: normalization, filtering, feature extraction, image processing, compression, encryption, and/or any other techniques described further in the disclosure and/or that are known in the art and may be applied to measurement data. Optionally, a measurement of affective response may be a value that describes an extent and/or quality of an affective response (e.g., a value indicating positive or negative affective response such as a level of happiness on a scale of 1 to 10, and/or any other value that may be derived from processing of the one or more values).

It is to be noted that since both raw data and processed data may be considered measurements of affective response, it is possible to derive a measurement of affective response (e.g., a result of processing raw measurement data) from another measurement of affective response (e.g., a raw value obtained from a sensor). Similarly, in some embodiments, a measurement of affective response may be derived from multiple measurements of affective response. For example, the measurement may be a result of processing of the multiple measurements.

In some embodiments, a measurement of affective response may be referred to as an "affective value" which, as used in this disclosure, is a value generated utilizing a module, function, estimator, and/or predictor based on an input comprising the one or more values describing a physiological signal and/or behavioral cue of a user, which are either in a raw or processed form, as described above. As such, in some embodiments, an affective value may be a value representing one or more measurements of affective response. Optionally, an affective value represents multiple measurements of affective response of a user taken over a period of time. An affective value may represent how the user felt while utilizing a product (e.g., based on multiple measurements taken over a period of an hour while using the product), or how the user felt during a vacation (e.g., the affective value is based on multiple measurements of affective response of the user taken over a week-long period during which the user was on vacation).

In some embodiments, measurements of affective response of a user are primarily unsolicited, i.e., the user is not explicitly requested to initiate and/or participate in the process of measuring. Thus, measurements of affective response of a user may be considered passive in the sense the user may not be notified when the measurements are taken, and/or the user may not be aware that measurements are being taken.

An experience, as used herein, involves something that happens to a user and/or that the user does, which may affect the physiological and/or emotional state of the user in a manner that may be detected by measuring the affective response of the user. Optionally, experiences may belong to different groups and/or types, such as being at a location, consuming certain content, having a social interaction (e.g., in the physical world or a virtual world), exercising, traveling a certain route, consuming a substance, and/or utilizing a product. In some embodiments, experiences may involve activity in the physical world (e.g., spending time at a hotel) and/or activity in virtual environments (e.g., spending time in a virtual world or in a virtual chat room). In some embodiments, an experience is something a user actively chooses and is aware of; for example, the user chooses to take a vacation. While in other embodiments, an experience may be something that happens to the user, of which the user may not be aware. For example, a user may consume food that unbeknownst to the user contains a certain additive; this example may correspond to an experience of consuming the additive even if the user is not aware that he/she is consuming it. A user may have the same experience multiple times during different periods. For example, the experience of being at school may happen to certain users every weekday, except for holidays. Each time a user has an experience, this may be considered an "event". Each event has a corresponding experience and a corresponding user (who had the corresponding experience). Additionally, an event may be referred to as being an "instantiation" of an experience and the time during which an instantiation of an event takes place, may be referred to herein as the "instantiation period" of the event. That is, the instantiation period of an event is the period of time during which the user corresponding to the event had the experience corresponding to the event. Optionally, an event may have a corresponding measurement of affective response, which is a measurement of the corresponding user to having the corresponding experience (during the instantiation of the event or shortly after it).

In some embodiments, an event may have a corresponding measurement of affective response, which is a measurement of the user corresponding to the event, to having the experience corresponding to the event. The measurement corresponding to an event is taken during a period corresponding to the event; for example, during the time the user corresponding to the event had the experience corresponding to the event, or shortly after that. Optionally, a measurement corresponding to an event reflects the affective response corresponding to the event, which is the affective response of the user corresponding to the event to having the experience corresponding to the event. Thus, a measurement of affective response corresponding to an event typically comprises, and/or is based on, one or more values measured during the instantiation period of the event and/or shortly after it.

Determining whether different events correspond to the same experience or to different experiences may depend on the embodiment that is examined. For example, in one embodiment, an event involving a user that rides a bike in the city is considered to correspond to a different experience than an event in which a user goes mountain biking. However, in another embodiment, these two events may be considered to correspond to the same experience (e.g., the experience of riding a bike). Similarly, in some embodiments, there is a reference to a type of an experience. In this case too, determining the type of an experience may depend on the embodiment. For example, in one embodiment, going to a movie and riding a bike in the park are considered to be different types of experiences (e.g., these may be considered experiences of the types "consuming content" and "exercising", respectively). However, in another embodiment both experiences may be considered to be of the type "recreational activity". Further details regarding experiences and events may be found further below in this disclosure and in section 3 (Experiences) in the patent application U.S. Ser. No. 15/184,401.

An event may be characterized according to various aspects of the event called "factors". As typically used herein, a factor of an event corresponds to an aspect of an event. The aspect may involve the user corresponding to the event, such as a situation of the user (e.g., that the user is tired, late, or hungry). Additionally or alternatively, the aspect may involve the experience corresponding to the event (e.g., the experience is a social game, involves clowns, or it involves eating spicy food). Additionally or alternatively, the aspect may involve how the experience took place, such as a detail involving the instantiation of the event. Factors are typically objective values, often representing essentially the same thing for different users. For example, factors may be derived from analyzing descriptions of events, and as such can represent the same thing for events involving different users. For example, a factor corresponding to "an experience that takes place outdoors" will typically mean the same thing for different users and even different experiences.

In an event involving a user having an experience, an affective response of the user may be influenced by the various factors that characterize the event. The quality of such influences are referred to herein as biases (or simply bias). A bias, as used herein, is a tendency, attitude and/or inclination, which may influence the affective response a user has to an experience. Consequently, a bias may be viewed as responsible for a certain portion of the affective response to the experience; a bias may also be viewed as a certain change to the value of a measurement of affective response of a user to the experience, which would have not occurred had the bias not existed. When considering a bias effecting affective response corresponding to an event (i.e., the affective response of the user corresponding to the event to the experience corresponding to the event), the bias may be viewed as being caused by a reaction of a user to one or more factors characterizing the event.

As opposed to factors of events, which are often objective values, as used herein, bias represents how a user responds to a factor (i.e., bias represents the impact of the factor on affective response), and is therefore typically subjective and may vary between users. For example, a first user may like spicy food, while a second user does not. First and second events involving the first and second users may both be characterized by a factor corresponding to eating food that is spicy. However, how the users react (their individual bias) may be completely different; for the first user, the user's bias increases enjoyment from eating the spicy food, while for the second user, the user's bias decreases enjoyment from eating the spicy food.

A bias may be viewed as having an impact on the value of a measurement of affective response corresponding to an event involving a user who has an experience. This may be due to an incidence in the event of a factor corresponding to the bias, which the user reacts to, and which causes the change in affective response compared to the affective response the user would have had to the experience, had there been no incidence of the factor (or were the factor less dominant in the event).

The effects of biases may be considered, in some embodiments, in the same terms as measurements of affective response (e.g., by expressing bias as the expected change to values of measured affective response). Thus, biases may be represented using units corresponding to values of physiological signals, behavioral cures, and/or emotional responses. Furthermore, biases may be expressed as one or more of the various types of affective values discussed in this disclosure. Though often herein bias is represented as a scalar value (e.g., a change to star rating or a change in happiness or satisfaction expressed on a scale from 1 to 10), similar to affective values, bias may represent a change to a multidimensional value (e.g., a vector representing change to an emotional response expressed in a multidimensional space such as the space of Valence/Arousal/Power). Additionally, herein, biases will often be referred to as being positive or negative. This typically refers to a change in affective response which is usually perceived as being better or worse from the standpoint of the user who is affected by the bias. So for example, a positive bias may lead to an increase in a star rating if measurements are expressed as star ratings for which a higher value means a better experience was had. A negative bias may correspond to a vector in a direction of sadness and/or anxiety when measurements of affective response are represented as vectors in a multidimensional space, in which different regions of the space correspond to different emotions the user may feel.

In embodiments, described herein biases and/or the effect thereof on affective response may be modeled in various ways, as described below. A more comprehensive discussion of biases and models of biases is given further below in this disclosure and in section 13 (Bias Values) and section 14 (Bias Functions) in the patent application U.S. Ser. No. 15/184,401.

In some embodiments, biases may be represented by values (referred to herein as "bias values"), which quantify the influence of factors of an event on the affective response (e.g., a measurement corresponding to the event). For example, bias values may be random variables (e.g., the bias values may be represented via parameters of distributions). In another example, bias values may be scalar values or multidimensional values such as vectors. As typically used herein, a bias value quantifies the effect a certain factor of an event has on the affective response of the user. In some embodiments, the bias values may be determined from models generated using training data comprising samples describing factors of events and labels derived from measurements of affective response corresponding to the events.

In other embodiments, biases may be represented via a function (referred to herein as a "bias function"), which may optionally involve a predictor of affective response, such as Emotional Response Predictor (ERP) 731. In this approach, the bias function receives as input feature values that represent factors of an event. Optionally, the factors may describe aspects of the user corresponding to an event, the experience corresponding to the event, and/or aspects of the instantiation of the event. Given an input comprising the factors (or based on the factors), the predictor generates a prediction of affective response for the user. In this approach, a user's biases (i.e., the user's "bias function") may come to play by the way the values of factors influence the value of the predicted affective response.

During the day-to-day life of a user, there may be many events, each involving the user having an experience from among various types of experiences described in this disclosure, which may range from the unique and exciting, such as "once in a lifetime" trips, to the routine and mundane, such as brushing one's teeth. These events can influence how the user feels (the user's affective response), which may also be referred to herein as the user's emotional response and/or as the user's emotional state. How each event affects the user may depend of various factors. In one example, one or more of the various factors may correspond to the user (e.g., a situation the user may be in at the time). In another example, the one or more of the various factors may correspond to the experience (e.g., the type of experience, whether or not it involves physical activity, etc.). In yet another example, the one or more of the various factors may correspond to the instantiation of the event (e.g., how long the experience took, the location at which the user has the experience, etc.). Additional details regarding what factors may influence affective response are given further below in this disclosure.

Determining the user's affective response, which corresponds to an event in which the user has an experience, may be done in various ways. For example, the affective response may be determined based on a measurement of affective response corresponding to the event. Such a measurement may be taken with a sensor coupled to the user and may represent a value of a physiological signal of the user and/or a value of a behavioral cue of the user. Additionally or alternatively, the affective response may be predicted based on factors characterizing the event. For example, an Emotional Response Predictor (ERP) such as ERP 731 may be utilized for this purpose (as described in more detail below).

A user's affective response corresponding to an event may be considered, in some embodiments, to represent certain emotional states. For example, the emotional state may be categorized as predominantly experiencing a certain emotion (e.g., a state of happiness or anger). In another example, the emotional state may be categorized as being in a certain emotional state that is considered to be balanced or not (i.e., as state of "emotional balance" or a state of "emotional imbalance").

In some embodiments, when a measurement of affective response of a user has a value that reaches a certain threshold and/or the value is in a certain range, the user is considered to be in a state of emotional imbalance. For example, a heart rate that reaches a certain value and/or breathing rate that reaches a certain value may be considered to correspond to a state of emotional imbalance. In some embodiments, when an emotional state of a user is represented by a value that reaches a certain threshold and/or is in a certain range, the user may be considered to be in a state of emotional imbalance. For example, when the user is feeling at least a certain level of anger, the user may be considered to be in a state of emotional imbalance. In another example, certain regions of a high-dimensional space that is used to represent emotions, such as the circumplex of emotions, may be considered to represent states of emotional imbalance.

Herein, a certain value, such as a value of a physiological signal or an extent of an emotion, "reaches" a threshold if the certain value equals or exceeds the value corresponding to the threshold (i.e., the value the threshold represents). For example, if a threshold represents an anger level of 7 (on a scale of 1 to 10, with 10 being the highest), then the values 7, 7.5, and 9 are all considered to reach the threshold, while lower values such as 6.5 is considered not to reach the threshold. Furthermore, in some contexts, a threshold may be reached from the other direction. For example, a threshold corresponding to being at rest may be a heart rate 40 beats per minute; in this example, reaching the threshold means having a heart rate that is at most 40 beats per minute.

In some embodiments, when a user is not considered to be in a state of emotional imbalance the user is considered to be in a state of emotional balance. Additionally or alternatively, when a measurement of affective response of a user has a value that reaches a certain threshold and/or the value is in a certain range, the user is considered to be in a state of emotional balance. For example, a heart rate that is below a certain value (e.g., 100 beats per minute) may be considered indicative of a state of emotional balance. Additionally or alternatively, when an emotional state of a user is represented by a value that reaches a certain threshold and/or is in a certain range, the user may be considered to be in a state of emotional balance. For example, when the user is feeling at least a certain level of happiness, the user may be considered to be in a state of emotional imbalance. In another example, certain regions of a high-dimensional space that is used to represent emotions, such as the circumplex of emotions, may be considered to represent states of emotional balance (these regions will typically be separated from regions that represent emotional imbalance).

FIG. 1 illustrates an example of emotional states a user was in during a certain day at times corresponding to various events. The events are represented by the rectangles denoted E1 to E6; the heights at which the rectangles are located represent emotional states of the user at a times corresponding to the events. For example, the emotional states may be determined based on measurements of affective response of the user, which correspond to the events (e.g., the measurements are taken with a sensor coupled to the user during the instantiation of the events or shortly thereafter). In the figure, the height at which a rectangle is located represents the emotional state in terms of the extent of feeling a certain emotion such as happiness (at the higher levels) or anger (at the lower levels). The dash line represents a threshold 940; when the user is in a state represented by a lower value than the threshold 940, the user may be considered to be in a state of emotional imbalance (e.g., in a state involving an excess of anger or rage). For example, in FIG. 1, the emotional states corresponding to the events E3 and E4 correspond to a state of imbalance since their representation is below the threshold.

Various embodiments described herein involve a model of the user that may be utilized in order to analyze the affective response corresponding to an event in which the user is involved. This affective response of the user to having the experience corresponding to the event may be measured (e.g., utilizing a sensor such as sensor 102) or predicted (e.g., utilizing the ERP 731). In some embodiments, the analysis may involve determining the effect certain factors that characterize the event had on the affective response of the user. Examples of such factors include the type of experience corresponding to the event, who the user had the experience with, and the situation of the user while having the experience (e.g., hunger, tiredness, restfulness, preoccupation, etc.).

Being made aware of the effect certain factors may have on a user's affective response can be beneficial to the user. In particular, this information may be useful in cases where events bring the user to a state of emotional imbalance or help the user be in emotional balance. Awareness of how certain factor influence a user can help a user better cope with events in order to maintain a desirable emotional state. Furthermore, such awareness can also be utilized to make better choices regarding future events and even change scheduled plans to avoid an undesirable emotional state. Various embodiments described herein involve system, methods, and computer programs that may be utilized to notify a user about factors that lead to certain emotional states of the user.

In some embodiments, a measurement of affective response of a user, which corresponds to an event involving an experience the user had or is still having at the time, is utilized in order to make the user aware of some effects factors that characterize the event have on the user. In some embodiments, the user is made aware of a certain factor that has an effect on the user that is congruous with the measurement of affective response of the user. Optionally, if the user is determined to be in a state of emotional imbalance, the certain factor may be viewed as contributing to the imbalance. Optionally, if the user is determined to be in a state of emotional balance, the certain factor may be credited with assisting the user to be in this state.

Figure 2:
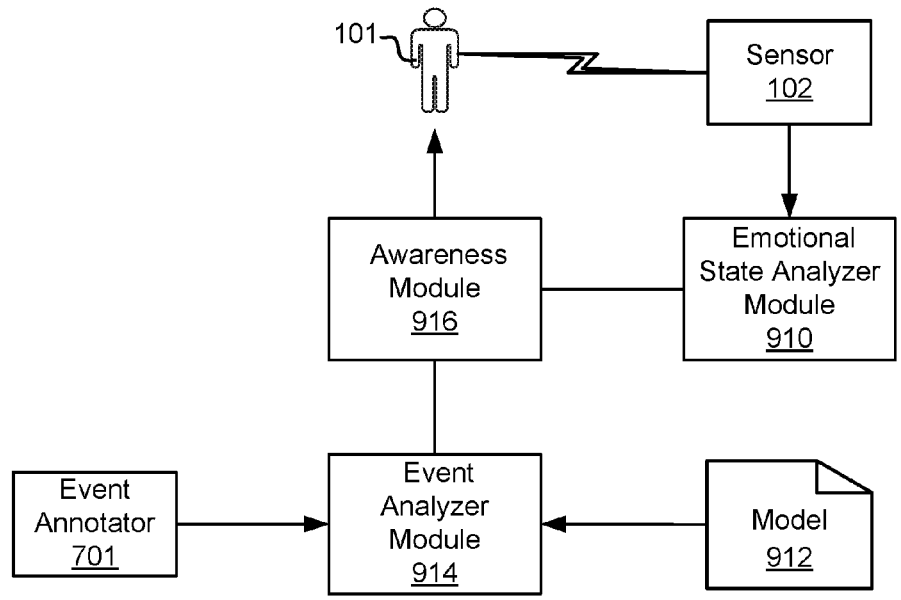
FIG. 2 illustrates one embodiment of a system configured to notify a user about a factor that influenced the emotional state of the user.

FIG. 2 illustrates one embodiment of a system configured to notify a user about a factor that influenced the emotional state of the user. Optionally, the system may notify the user about a factor that causes emotional imbalance. Additionally or alternatively, the system may be configured to notify the user about a factor that contributes to emotional balance. The illustrated system includes at least the following computer-executable modules: emotional state analyzer module 910, event analyzer module 914, and awareness module 916. The system may optionally include additional modules such as event annotator 701. In some embodiments, at least some of these modules may be part of, and/or utilize by, a software agent operating on behalf of the user.

Since it involves computer-executable modules (also referred to herein simply as "modules"), one more processors and memory may be required in order to realize the system. For example, a system similar to computer system 400 illustrated in FIG. 8, which includes processor 401 and memory 402, may be utilized in order to implement an embodiment of the system illustrated in FIG. 2.

The emotional state analyzer module 910 is configured to receive a measurement of affective response of the user 101, which corresponds to an event in which the user 101 has an experience, and to make a determination regarding the measurement. In one embodiment, the determination relates to whether the measurement indicates a state of emotional imbalance of the user 101. In another embodiment, the determination relates to whether the measurement indicates a state of emotional balance of the user 101.

In one embodiment, the measurement is taken with the sensor 102, which is coupled to the user 101, and the measurement comprises at least one of the following values: a physiological signal of the user 101, and a behavioral cue of the user 101.

The experience corresponding to the event (i.e., the experience the user 101 has) may be any of the various experiences described in this disclosure. In one embodiment, having the experience may involve doing at least one of the following: spending time at a certain location, consuming certain digital content, having a social interaction with a certain entity in the physical world, having a social interaction with a certain entity in a virtual world, viewing a certain live performance, performing a certain exercise, traveling a certain route, and consuming a certain product.

In some embodiments, the sensor 102 is utilized to take a plurality of measurements of affective response of the user 101 during the day in which the measurement corresponding to the event was taken. Optionally, for most of the plurality of measurements, the emotional state analyzer module 910 makes a determination that is not indicative of the state of emotional imbalance of the user 101. Alternatively, for most of the plurality of measurements, the emotional state analyzer module 910 makes a determination that is not indicative of the state of emotional balance of the user 101.

Determining whether a user is to be considered in a state of emotional balance or imbalance may be done in various ways in different embodiments. In one example, a determination of a state of emotional imbalance is made based on an assumption that when the user 101 is in the state of emotional imbalance, the measurement of affective response corresponding to the event indicates that an extent, to which the user 101 felt a certain emotion, reaches a threshold. In this example, the certain emotion may be one or more of the following emotions: anger, contempt, disgust, distress, and fear. Thus, for example, if the user 101 is feeling at least a certain level of distress, the user 101 may be considered to be in a state of emotional imbalance. In another example, a determination of a state of emotional imbalance is made based on an assumption that when the user 101 is in the state of emotional imbalance, the measurement of affective response corresponding to the event indicates that a level of stress felt by the user 101 reaches a threshold. For example, the level of stress may be manifested via various signals (modalities) such as elevated heart rate, frequent breaths, and sweating, which may be detected via a Galvanic Skin Response (GSR).

In one example, a determination of a state of emotional balance is made based on an assumption that when the user 101 is in the state of emotional balance, the measurement of affective response corresponding to the event indicates that an extent, to which the user 101 felt a certain emotion, reaches a threshold. In this example, the certain emotion may be one or more of the following emotions: happiness, and contentment. Thus, for example, if the user 101 is feeling at least a certain level of happiness, the user 101 may be considered to be in a state of emotional balance. In another example, a determination of a state of emotional balance is made based on an assumption that when the user 101 is in the state of emotional balance, the measurement of affective response corresponding to the event indicates that an extent to which the user 101 felt a certain emotion does not reach a threshold. In this example, the certain emotion may be one or more of the following emotions: anger, contempt, disgust, distress, and fear. Thus, for example, if the user's anger does not reach a certain level, the user 101 may be considered to be in a state of emotional balance. In yet another example, a determination of a state of emotional balance is made based on an assumption that when the user 101 is in the state of emotional balance, the measurement of affective response corresponding to the event indicates that a level of stress felt by the user 101 does not reach a certain threshold level.

It is to be noted that, in some embodiments, a measurement of affective response of the user 101 may indicate that the user 101 is in exactly one of the emotional states (emotional balance or emotional imbalance). In other embodiments, the measurement may be indicative of neither of those states.

Determining an emotional state based on a measurement of affective response may involve, in some embodiments, utilization of one or more earlier measurements of affective response, taken before the event. The measurement corresponding to the event may be compared to a measurement taken before the event start in order to determine what effect the event had.

In some embodiments, the emotional state analyzer module 910 is further configured to receive a prior measurement of affective response of the user 101, taken with the sensor 102 before the event, and to utilize the prior measurement to determine whether the measurement corresponding to the event is indicative of the user transitioning to a certain emotional state. In one embodiment, the certain emotional state the user transitioned to corresponds to a state of emotional balance. In another embodiment, the certain emotional state the user transitioned to corresponds to a state of emotional imbalance. Optionally, the determination that the measurement indicates the certain emotional state is made based on at least one of the following facts: the prior measurement does not reach a threshold and the measurement corresponding to the event reaches the threshold, and the prior measurement is outside of a certain range of values and the measurement corresponding to the event is in the certain range of values. Optionally, the prior measurement is taken at most five minutes before the start of the event. Optionally, the prior measurement is taken at most two hours before the start of the event.

In some embodiments, making a determination that a measurement indicates a certain emotional state, such as a state corresponding to emotional imbalance or a state corresponding to emotional balance, is based on the difference between an earlier measurement of the user 101, taken before the instantiation of the event, and the measurement corresponding to the event. Optionally, the determination that the user 101 is in the certain emotional state is made if the difference between the earlier measurement and the measurement corresponding to the event is at least a certain magnitude. Optionally, the determination that the user 101 is in the certain emotional state is made if the earlier measurement indicates that the user 101 was not in the certain emotional state (e.g., the earlier measurement does not reach a certain threshold) and the measurement corresponding to the event indicates that the user was in the certain emotional state (e.g., the measurement reaches the certain threshold). Optionally, the determination that the user 101 is in the certain emotional state is not made if the earlier measurement indicates that the user was in the certain emotional state, even if the measurement corresponding to the event also indicates that.

The event analyzer module 914 is configured, in one embodiment, to receive factors characterizing the event and to select a certain factor that, based on model 912 of the user 101, has an effect on the user 101 that is congruous with the measurement of affective response of the user 101. Optionally, each of the factors corresponds to at least one of the following: the user 101, the experience corresponding to the event (to which the measurement corresponds), and the instantiation of the event.

The model 912 is trained based on data comprising: measurements of affective response of the user 101, corresponding to events involving the user 101 having various experiences, and descriptions of the events. Thus, for example, the data includes at least a first measurement of the user 101 corresponding to a first event in which the user 101 had a first experience (e.g., the user 101 played a computer game) and a second measurement of the user 101 corresponding to a second event in which the user 101 had a second experience (e.g., the user 101 ate at a certain restaurant). In some embodiments, the data is collected over an extensive period of time (e.g., at least a certain number of days, if not weeks or months and even years). In some embodiments, collecting a large amount of data may enable training a model that can accurately reflect the user's biases towards many factors.

In one embodiment, the model 912 includes bias values of the user 101 corresponding to at least some of the factors characterizing the event. In this embodiment, for each factor from among the at least some of the factors, the model 912 includes a value describing an effect the factor has on the user 101 in terms of how it influences the affective response of the user 101. For example, the effect may be to increase the extent the user feels a certain emotion such as s happiness, surprise, anger, fear, disgust, or sadness. Optionally, the effect of the factor is represented an affective value, as described elsewhere in this disclosure.

In another embodiment, the model 912 includes parameters utilized by an Emotional Response Predictor (ERP). Optionally, analysis of the model 912 may reveal the effect of at least some of the factors characterizing the event on the user 101. For example, the model 912 may include a regression parameter corresponding to each of the at least some of the factors. Optionally, a bias value of a factor from among the factors that characterize the event may be determined by comparing the difference in the value of predicted affective response when the weight of the factor is changed, as discussed in more detail in the patent application in the patent application U.S. Ser. No. 15/184,401.

The event analyzer module 914 selects the certain factor, from among the factors that characterize the event, such that the certain factor is congruous with the measurement of affective response 101. Thus, the certain factor is expected to have an influence that is at least qualitatively similar to the measurement. For example, if the measurement indicates that the user 101 is in a state of emotional imbalance (and/or the user 101 transitioned to such a state), then the effect of the certain factor may be to increase the anger of the user, at least to a certain extent. In another example, if the measurement indicates that the user 101 is in a state of emotional balance (and/or the user 101 transitioned to such a state), then the effect of the certain factor may be to increase the happiness of the user, at least to a certain extent.

In one embodiment, the measurement of affective response and the effects of each of the at least some of the factors (determined based on the model 912) may be represented as vectors in a space that includes one or more dimensions. In this embodiment, the certain factor may be selected based on a similarity between the vector corresponding between the certain factor and the vector representing the measurement of affective response. For example, the angle between the vector representation of the effect of the certain factor on the user 101 and the vector representation of the measurement of affective response may be an acute angle. Optionally, the dot product between the two vectors may be greater than a certain threshold value.

In another embodiment, the measurement of affective response may be indicative of a certain emotional response and the model 912 indicates that, on average, the effect of the certain factor amounts to an increase in an extent to which the user 101 has the certain emotional response. Optionally, the certain emotional response comprises feeling at least one of the following emotions: anger, contempt, disgust, distress, and fear.

There certain factor selected by the event analyzer module 914 may correspond to one or more of various aspects of the event. Following are some examples of factors that may be selected as the "certain factor". Each of these factors may influence the user 101 in a certain way as indicated by the model 912. Optionally, the model 912 is indicative of whether the factor positively or negatively effects the user 101, and to what extent.

In one example, the certain factor may represent having a certain person (other than the user 101) be part of the experience. For example, in an event in which the user 101 had lunch and reach emotional imbalance, the reason (the certain factor) responsible for the user 101 getting extremely angry during an event that involve eating lunch was not the quality of the food or the weather, but rather the company with whom the user 101 ate.

In another example, the certain factor may represent a certain activity that was part of the event and/or a certain characteristic of the event. For example, the certain factor may correspond to a certain exercise that the user 101 enjoys. Thus, an event in which the user 101 was in a state of emotional balance may be due primarily to the exercise, and not due to other factors such as the location in which the user had the exercise. In another example, the certain factor may be a certain sports team. Thus, for instance, if the user 101 is a fan of the certain sports team, then the influence of the factor may be positive (assuming they are playing well). But if the user 101 is not a fan (or even hates that team), then an event involving watching a game in which that teams participates may have a negative effect on the user 101 (especially of the team plays well).

In yet another example, the certain factor may represent the fact that the event involves being at a certain location. For example, a factor such as "being outdoors" or "being in a small room" may influence the user 101 in a certain way.

In still another example, the certain factor may represent a certain situation of the user 101 that is one of the following: being hungry, being tired, being late to an appointment, having insufficient funds, being too cold, and being too warm. Each of these factors may influence how the user feels when having an experience. For example, the user 101 may be a person who becomes very agitated when hungry but is caviler about being late to appointments.

The factors characterizing the event which are provided to the event analyzer module 914 are received, in some embodiments, from a description of the event which is generated by event annotator 701, which is discussed in more detail elsewhere in this disclosure. Optionally, the event annotator 701 is a module utilized by a software agent operating on behalf of the user 101.

The awareness module 916 is configured, in one embodiment, to notify the user 101 about the certain factor selected by the event analyzer module 914. Optionally, notifying the user 101 is done responsive to a determination generated by the emotional state analyzer module 910 that the measurement of affective response of the user 101 indicates a certain emotional state. In one embodiment, the certain emotional state corresponds to a state of emotional balance. In another embodiment, the certain emotional state corresponds to a state of emotional imbalance.

A notification provided to the user 101 about the certain factor may describe the certain factor and/or may describe the effect of the certain factor on the user. Optionally, the effect relates to how the certain factor effected the user 101 in the event (e.g., by determining what proportion of the affective response in the measurement may be attributed to the certain factor). Additionally or alternatively, the effect may relate to how the certain factor effects the user 101 in general (e.g., based on a bias value for the certain factor determined utilizing the model 912). A description of the effect of the certain factor may be qualitative (e.g., describing whether the effect of the certain factor may be considered calming or agitating). Additionally or alternatively, the description of the effect of the certain factor may be quantitative. For example, the description relay the effect in terms of an increase to the pulse or a change in emotional response (e.g., an increase in anger of 2 points for anger levels on a scale of 1 to 10). In one example, the notification may describe how the user 101 becomes more relaxed when listening to country music. In another example, the notification may describe how the user 101 becomes enraged by anything related to Barney the Dinosaur. In still another embodiment, the notification may describe how much being next to a certain acquaintance made the user 101 nervous in the event the use just had (e.g., a social outing with a bunch of friends).

There are various ways in which the awareness module 916 may provide the user 101 with a notification regarding the certain factor. In one example, the user 101 may be notified about the certain factor via a user interface. For example, a software agent may tell the user 101 about the certain factor via a voice message heard through earphones, a text message on a screen, and/or video presented via a display such as an augmented-reality display (e.g., video image of a character that converses with the user 101).

In some embodiments, a notification provided to the user 101 about the certain factor may emphasize the certain factor in a description of the event. For example, if the certain factor corresponds to a person or object, the notification may include emphasizing the certain factor in images related to the event (e.g., adding a glowing effect around the certain factor in a video of the event taken by a camera worn by the user 101). In another example, if the certain factor relates to audio (e.g., a certain type of sound), the audio corresponding to the certain factor may be made louder in a replay of the event.

The awareness module 916 may notify the user 101 about the certain factor at different times. In some embodiments, the notification module 916 may notify the user 101 about the certain factor following the selection of the certain factor. Optionally, this may be done during the instantiation of the event (i.e., while the user 101 is still having the experience corresponding to the event). In other embodiments, the notification module 916 may notify the user 101 about the certain factor after the event took place. For example, the notification may be provided to the user 101 a few minutes or even a few hours after the event. In still other embodiments, the notification may be provided as part of a report that compiles analysis of measurements of affective response to several events. For example, the notification may describe the effect the certain factor had in several events characterized by the certain factor.

In different embodiments, notifying the user 101 about the certain factor may serve one or more purposes and/or may have one or more benefits. In one example, notifying the user 101 about the certain factor may serve to make the user more aware of the certain factor and how it contributed to the user reaching a certain emotional state (e.g., a state corresponding to emotional imbalance or emotional balance).

Having better awareness of the certain factor can help the user 101 cope with (future) events. For example, if the certain factor is one that irritates the user 101, then by knowing ahead of time that the user 101 is about to have a new event that is characterized by the certain factor, the user 101 may be better prepared to cope with the new event when the new event happens. Since the user 101 is aware of the certain factor and expecting it, the effect of the certain factor may be not be as bad as it typically is when the user 101 is less aware and/or prepared for it. Similarly, if the certain factor has a positive effect on the user 101, then if the user 101 is faced with a difficult event, knowledge of the certain factor can help claim the user 101 and enable the user to better handle the difficult event when it occurs. In this case, the user 101 can stay focused and/or think of the certain factor instead of other factors that characterize the event, which may have a more negative effect on the user 101.

Being aware of the effect the certain factor has on the user 101 can also help the user 101 make choices regarding future events. For example, the user 101 may prefer to be involved in events that are not characterized by the certain factor, if the user 101 is made aware of the fact that the certain factor may contribute to emotional imbalance. However, if the certain factor contributes to emotional balance, the user 101 may try to be involved in events characterized by the certain factor.

In some embodiments, a software agent operating on behalf of the user 101 may receive information from the awareness module 916, such as information regarding certain factors that contribute to emotional balance or emotional imbalance of the user 101. Optionally, the software agent may utilize this information when suggesting and/or selecting future experiences for the user.

As described above, notifying a user about a certain factor that effects the user's emotional state (e.g., contributing to emotional balance or emotional imbalance), may involve performance of various operations. Following are descriptions of steps that may be performed in various embodiments of methods for notifying a user of such a factor. The steps described below may, in some embodiments, be part of the steps performed by an embodiment of a system described above, such as a system modeled according to FIG. 2. In some embodiments, instructions for implementing a method described below may be stored on a computer-readable medium, which may optionally be a non-transitory computer-readable medium. In response to execution by a system including a processor and memory, the instructions cause the system to perform operations that are part of the method.

Figure 3:
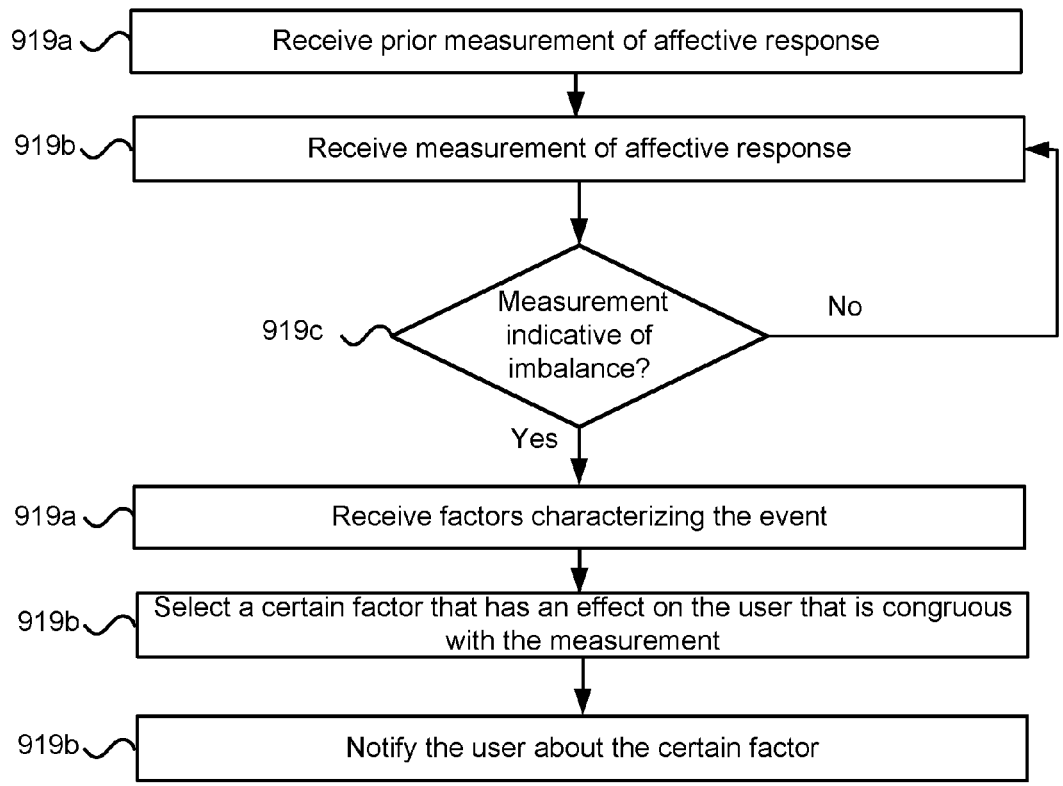
FIG. 3 illustrates steps involved in one embodiment of a method for notifying a user about a cause of emotional imbalance.

FIG. 3 illustrates steps involved in one embodiment of a method for notifying a user about a cause of emotional imbalance. The steps illustrated in FIG. 3 may be used, in some embodiments, by systems modeled according to FIG. 2.

In one embodiment, the method for notifying a user about a cause of emotional imbalance includes at least the following steps:

In Step 919b, receiving, by a system comprising a processor and memory, a measurement of affective response of the user, which corresponds to an event. That is, the measurement is taken while the user has the experience corresponding to the event or shortly thereafter. Optionally, the measurement is taken with the sensor 102. Optionally, the user is the user 101. Optionally, the measurement comprises at least one of the following values: a physiological signal of the user, a behavioral cue of the user.

In Step 919c, determining whether the measurement received in Step 919b indicates a state of emotional imbalance of the user. Optionally, the determining is done utilizing the emotional state analyzer module 910. Optionally, upon determining that the measurement does not indicate a state of emotional imbalance, the method terminates. Alternatively, in some embodiments, upon determining that the measurement does not indicate a state of emotional imbalance, the method may involve returning to Step 919b, in order to receive additional measurements (this option is illustrated as the "No" branch).

In Step 919d, following the "Yes" branch, receiving factors that characterize the event. Optionally, each of the factors corresponds to at least one of the following: the user, the experience corresponding to the event, and the instantiation of the event.

In Step 919e, selecting a certain factor that characterizes the event which, based on a model of the user, has an effect on the user that is congruous with the measurement. Optionally, the model is the model 912, described above. Optionally, the selection is done utilizing the event analyzer module 914.

And in Step 919f, responsive to a determination in Step 919c that the measurement indicates the state of emotional imbalance of the user, notifying the user about the certain factor. Optionally, notifying the user in this step is done utilizing the awareness module 916, as described above.

It is to be noted that in some embodiments, steps 919d and 919e may be performed even if the determination made in step 919c indicates that the measurement taken in Step 919b does not indicate a state of emotional imbalance of the user. Optionally, steps 919d and 919e may still be performed as part of collection and analysis of data related to events involving the user (e.g., by a software agent operating on behalf of the user).

In some embodiments, the method optionally includes an additional Step 919a that involves receiving a prior measurement of affective response of the user, which is taken with the sensor before the event, and utilizing the prior measurement for the determining of whether the measurement corresponding to the event is indicative of the user transitioning to the state of emotional imbalance. For example, a determination in Step 919c that indicates that the measurement received in Step 919b indicates a state of emotional imbalance of the user may be based on the fact that the prior measurement received in Step 919a has a value that is below a threshold, while the measurement receive in Step 919b had a value that is above the threshold.

In some embodiments, a plurality of measurements of affective response of the user are taken with a sensor during the day in which the measurement corresponding to the event was taken (i.e., the measurement received in Step 919b). Usually, the user should not be in a state of emotional imbalance throughout the day; thus, for most of the measurements, a determination made in Step 919c is not indicative of the state of emotional imbalance of the user.

Reaching a determination that the measurement received in Sep 919b indicates the state of emotional imbalance of the user may done in different ways. In one embodiment, making the determination that the measurement indicates the state of emotional imbalance of the user is done based on the measurement of affective response received in Step 919b indicating that an extent, to which the user felt a certain emotion, reaches a first threshold. Optionally, the certain emotion is at least one of the following emotions: anger, contempt, disgust, distress, and fear. In another embodiment, making the determination that the measurement indicates the state of emotional imbalance of the user is done based on the measurement of affective response received in Step 919b indicating that a level of stress felt by the user reaches a second threshold.

In one embodiment, the method described above may optionally include a step of generating a description of the event that comprises the factors characterizing the event. Optionally, the description is created by the event annotator 701.

Given that in some embodiments, not all measurements of affective response of a user will be indicative of a state of emotional imbalance of the user, the user might not be notified about a certain factor corresponding to each event (e.g., in Step 919f described above). In these embodiments, a first measurement corresponding to a first event may be indicative of emotional imbalance, while a second measurement corresponding to a second event may not. Consequently, the user may be notified about a first factor that characterizes the first event and is congruous with the first measurement, but may not be notified above a second factor that characterizes the second event and is congruous with the second measurement. Such a different behavior with respect to the first and second measurements may involve performing different operations, as described in the following embodiment.

In one embodiment, a method for notifying a user about a cause of emotional imbalance includes at least the following steps:

In Step 1, receiving a first measurement of affective response of the user, which corresponds to a first event. The first event involves the user having a first experience, and the first measurement is taken with a sensor coupled to the user.

In Step 2, determining that the first measurement indicates a state of emotional imbalance of the user. Optionally, the determination is made by the emotional state analyzer module 910.

In Step 3, receiving first set of factors that characterize the first event.

In Step 4, selecting a first factor, from among the first set, which, based on a model of the user, has an effect on the user that is congruous with the first measurement of affective response of the user. Optionally, the first factor is selected by the event analyzer module 914.

In Step 5, notifying the user about the first factor. Optionally, the user is notified by the awareness module 916.

In Step 6, receiving a second measurement of affective response of the user, which corresponds to a second event. The second event involves the user having a second experience, and the second measurement is taken with a sensor coupled to the user. Optionally, the first experience is different from the second experience. Alternatively, the first and second events may involve having the same experience.

In Step 7, determining that the second measurement does not indicate the state of emotional imbalance of the user. Optionally, the determination is made by the emotional state analyzer module 910.

And in Step 8, refraining from notifying the user about a second factor, which belongs to a second set of factors characterizing the second event, and which based on the model of the user, is congruous with the second measurement of affective response of the user.

Figure 4:
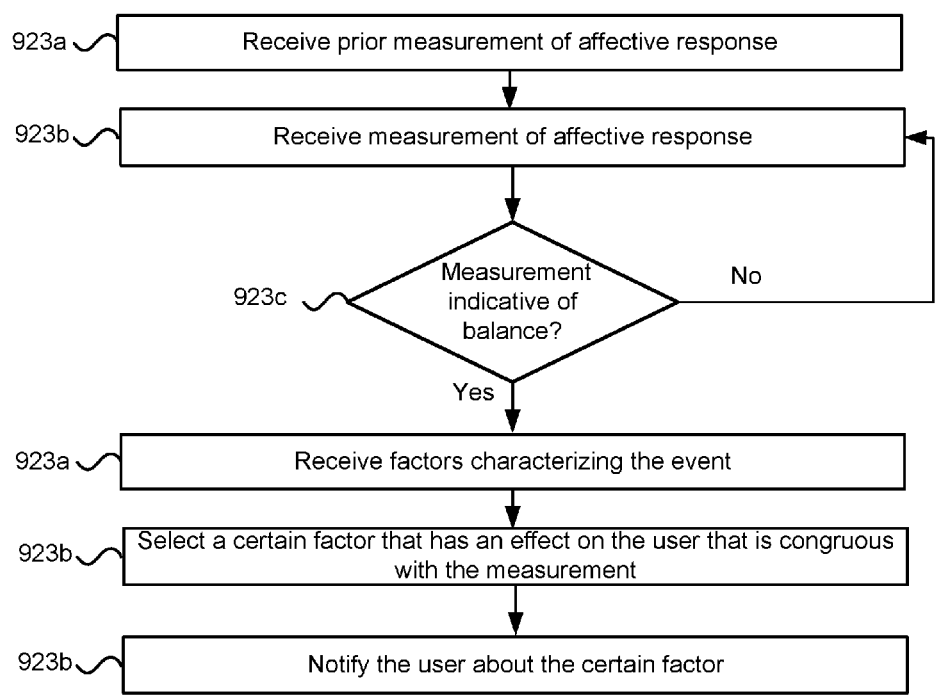
FIG. 4 illustrates steps involved in one embodiment of a method for notifying a user about a cause contributing to emotional balance.

FIG. 4 illustrates steps involved in one embodiment of a method for notifying a user about a cause contributing to emotional balance. The steps illustrated in FIG. 4 may be used, in some embodiments, by systems modeled according to FIG. 2.

In one embodiment, the method for notifying a user about a cause contributing emotional balance includes at least the following steps:

In Step 923b, receiving, by a system comprising a processor and memory, a measurement of affective response of the user, which corresponds to an event. That is, the measurement is taken while the user has the experience corresponding to the event or shortly thereafter. Optionally, the measurement is taken with the sensor 102. Optionally, the user is the user 101. Optionally, the measurement comprises at least one of the following values: a physiological signal of the user, a behavioral cue of the user.

In Step 923c, determining whether the measurement received in Step 923b indicates a state of emotional balance of the user. Optionally, the determining is done utilizing the emotional state analyzer module 910. Optionally, upon determining that the measurement does not indicate a state of emotional balance, the method terminates. Alternatively, in some embodiments, upon determining that the measurement does not indicate a state of emotional balance, the method may involve returning to Step 923b, in order to receive additional measurements (this option is illustrated as the "No" branch).

In Step 923d, following the "Yes" branch, receiving factors that characterize the event. Optionally, each of the factors corresponds to at least one of the following: the user, the experience corresponding to the event, and the instantiation of the event.

In Step 923e, selecting a certain factor that characterizes the event which, based on a model of the user, has an effect on the user that is congruous with the measurement. Optionally, the model is the model 912, described above. Optionally, the selection is done utilizing the event analyzer module 914.

And in Step 923f, responsive to a determination in Step 923c that the measurement indicates the state of emotional balance of the user, notifying the user about the certain factor. Optionally, notifying the user in this step is done utilizing the awareness module 916, as described above.

It is to be noted that in some embodiments, steps 923d and 923e may be performed even if the determination made in step 923c indicates that the measurement taken in Step 923b does not indicate a state of emotional balance of the user. Optionally, steps 923d and 923e may still be performed as part of collection and analysis of data related to events involving the user (e.g., by a software agent operating on behalf of the user).

In some embodiments, the method optionally includes an additional Step 923a that involves receiving a prior measurement of affective response of the user, which is taken with the sensor before the event, and utilizing the prior measurement for the determining of whether the measurement corresponding to the event is indicative of the user transitioning to the state of emotional balance. For example, a determination in Step 923c that indicates that the measurement received in Step 923b indicates a state of emotional balance of the user may be based on the fact that the prior measurement received in Step 923a has a value that is below a threshold, while the measurement receive in Step 923b had a value that is above the threshold. For example, the prior measurement may correspond to a low level of happiness, while the measurement received in Step 923b may correspond to a higher level of happiness.

Reaching a determination that the measurement received in Sep 923b indicates the state of emotional balance of the user may done in different ways. In one embodiment, making the determination that the measurement indicates the state of emotional balance of the user is done based on the measurement of affective response received in Step 923b indicating that an extent, to which the user felt a certain first emotion, reaches a first threshold. Optionally, the certain first emotion is at least one of the following emotions: happiness, and contentment. In another embodiment, making the determination that the measurement indicates the state of emotional balance of the user is done based on the measurement of affective response received in Step 923b indicating that an extent to which the user felt a certain second emotion does not reach a second threshold. Optionally, the certain second emotion is at least one of the following emotions: anger, contempt, disgust, distress, and fear. In yet another embodiment, making the determination that the measurement indicates the state of emotional balance of the user is done based on the measurement of affective response received in Step 923b indicating that a level of stress felt by the user does not reach a third threshold.

In one embodiment, the method described above may optionally include a step of generating a description of the event that comprises the factors characterizing the event. Optionally, the description is created by the event annotator 701.

Given that in some embodiments, not all measurements of affective response of a user will be indicative of a state of emotional balance of the user, the user might not be notified about a certain factor corresponding to each event (e.g., in Step 923f described above). In these embodiments, a first measurement corresponding to a first event may be indicative of emotional balance, while a second measurement corresponding to a second event may not. Consequently, the user may be notified about a first factor that characterizes the first event and is congruous with the first measurement, but may not be notified above a second factor that characterizes the second event and is congruous with the second measurement. Such a different behavior with respect to the first and second measurements may involve performing different operations, as described in the following embodiment.

In one embodiment, a method for notifying a user about a cause contributing to emotional balance includes at least the following steps:

In Step 1, receiving a first measurement of affective response of the user, which corresponds to a first event. The first event involves the user having a first experience, and the first measurement is taken with a sensor coupled to the user.

In Step 2, determining that the first measurement indicates a state of emotional balance of the user. Optionally, the determination is made by the emotional state analyzer module 910.

In Step 3, receiving first set of factors that characterize the first event.

In Step 4, selecting a first factor, from among the first set, which, based on a model of the user, has an effect on the user that is congruous with the first measurement of affective response of the user. Optionally, the first factor is selected by the event analyzer module 914.

In Step 5, notifying the user about the first factor. Optionally, the user is notified by the awareness module 916.

In Step 6, receiving a second measurement of affective response of the user, which corresponds to a second event. The second event involves the user having a second experience, and the second measurement is taken with a sensor coupled to the user. Optionally, the first experience is different from the second experience. Alternatively, the first and second events may involve having the same experience.

In Step 7, determining that the second measurement does not indicate the state of emotional balance of the user. Optionally, the determination is made by the emotional state analyzer module 910.

And in Step 8, refraining from notifying the user about a second factor, which belongs to a second set of factors characterizing the second event, and which based on the model of the user, is congruous with the second measurement of affective response of the user.

The systems and methods described above which are related to FIG. 2, FIG. 3, and/or FIG. 4, involve selection of a certain factor that is congruous with a measurement of affective response corresponding to an event. In order to select the certain factor corresponds to a certain effect on the user (e.g., contributing to emotional imbalance or emotional balance), the user must have had the experience corresponding to the event. Thus, in those embodiments, analysis of an event happens during and/or after the instantiation of the event. However, analysis and selection of a certain factor that has a certain effect on the user may be done on events that have not taken place yet. In these embodiments, rather than relying on a measurement of affective response corresponding to an event, a predicted affective response may be utilized. The predicted affective response can be generated utilizing a prediction of an Emotional Response Predictor (ERP) that is given an input generated from a description of the event. To make the prediction, the ERP can utilize a model of the user (e.g., the model 912 mentioned above). Thus, selection of the certain factor can be done before the user has the event. This can help the user cope with the event even before having it and can also assist in choosing and/or modifying events for the user. Embodiments that take this approach are described below.

Figure 5:
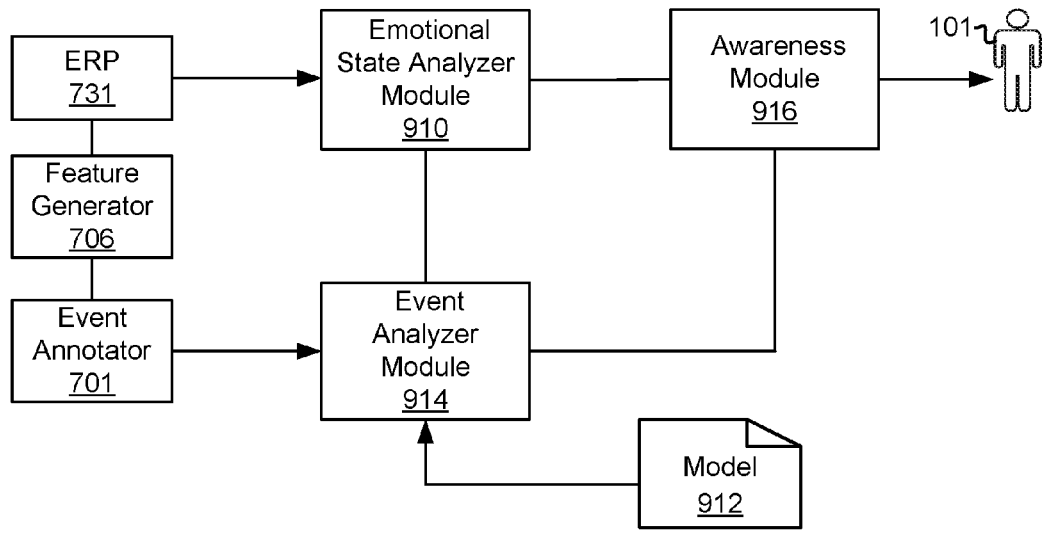
FIG. 5 illustrates one embodiment of a system configured to utilize a predicted affective response to notify a user about a factor that may influence the emotional state of the user.

FIG. 5 illustrates one embodiment of a system configured to utilize a predicted affective response to notify a user about a factor that may influence the emotional state of the user. Optionally, the system may notify the user about a factor that may cause emotional imbalance. In such a case, the system may be referred to as a system for notifying (or warning) the user about a cause of imminent emotional imbalance, since if the user being involved in an event that is characterized by the factor can cause the user to be in a state of emotional imbalance.

Additionally or alternatively, the system may be configured to notify the user about a factor that may contribute to emotional balance. The illustrated system includes at least the following computer-executable modules: feature generator 706, the Emotional Response Predictor (ERP) 731, the emotional state analyzer module 910, the event analyzer module 914, and the awareness module 916. The system may optionally include additional modules such as the event annotator 701. In some embodiments, at least some of these modules may be part of, and/or utilize by, a software agent operating on behalf of the user.

Since it involves computer-executable modules (also referred to herein simply as "modules"), one more processors and memory may be required in order to realize the system. For example, a system similar to computer system 400 illustrated in FIG. 8, which includes processor 401 and memory 402, may be utilized in order to implement an embodiment of the system illustrated in FIG. 5.

The feature generator 706 is configured to: receive a description indicative of factors characterizing an event that involves user having an experience, and to utilize the description to generate one or more values (feature values). Optionally, the feature values generated from the description of the event correspond to the factors of the event (i.e., factors characterizing the event). Optionally, each of the factors characterizing an event corresponds to at least one of the following: the user corresponding to the event, the experience corresponding to the event, and the instantiation of the event. For example, the feature values may have the weights of the factors themselves and/or may be computed based on the weights of the factors. In another example, description itself may be given in the form of feature values, and thus the feature generator 706 may use the description itself without need for much additional processing. In some embodiments, the description of the event is generated by the event annotator 701, which is discussed in more detail elsewhere in this disclosure. Optionally, the event annotator 701 is a module utilized by a software agent operating on behalf of the user 101.

The experience corresponding to the event may be any of the various experiences described in this disclosure. In one embodiment, having the experience may involve doing at least one of the following: spending time at a certain location, consuming certain digital content, having a social interaction with a certain entity in the physical world, having a social interaction with a certain entity in a virtual world, viewing a certain live performance, performing a certain exercise, traveling a certain route, and consuming a certain product.

The description of the event may, in some embodiments, be a description generated for the user 101. For example, it may include factors relevant to the user 101 and/or created by a software agent operating on behalf of the user 101. In another example, the description may be of an event the user 101 already had in the pass. In other embodiments, the description may be a generic description of the event, which may be suitable for, and/or utilized by, multiple users.

The ERP 731 is configured, in one embodiment, to utilize a first model of the user 101 to predict, based on the feature values generated by the feature generator 706 from the description of the event, a predicted affective response corresponding to the event. The predicted affective response is indicative of the affective response of the user 101 due to the event. Optionally, the predicted affective response represents a value of a measurement of affective response of the user 101, which corresponds to the event and is taken with the sensor 102 (were such a measurement actually taken, which may not be the case). Optionally, the predicted affective response may be expressed in the same terms as a measurement of affective respond which is provided to the emotional state analyzer 910 in other embodiments described herein (e.g., embodiments modelled according to FIG. 2). Optionally, the predicted affective response is represented by a type of an affective value described in this disclosure.

In one embodiment, the first model of the user is the model 912. In another embodiment, the first model may be different from the model 912 (e.g., it may be a model for a different type of predictor and/or be trained with different training data than the model 912).

It is to be noted that while the description utilized by the feature generator 706 to generate the feature values may not necessarily be a description of an event the user 101 had in the past or is scheduled to have in the future, the fact that the first model used to predict affective response is a model of the user 101 means that the predicted affective response may be considered the affective response the user 101 is expected to have because of the event. Optionally, the first model is considered to be a model of the user 101 by virtue of at least some of the training data used to generate the first model being data corresponding to the user 101. For example, the training data may contain measurements of affective response of the user 101 and descriptions of events to which the measurements correspond, as discussed in more detail above with reference to the model 912.

The emotional state analyzer module 910 is configured, in one embodiment, to receive the predicted affective response generated utilizing the ERP 731, which corresponds to the event, and to make a determination regarding the predicted affective response. In one embodiment, the determination relates to whether the predicted affective response indicates a state of emotional imbalance of the user 101. In another embodiment, the determination relates to whether the predicted affective response indicates a state of emotional balance of the user 101. It is to be noted that in this embodiment, the emotional state analyzer module 910 may use the predicted affective response in a similar capacity to how it uses the measurement of affective response in embodiments modelled according to FIG. 2. However, rather than relying on a measured value (e.g., measured utilizing the sensor 102), the emotional state analyzer 910 uses a predicted value, in the form of the predicted affective response generated by the ERP 731.

Determining whether a predicted affective response indicates the user will be in a state of emotional balance or imbalance may be done in various ways in different embodiments, similar to how the determination regarding the state of the user 101 is done based on a measurement of affective response in embodiments modelled according to FIG. 2. In one example, a determination of a state of emotional imbalance is made based on an assumption that when the user 101 is predicted to be in a state of emotional imbalance, the predicted affective response corresponding to the event indicates that an extent, to which the user 101 is predicted to feel a certain emotion, reaches a threshold. In this example, the certain emotion may be one or more of the following emotions: anger, contempt, disgust, distress, and fear. Thus, for example, if the user 101 is predicted to feel at least a certain level of distress, the user 101 may be predicted to be in a state of emotional imbalance due to the event. In another example, a determination of a state of emotional imbalance is made based on an assumption that when the user 101 is predicted to be in the state of emotional imbalance, the predicted affective response corresponding to the event indicates that a level of stress the user 101 is predicted to feel reaches a threshold.

It is to be noted that stating that the user 101 is "predicted to be in a certain emotional state" means that if the event related to the prediction takes place, then according to the model used to make the predicted affective response, the user 101 is expected to be in the certain emotional state due to the event.

In one example, a determination of a state of emotional balance is made based on an assumption that when the user 101 is predicted to be in a state of emotional, the predicted affective response corresponding to the event indicates that an extent, to which the user 101 felt a certain emotion, reaches a threshold. In this example, the certain emotion may be one or more of the following emotions: happiness, and contentment. Thus, for example, if the user 101 is feeling at least a certain level of happiness, the user 101 may be considered to be in a state of emotional balance. In another example, a determination of a state of emotional balance is made based on an assumption that when the user 101 is predicted to be in a state of emotional, the predicted affective response corresponding to the event indicates that an extent to which the user 101 is predicted to feel a certain emotion does not reach a threshold. In this example, the certain emotion may be one or more of the following emotions: anger, contempt, disgust, distress, and fear. Thus, for example, if the user's anger is not predicted reach a certain level, the user 101 may be predicted to be in a state of emotional balance. In yet another example, a determination of a state of emotional balance is made based on an assumption that when the user 101 is predicted to be in a state of emotional, the predicted affective response corresponding to the event indicates that a level of stress the user 101 is predicted to feel does not reach a certain threshold level.

It is to be noted that, in some embodiments, predicted affective response of the user 101 may indicate that the user 101 is predicted to be in one of the emotional states (emotional balance or emotional imbalance). In other embodiments, the predicted affective response may be indicative of neither of those states.

Determining an emotional state based on predicted affective response may involve, in some embodiments, utilization of one or more measurements of affective response, taken before the generation of the predicted affective response. The predicted affective response may be compared to a measurement taken earlier in order to determine what effect the event had.

In some embodiments, the emotional state analyzer module 910 is further configured to receive a prior measurement of affective response of the user 101, taken with the sensor 102, and to utilize the prior measurement to determine whether the predicted affective response corresponding to the event is indicative of the user transitioning to a certain emotional state. In one embodiment, the certain emotional state the user transitioned to corresponds to a state of emotional balance. In another embodiment, the certain emotional state the user transitioned to corresponds to a state of emotional imbalance. Optionally, the determination that the predicted affective response indicates the certain emotional state is made based on at least one of the following facts: the prior measurement does not reach a threshold and the predicted affective response reaches the threshold, and the prior measurement is outside of a certain range of values and the predicted affective response is in the certain range of values.

In some embodiments, making a determination that a predicted affective response indicates a certain emotional state, such as a state corresponding to emotional imbalance or a state corresponding to emotional balance, is based on the difference between an earlier measurement of the user 101, taken before generating the predicted affective response, and the predicted affective response corresponding to the event. Optionally, the determination that the user 101 is predicted to be in a certain emotional state is made if the difference between the earlier measurement and the predicted affective response corresponding to the event is at least a certain magnitude. Optionally, the determination that the user 101 is in the certain emotional state is made if the earlier measurement indicates that the user 101 was not in the certain emotional state (e.g., the earlier measurement does not reach a certain threshold) and the predicted affective response corresponding to the event indicates that the user 101 is predicted to be in the certain emotional state (e.g., the predicted affective response reaches the certain threshold). Optionally, the determination that the user 101 is predicted to be in the certain emotional state is not made if the earlier measurement indicates that the user was in the certain emotional state, even if the predicted affective response corresponding to the event also indicates that.

The event analyzer module 914 is configured, in one embodiment, to receive factors characterizing the event and to select a certain factor that, based on a second model of the user 101, has an effect on the user 101 that is congruous with the predicted affective response of the user 101, generated by the ERP 731. Optionally, each of the factors corresponds to at least one of the following: the user 101, the experience corresponding to the event (to which the measurement corresponds), and the instantiation of the event.

In one embodiment, the second model of the user is the model 912. In another embodiment, the second model may be different from the model 912 (e.g., it may be a model for a different type of predictor and/or be trained with different training data than the model 912). In some embodiments, the first and second models respectively utilized by the ERP 731 and the event analyzer module 914 may be the same model. In other embodiments, they may be different models. For example, the first model may be a model for a neural network and the second model may include bias values of the user 101.

The event analyzer module 914 selects the certain factor, from among the factors that characterize the event, such that the certain factor is congruous with the predicted affective response. Thus, the certain factor is expected to have an influence that is at least qualitatively similar to the predicted affective response. For example, if the predicted affective response indicates that the user 101 is predicted to be in a state of emotional imbalance (and/or the user 101 is expected to transition to such a state), then the effect of the certain factor may be to increase the anger of the user, at least to a certain extent. In another example, if the predicted affective response indicates that the user 101 is predicted to be in a state of emotional balance (and/or the user 101 is expected to transition to such a state), then the effect of the certain factor may be to increase the happiness of the user, at least to a certain extent.

In one embodiment, the predicted affective response and the effects of each of the at least some of the factors (determined based on the second model) may be represented as vectors in a space that includes one or more dimensions. In this embodiment, the certain factor may be selected based on a similarity between the vector corresponding between the certain factor and the vector representing the predicted affective response. For example, the angle between the vector representation of the effect of the certain factor on the user 101 and the vector representation of the predicted affective response may be an acute angle. Optionally, the dot product between the two vectors may be greater than a certain threshold value.

In another embodiment, the predicted affective response may be indicative of a certain emotional response and the second model indicates that, on average, the effect of the certain factor amounts to an increase in an extent to which the user 101 has the certain emotional response. Optionally, the certain emotional response comprises feeling at least one of the following emotions: anger, contempt, disgust, distress, and fear.

Similarly to the certain factor selected in embodiments modelled according to FIG. 2, there certain factor selected by the event analyzer module 914 may correspond to one or more of various aspects of the event. For example, the certain factor may represent having a certain person (other than the user 101) be part of the experience, the certain factor may represent a certain activity that was part of the event and/or a certain characteristic of the event, the certain factor may represent the fact that the event involves being at a certain location, and/or the certain factor may represent a certain situation of the user 101 during the event.

In a similar fashion to it role in embodiments modelled according to FIG. 2, in embodiments modelled according to FIG. 5, the awareness module 916 is configured to notify the user 101 about the certain factor selected by the event analyzer module 914. Optionally, notifying the user 101 is done responsive to a determination generated by the emotional state analyzer module 910 that the predicted affective response of the user 101 indicates a certain emotional state. In one embodiment, the certain emotional state corresponds to a state of emotional balance. In another embodiment, the certain emotional state corresponds to a state of emotional imbalance.

In different embodiments, notifying the user 101 about the certain factor may serve one or more purposes and/or may have one or more benefits. In one example, notifying the user 101 about the certain factor may serve to make the user 101 more aware of the certain factor and how it may contribute to the user reaching a certain emotional state (e.g., a state corresponding to emotional imbalance or emotional balance). In some embodiments, being aware of the effect the certain factor has on the user 101 can help the user 101 make choices regarding future events. For example, the user 101 may prefer to be involved in events that are not characterized by the certain factor, if the user 101 is made aware of the fact that the certain factor may contribute to emotional imbalance. However, if the certain factor contributes to emotional balance, the user 101 may try to be involved in events characterized by the certain factor.

As described above, notifying a user about a certain factor that is predicted to effect the user's emotional state (e.g., it is predicted to contribute to emotional balance or emotional imbalance), may involve performance of various operations. Following are descriptions of steps that may be performed in various embodiments of methods for notifying a user of such a factor. The steps described below may, in some embodiments, be part of the steps performed by an embodiment of a system described above, such as a system modeled according to FIG. 5. In some embodiments, instructions for implementing a method described below may be stored on a computer-readable medium, which may optionally be a non-transitory computer-readable medium. In response to execution by a system including a processor and memory, the instructions cause the system to perform operations that are part of the method.

Figure 6:
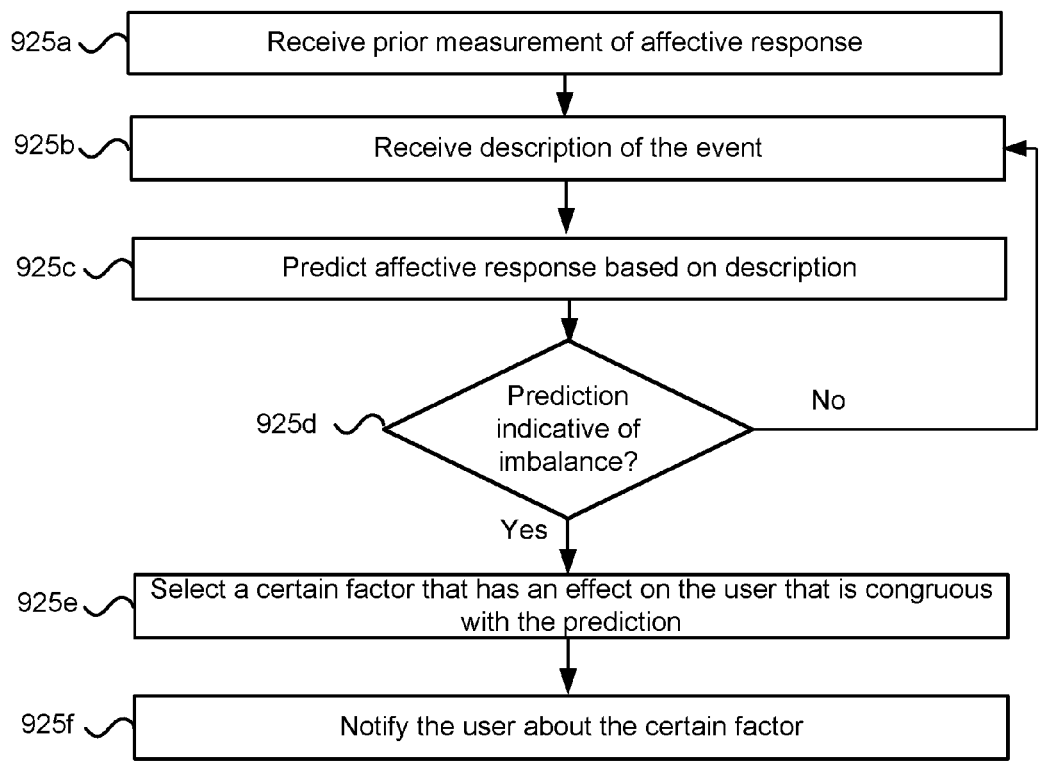
FIG. 6 illustrates steps involved in one embodiment of a method for warning a user of a cause of an imminent emotional imbalance.

FIG. 6 illustrates steps involved in one embodiment of a method for warning a user of a cause of an imminent emotional imbalance. The steps illustrated in FIG. 6 may be used, in some embodiments, by systems modeled according to FIG. 2.

In one embodiment, the method for warning a user about a cause of imminent emotional imbalance includes at least the following steps:

In Step 925*b*, receiving, by a system comprising a processor and memory, a description indicative of factors characterizing an event that involves the user having an experience. Optionally, each of the factors corresponds to at least one of the following: the user, the experience, and the instantiation of the event. Optionally, the description is generated by the event annotator 701.

In Step 925*c*, computing, from an input based on the description and utilizing a first model of the user, a predicted affective response corresponding to the event. Optionally, the first model is the model 912. Optionally, computing the predicted affective response is done utilizing the ERP 731.

In Step 925*d*, determining whether the predicted affective response computed in Step 925*c* indicates a state of emotional imbalance of the user. Optionally, the determining is done by the emotional state analyzer module 910. Optionally, upon determining that the predicted affective response does not indicate a state of emotional imbalance, the method terminates. Alternatively, in some embodiments, upon determining that the predicted affective response does not indicate a state of emotional imbalance, the method may involve returning to Step 925*b*, in order to receive additional descriptions (this option is illustrated as the "No" branch).

In Step 925*e*, following the "Yes" branch, selecting a certain factor that characterizes the event which, based on a second model of the user, has an effect on the user that is congruous with the predicted affective response. Optionally, the second model is the model 912. Optionally, the selection is done utilizing the event analyzer module 914.

And in Step 925*f*, responsive to a determination in Step 925*c* that the predicted affective response indicates the state of emotional imbalance of the user, notifying the user about the certain factor. Optionally, notifying the user in this step is done utilizing the awareness module 916, as described above.

It is to be noted that in some embodiments, Step 925*e* may be performed even if the determination made in Step 925*d* indicates that the predicted affective response does not indicate a state of emotional imbalance of the user. Optionally, Step 925*e* may still be performed as part of collection and analysis of data related to events involving the user (e.g., by a software agent operating on behalf of the user).

In some embodiments, the method optionally includes an additional Step 925*a* that involves receiving a prior measurement of affective response of the user, which is taken with the sensor 102 before computing the predicted affective response in Step 925*c*, and utilizing the prior measurement for the determining of whether the affective response corresponding to the event is indicative of the user transitioning to the state of emotional imbalance. For example, a determination in Step 925*d* that indicates that the predicted affective response indicates a state of emotional imbalance of the user may be based on the fact that the prior measurement received in Step 925*a* has a value that is below a threshold, while the predicted affective response has a value that is above the threshold.

Reaching a determination that the predicted affective response indicates that the user is predicted to be in the state of emotional imbalance may done in different ways. In one embodiment, making the determination is done based on the predicted affective response indicating that an extent, to which the user felt a certain emotion, reaches a first threshold. Optionally, the certain emotion is at least one of the following emotions: anger, contempt, disgust, distress, and fear. In another embodiment, making the determination is done based on the predicted affective response indicating that a level of stress felt by the user reaches a second threshold.

Given that in some embodiments, not all predictions of affective response of a user will be indicative of a state of emotional imbalance of the user, the user might not be notified about a certain factor corresponding to each event (e.g., in Step 925*f* described above). In these embodiments, a first predicted affective response corresponding to a first event may be indicative of emotional imbalance, while a second predicted affective response corresponding to a second event may not. Consequently, the user may be notified about a first factor that characterizes the first event and is congruous with the first predicted affective response, but may not be notified above a second factor that characterizes the second event and is congruous with the second predicted affective response. Such a different behavior with respect to the first and second predictions of affective response may involve performing different operations, as described in the following embodiment.

In one embodiment, a method for warning a user about a cause of imminent emotional imbalance includes at least the following steps:

In Step 1, receiving, by a system comprising a processor and memory, a first description indicative of a first set of factors that characterize a first event that involves the user having a first experience. Optionally, each of the factors in the first set corresponds to at least one of the following: the user, the first experience, and the instantiation of the first event.

In Step 2, computing, from a first input that is based on the first description and utilizing a first model of the user, a first predicted affective response corresponding to the event. Optionally, the first input includes feature values generated by the feature generator 706 based on the first description. Optionally, computing the first predicted affective response is done utilizing the ERP 731.

In Step 3, determining that the first predicted affective response corresponding to the first event indicates a state of emotional imbalance of the user. Optionally, this step utilizes the emotional state analyzer module 910.

In Step 4, selecting a first factor, from among the first set, which, based on a second model of the user, has an effect on the user that is congruous with the first predicted affective response. Optionally, the first factor is selected utilizing the event analyzer module 914.

In Step 5, notifying the user about the first factor. Optionally, notifying the user is done utilizing the awareness module 916.

In Step 6, receiving a second description indicative of a second set of factors that characterize a second event that involves the user having a second experience. Optionally, the first experience is different from the second experience. Alternatively, the first and second events may involve having the same experience. Optionally, each of the factors in the second set corresponds to at least one of the following: the user, the second experience, and the instantiation of the second event.

In Step 7, computing, from a second input that is based on the second description and utilizing the first model of the user, a second predicted affective response corresponding to the second event. Optionally, the second input includes feature values generated by the feature generator 706 based on the second description. Optionally, computing the second predicted affective response is done utilizing the ERP 731.

In Step 8, determining that the second predicted affective response corresponding to the second event does not indicate the state of emotional imbalance of the user. Optionally, this step utilizes the emotional state analyzer module 910.

And in Step 9, refraining from notifying the user about a second factor, which belongs to the second set, and which, based on the second model of the user, is congruous with the second predicted affective response.

Figure 7:
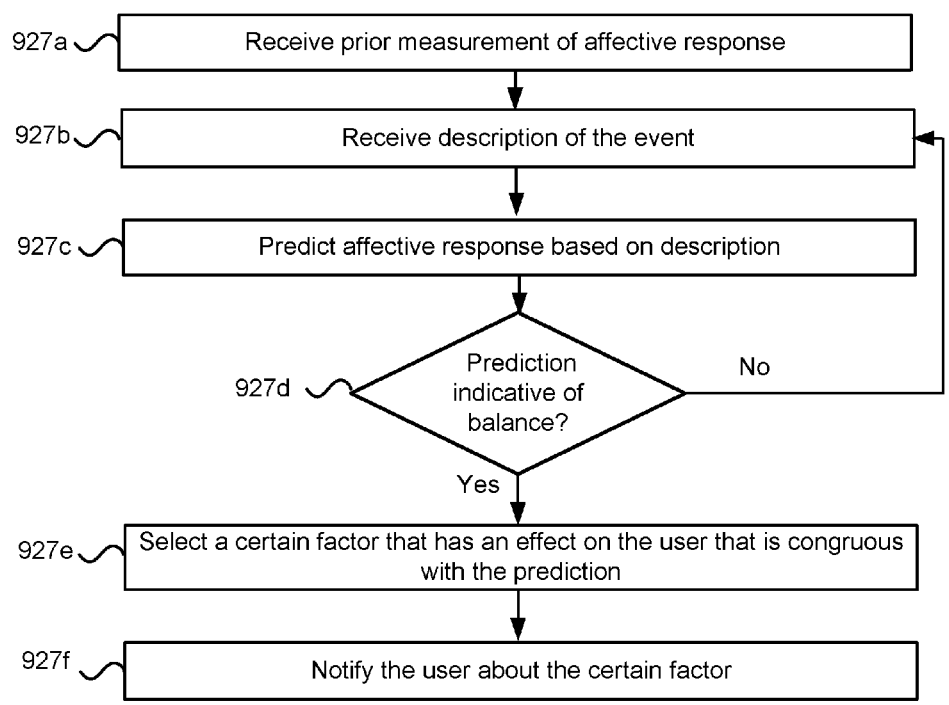
FIG. 7 illustrates steps involved in one embodiment of a method for notifying a user about a cause that will contribute to emotional balance.

FIG. 7 illustrates steps involved in one embodiment of a method for notifying a user about a cause that will (likely) contribute to emotional balance. The steps illustrated in FIG. 7 may be used, in some embodiments, by systems modeled according to FIG. 5.

In one embodiment, the method for notifying a user about a cause that will likely contribute to emotional balance includes at least the following steps:

In Step 927*b*, receiving, by a system comprising a processor and memory, a description indicative of factors characterizing an event that involves the user having an experience. Optionally, each of the factors corresponds to at least one of the following: the user, the experience, and the instantiation of the event. Optionally, the description is generated by the event annotator 701.

In Step 927*c*, computing, from an input based on the description and utilizing a first model of the user, a predicted affective response corresponding to the event. Optionally, the first model is the model 912. Optionally, computing the predicted affective response is done utilizing the ERP 731.

In Step 927*d*, determining whether the predicted affective response computed in Step 927*c* indicates a state of emotional balance of the user. Optionally, the determining is done by the emotional state analyzer module 910. Optionally, upon determining that the predicted affective response does not indicate a state of emotional balance, the method terminates. Alternatively, in some embodiments, upon determining that the predicted affective response does not indicate a state of emotional balance, the method may involve returning to Step 927*b*, in order to receive additional descriptions (this option is illustrated as the "No" branch).

In Step 927*e*, following the "Yes" branch, selecting a certain factor that characterizes the event which, based on a second model of the user, has an effect on the user that is congruous with the predicted affective response. Optionally, the second model is the model 912. Optionally, the selection is done utilizing the event analyzer module 914.

And in Step 927*f*, responsive to a determination in Step 927*c* that the predicted affective response indicates the state of emotional balance of the user, notifying the user about the certain factor. Optionally, notifying the user in this step is done utilizing the awareness module 916, as described above.

It is to be noted that in some embodiments, Step 927*e* may be performed even if the determination made in Step 927*d* indicates that the predicted affective response does not indicate a state of emotional balance of the user. Optionally, Step 927*e* may still be performed as part of collection and analysis of data related to events involving the user (e.g., by a software agent operating on behalf of the user).

In some embodiments, the method optionally includes an additional Step 927*a* that involves receiving a prior measurement of affective response of the user, which is taken with the sensor 102 before computing the predicted affective response in Step 927*c*, and utilizing the prior measurement for the determining of whether the affective response corresponding to the event is indicative of the user transitioning to the state of emotional balance. For example, a determination in Step 927*d* that indicates that the predicted affective response indicates a state of emotional balance of the user may be based on the fact that the prior measurement received in Step 927a has a value that is below a threshold, while the predicted affective response has a value that is above the threshold.

Reaching a determination that the predicted affective response indicates that the user is predicted to be in the state of emotional balance may done in different ways. In one embodiment, making the determination is done based on the predicted affective response indicating that an extent, to which the user felt a certain emotion, reaches a first threshold. Optionally, the certain emotion is at least one of the following emotions: happiness, and contentment. In another embodiment, making the determination is done based on the predicted affective response indicating that a level of stress felt by the user does not reach a second threshold.

Given that in some embodiments, not all predictions of affective response of a user will be indicative of a state of emotional balance of the user, the user might not be notified about a certain factor corresponding to each event (e.g., in Step 927f described above). In these embodiments, a first predicted affective response corresponding to a first event may be indicative of emotional balance, while a second predicted affective response corresponding to a second event may not. Consequently, the user may be notified about a first factor that characterizes the first event and is congruous with the first predicted affective response, but may not be notified above a second factor that characterizes the second event and is congruous with the second predicted affective response. Such a different behavior with respect to the first and second predictions of affective response may involve performing different operations, as described in the following embodiment.

In one embodiment, a method for notifying a user about a cause that will contributed to emotional balance includes at least the following steps:

In Step 1, receiving, by a system comprising a processor and memory, a first description indicative of a first set of factors that characterize a first event that involves the user having a first experience. Optionally, each of the factors in the first set corresponds to at least one of the following: the user, the first experience, and the instantiation of the first event.

In Step 2, computing, from a first input that is based on the first description and utilizing a first model of the user, a first predicted affective response corresponding to the event. Optionally, the first input includes feature values generated by the feature generator 706 based on the first description. Optionally, computing the first predicted affective response is done utilizing the ERP 731.

In Step 3, determining that the first predicted affective response corresponding to the first event indicates a state of emotional balance of the user. Optionally, this step utilizes the emotional state analyzer module 910.

In Step 4, selecting a first factor, from among the first set, which, based on a second model of the user, has an effect on the user that is congruous with the first predicted affective response. Optionally, the first factor is selected utilizing the event analyzer module 914.

In Step 5, notifying the user about the first factor. Optionally, notifying the user is done utilizing the awareness module 916.

In Step 6, receiving a second description indicative of a second set of factors that characterize a second event that involves the user having a second experience. Optionally, the first experience is different from the second experience. Alternatively, the first and second events may involve having the same experience. Optionally, each of the factors in the second set corresponds to at least one of the following: the user, the second experience, and the instantiation of the second event.

In Step 7, computing, from a second input that is based on the second description and utilizing the first model of the user, a second predicted affective response corresponding to the second event. Optionally, the second input includes feature values generated by the feature generator 706 based on the second description. Optionally, computing the second predicted affective response is done utilizing the ERP 731.

In Step 8, determining that the second predicted affective response corresponding to the second event does not indicate the state of emotional balance of the user. Optionally, this step utilizes the emotional state analyzer module 910.

And in Step 9, refraining from notifying the user about a second factor, which belongs to the second set, and which, based on the second model of the user, is congruous with the second predicted affective response.

Sensors

Following is a discussion regarding sensors, additional details about sensors may be found in section 1 (Sensors), in the patent application U.S. Ser. No. 15/184,401. As used herein, a sensor is a device that detects and/or responds to some type of input from the physical environment. Herein, "physical environment" is a term that includes the human body and its surroundings. An example of a sensor, which may be one of the various sensors discussed below, is the sensor 102.

In some embodiments, a sensor that is used to measure affective response of a user may include, without limitation, one or more of the following: a device that measures a physiological signal of the user, an image-capturing device (e.g., a visible light camera, a near infrared (NIR) camera, a thermal camera (useful for measuring wavelengths larger than 2500 nm), a microphone used to capture sound, a movement sensor, a pressure sensor, a magnetic sensor, an electro-optical sensor, and/or a biochemical sensor. When a sensor is used to measure the user, the input from the physical environment detected by the sensor typically originates and/or involves the user. For example, a measurement of affective response of a user taken with an image capturing device comprises an image of the user. In another example, a measurement of affective response of a user obtained with a movement sensor typically detects a movement of the user. In yet another example, a measurement of affective response of a user taken with a biochemical sensor may measure a concentration of chemicals in the user (e.g., nutrients in blood) and/or by-products of chemical processes in the body of the user (e.g., a composition of the user's breath).

Sensors used in embodiments described herein to measure affective response of a user may have different relationships to the body of the user. In one example, a sensor used to measure affective response of a user may include an element that is attached to the user's body (e.g., the sensor may be embedded in gadget in contact with the body and/or a gadget held by the user, the sensor may comprise an electrode in contact with the body, and/or the sensor may be embedded in a film or stamp that is adhesively attached to the body of the user). In another example, the sensor may be embedded in, and/or attached to, an item worn by the user, such as a glove, a shirt, a shoe, a bracelet, a ring, a head-mounted display, and/or helmet or other form of headwear. In yet another example, the sensor may be implanted in the user's body, such a chip or other form of implant that measures the concentration of certain chemicals, and/or monitors various physiological processes in the body of the user. And in still another example, the sensor may be a device that is remote of the user's body (e.g., a camera or microphone).

As used herein, a "sensor" may refer to a whole structure housing a device used for detecting and/or responding to some type of input from the physical environment, or to one or more of the elements comprised in the whole structure. For example, when the sensor is a camera, the word sensor may refer to the entire structure of the camera, or just to its CMOS detector.

In some embodiments, a sensor may store data it collects and/or processes (e.g., in electronic memory). Additionally or alternatively, the sensor may transmit data it collects and/or processes. Optionally, to transmit data, the sensor may use various forms of wired communication and/or wireless communication, such as Wi-Fi signals, Bluetooth, cellphone signals, and/or near-field communication (NFC) radio signals.

In some embodiments, a measurement of affective response of a user comprises, and/or is based on, a physiological signal of the user, which reflects a physiological state of the user. Following are some non-limiting examples of physiological signals that may be measured. Some of the example below include types of techniques and/or sensors that may be used to measure the signals; those skilled in the art will be familiar with various sensors, devices, and/or methods that may be used to measure these signals:

(A) Heart Rate (HR), Heart Rate Variability (HRV), and Blood-Volume Pulse (BVP), and/or other parameters relating to blood flow, which may be determined by various means such as electrocardiogram (ECG), photoplethysmogram (PPG), and/or impedance cardiography (ICG).

(B) Skin conductance (SC), which may be measured via sensors for Galvanic Skin Response (GSR), which may also be referred to as Electrodermal Activity (EDA).

(C) Skin Temperature (ST) may be measured, for example, with various types of thermometers.

(D) Brain activity and/or brainwave patterns, which may be measured with electroencephalography (EEG). Additional discussion about EEG is provided below.

(E) Brain activity determined based on functional magnetic resonance imaging (fMRI).

(F) Brain activity based on Magnetoencephalography (MEG).

(G) Muscle activity, which may be determined via electrical signals indicative of activity of muscles, e.g., measured with electromyography (EMG). In one example, surface electromyography (sEMG) may be used to measure muscle activity of frontalis and corrugator supercilii muscles, indicative of eyebrow movement, and from which an emotional state may be recognized.

(H) Eye movement, e.g., measured with electrooculography (EOG).

(I) Blood oxygen levels that may be measured using hemoencephalography (HEG).

(J) $CO_2$ levels in the respiratory gases that may be measured using capnography.

(K) Concentration of various volatile compounds emitted from the human body (referred to as the Volatome), which may be detected from the analysis of exhaled respiratory gasses and/or secretions through the skin using various detection tools that utilize nanosensors.

(L) Temperature of various regions of the body and/or face may be determined utilizing thermal Infra-Red (IR) cameras. For example, thermal measurements of the nose and/or its surrounding region may be utilized to estimate physiological signals such as respiratory rate and/or occurrence of allergic reactions.

In some embodiments, a measurement of affective response of a user comprises, and/or is based on, a behavioral cue of the user. A behavioral cue of the user is obtained by monitoring the user in order to detect things such as facial expressions of the user, gestures made by the user, tone of voice, and/or other movements of the user's body (e.g., fidgeting, twitching, or shaking). The behavioral cues may be measured utilizing various types of sensors. Some non-limiting examples include an image capturing device (e.g., a camera), a movement sensor, a microphone, an accelerometer, a magnetic sensor, and/or a pressure sensor. In one example, a behavioral cue may involve prosodic features of a user's speech such as pitch, volume, tempo, tone, and/or stress (e.g., stressing of certain syllables), which may be indicative of the emotional state of the user. In another example, a behavioral cue may be the frequency of movement of a body (e.g., due to shifting and changing posture when sitting, laying down, or standing). In this example, a sensor embedded in a device such as accelerometers in a smartphone or smartwatch may be used to take the measurement of the behavioral cue.

In some embodiments, a measurement of affective response of a user may be obtained by capturing one or more images of the user with an image-capturing device, such as a camera. Optionally, the one or more images of the user are captured with an active image-capturing device that transmits electromagnetic radiation (such as radio waves, millimeter waves, or near visible waves) and receives reflections of the transmitted radiation from the user. Optionally, the one or more captured images are in two dimensions and/or in three dimensions. Optionally, the one or more captured images comprise one or more of the following: a single image, sequences of images, a video clip. In one example, images of a user captured by the image capturing device may be utilized to determine the facial expression and/or the posture of the user. In another example, images of a user captured by the image capturing device depict an eye of the user. Optionally, analysis of the images can reveal the direction of the gaze of the user and/or the size of the pupils. Such images may be used for eye tracking applications, such as identifying what the user is paying attention to, and/or for determining the user's emotions (e.g., what intentions the user likely has). Additionally, gaze patterns, which may involve information indicative of directions of a user's gaze, the time a user spends gazing at fixed points, and/or frequency at which the user changes points of interest, may provide information that may be utilized to determine the emotional response of the user.

EEG is a common method for recording brain signals in humans because it is safe, affordable, and easy to use; it also has a high temporal resolution (of the order of milliseconds). EEG electrodes, placed on the scalp, can be either "passive" or "active". Passive electrodes, which are metallic, are connected to an amplifier, e.g., by a cable. Active electrodes may have an inbuilt preamplifier to make them less sensitive to environmental noise and cable movements. Some types of electrodes may need gel or saline liquid to operate, in order to reduce the skin-electrode contact impedance. While other types of EEG electrodes can operate without a gel or saline and are considered "dry electrodes". There are various brain activity patterns that may be measured by EEG. Some of the popular ones often used in affective computing include: Event Related Desynchronization/Synchronization, Event Related Potentials (e.g., P300 wave and error potentials), and Steady State Evoked Potentials. Measurements of EEG electrodes are typically subjected to various feature extraction techniques which aim to represent raw or preprocessed EEG signals by an ideally small number of relevant values, which describe the task-relevant information contained in the signals. For example, these features may be the power of the EEG over selected channels, and specific frequency bands. Various feature extraction techniques are discussed in more detail in Bashashati, et al., "A survey of signal processing algorithms in brain-computer interfaces based on electrical brain signals", in *Journal of Neural Engineering*, 4(2):R32, 2007. Additional discussion about using EEG in affective computing and brain computer interfaces (BCI) can be found in Lotte, et al., "Electroencephalography (EEG)-based Brain Computer Interfaces", in *Wiley Encyclopedia of Electrical and Electronics Engineering*, pp. 44, 2015, and the references cited therein.

The aforementioned examples involving sensors and/or measurements of affective response represent an exemplary sample of possible physiological signals and/or behavioral cues that may be measured. Embodiments described in this disclosure may utilize measurements of additional types of physiological signals and/or behavioral cues, and/or types of measurements taken by sensors, which are not explicitly listed above. Additionally, in some examples given above some of the sensors and/or techniques may be presented in association with certain types of values that may be obtained utilizing those sensors and/or techniques. This is not intended to be limiting description of what those sensors and/or techniques may be used for. In particular, a sensor and/or a technique listed above, which is associated in the examples above with a certain type of value (e.g., a certain type of physiological signal and/or behavioral cue) may be used, in some embodiments, in order to obtain another type of value, not explicitly associated with the sensor and/or technique in the examples given above.

Measurements of Affective Response

In various embodiments, a measurement of affective response of a user comprises, and/or is based on, one or more values acquired with a sensor that measures a physiological signal and/or a behavioral cue of the user.

In some embodiments, an affective response of a user to an event is expressed as absolute values, such as a value of a measurement of an affective response (e.g., a heart rate level, or GSR value), and/or emotional state determined from the measurement (e.g., the value of the emotional state may be indicative of a level of happiness, excitement, and/or contentedness). Alternatively, the affective response of the user may be expressed as relative values, such as a difference between a measurement of an affective response (e.g., a heart rate level, or GSR value) and a baseline value, and/or a change to emotional state (e.g., a change to the level of happiness). Depending on the context, one may understand whether the affective response referred to is an absolute value (e.g., heart rate and/or level of happiness), or a relative value (e.g., change to heart rate and/or change to the level of happiness). For example, if the embodiment describes an additional value to which the measurement may be compared (e.g., a baseline value), then the affective response may be interpreted as a relative value. In another example, if an embodiment does not describe an additional value to which the measurement may be compared, then the affective response may be interpreted as an absolute value. Unless stated otherwise, embodiments described herein that involve measurements of affective response may involve values that are either absolute and/or relative.

As used herein, a "measurement of affective response" is not limited to representing a single value (e.g., scalar); a measurement may comprise multiple values. In one example, a measurement may be a vector of co-ordinates, such as a representation of an emotional state as a point on a multidimensional plane. In another example, a measurement may comprise values of multiple signals taken at a certain time (e.g., heart rate, temperature, and a respiration rate at a certain time). In yet another example, a measurement may include multiple values representing signal levels at different times. Thus, a measurement of affective response may be a time-series, pattern, or a collection of wave functions, which may be used to describe a signal that changes over time, such as brainwaves measured at one or more frequency bands. Thus, a "measurement of affective response" may comprise multiple values, each of which may also be considered a measurement of affective response. Therefore, using the singular term "measurement" does not imply that there is a single value. For example, in some embodiments, a measurement may represent a set of measurements, such as multiple values of heart rate and GSR taken every few minutes during a duration of an hour.

A measurement of affective response may comprise raw values describing a physiological signal and/or behavioral cue of a user. For example, the raw values are the values provided by a sensor used to measure, possibly after minimal processing, as described below. Additionally or alternatively, a measurement of affective response may comprise a product of processing of the raw values. The processing of one or more raw values may involve performing one or more of the following operations: normalization, filtering, feature extraction, image processing, compression, encryption, and/or any other techniques described further in this disclosure, and/or that are known in the art and may be applied to measurement data.

In some embodiments, processing raw values, and/or processing minimally processed values, involves providing the raw values and/or products of the raw values to a module, function, and/or predictor, to produce a value that is referred to herein as an "affective value". As typically used herein, an affective value is a value that describes an extent and/or quality of an affective response. For example, an affective value may be a real value describing how good an affective response is (e.g., on a scale from 1 to 10), or whether a user is attracted to something or repelled by it (e.g., by having a positive value indicate attraction and a negative value indicate repulsion). In some embodiments, the use of the term "affective value" is intended to indicate that certain processing may have been applied to a measurement of affective response. Optionally, the processing is performed by a software agent. Optionally, the software agent has access to a model of the user that is utilized in order to compute the affective value from the measurement. In one example, an affective value may be a prediction of an Emotional State Estimator (ESE) and/or derived from the prediction of the ESE. In some embodiments, measurements of affective response may be represented by affective values.

It is to be noted that, though affective values are typically results of processing measurements, they may be represented by any type of value that a measurement of affective response may be represented by. Thus, an affective value may, in some embodiments, be a value of a heart rate, brainwave activity, skin conductance levels, etc.

In some embodiments, a measurement of affective response may involve a value representing an emotion (also referred to as an "emotional state" or "emotional response"). Emotions and/or emotional responses may be represented in various ways. In some examples, emotions or emotional responses may be predicted based on measurements of affective response, retrieved from a database, and/or annotated by a user (e.g., self-reporting by a user having the emotional response). In one example, self-reporting may involve analyzing communications of the user to determine the user's emotional response. In another example, self-reporting may involve the user entering values (e.g., via a GUI) that describes the emotional state of the user at a certain time and/or the emotional response of the user to a certain event. In the embodiments, there are several ways to represent emotions (which may be used to represent emotional states and emotional responses as well).

In one embodiment, emotions are represented using discrete categories. For example, the categories may include three emotional states: negatively excited, positively excited, and neutral. In another example, the categories may include emotions such as happiness, surprise, anger, fear, disgust, and sadness. In still another example, the emotions may be selected from the following set that includes basic emotions, including a range of positive and negative emotions such as Amusement, Contempt, Contentment, Embarrassment, Excitement, Guilt, Pride in achievement, Relief, Satisfaction, Sensory pleasure, and Shame, as described by Ekman P. (1999), "Basic Emotions", in Dalgleish and Power, *Handbook of Cognition and Emotion*, Chichester, UK: Wiley.

In another embodiment, emotions are represented using a multidimensional representation, which typically characterizes the emotion in terms of a small number of dimensions. In one example, emotional states are represented as points in a two dimensional space of Arousal and Valence. Arousal describes the physical activation, and valence the pleasantness or hedonic value. Each detectable experienced emotion is assumed to fall in a specified region in that two-dimensional space. Other dimensions that are typically used to represent emotions include potency/control (refers to the individual's sense of power or control over the eliciting event), expectation (the degree of anticipating or being taken unaware), and intensity (how far a person is away from a state of pure, cool rationality). The various dimensions used to represent emotions are often correlated. For example, the values of arousal and valence are often correlated, with very few emotional displays being recorded with high arousal and neutral valence. In one example, emotions are represented as points on a circle in a two dimensional space pleasure and arousal, such as the circumplex of emotions. In another example, emotions may be represented as points in a two dimensional space whose axes correspond to positive affect (PA) and negative affect (NA), as described by Watson et al. (1988), "Development and validation of brief measures of positive and negative affect: the PANAS scales", *Journal of Personality and Social Psychology* 54.6: 1063.

In yet another embodiment, emotions are represented using a numerical value that represents the intensity of the emotional state with respect to a specific emotion. For example, a numerical value stating how much the user is enthusiastic, interested, and/or happy. Optionally, the numeric value for the emotional state may be derived from a multidimensional space representation of emotion; for instance, by projecting the multidimensional representation of emotion to the nearest point on a line in the multidimensional space.

Measurement of affective response may be referred to herein as being positive or negative. A positive measurement of affective response, as typically used herein, reflects a positive emotion indicating one or more qualities such as desirability, happiness, content, and the like, on the part of the user of whom the measurement is taken. Similarly, a negative measurement of affective response, as typically used herein, reflects a negative emotion indicating one or more qualities such as repulsion, sadness, anger, and the like on the part of the user of whom the measurement is taken. Optionally, when a measurement is neither positive nor negative, it may be considered neutral.

In some embodiments, whether a measurement is to be considered positive or negative may be determined with reference to a baseline (e.g., a value determined based on previous measurements to a similar situation and/or experience the user may be having). Thus, if the measurement indicates a value that is above the baseline, e.g., happier than the baseline, it may be considered positive, and if lower it may be considered negative).

In some embodiments, when a measurement of affective response is relative, i.e., it represents a change in a level of a physiological signal and/or a behavioral cue of a user, then the direction of the change may be used to determine whether the measurement is positive or negative. Thus, a positive measurement of affective response may correspond to an increase in one or more qualities such as desirability, happiness, content, and the like, on the part of the user of whom the measurement is taken. Similarly, a negative measurement of affective response may correspond to an increase in one or more qualities such as repulsion, sadness, anger, and the like on the part of the user of whom the measurement is taken. Optionally, when a measurement neither changes in a positive direction nor in a negative direction, it may be considered neutral.

Some embodiments may involve a reference to the time at which a measurement of affective response of a user is taken. Depending on the embodiment, this time may have various interpretations. For example, in one embodiment, this time may refer to the time at which one or more values describing a physiological signal and/or behavioral cue of the user were obtained utilizing one or more sensors. Optionally, the time may correspond to one or more periods during which the one or more sensors operated in order to obtain the one or more values describing the physiological signal and/or the behavioral cue of the user. For example, a measurement of affective response may be taken during a single point in time and/or refer to a single point in time (e.g., skin temperature corresponding to a certain time). In another example, a measurement of affective response may be taken during a contiguous stretch of time (e.g., brain activity measured using EEG over a period of one minute). In still another example, a measurement of affective response may be taken during multiple points and/or multiple contiguous stretches of time (e.g., brain activity measured every waking hour for a few minutes each time).

Various embodiments described herein involve measurements of affective response of users to having experiences. A measurement of affective response of a user to having an experience may also be referred to herein as a "measurement of affective response of the user to the experience". In order to reflect the affective response of a user to having an experience, the measurement is typically taken in temporal proximity to when the user had the experience (so the affective response may be determined from the measurement). Herein, temporal proximity means nearness in time. Thus, stating that a measurement of affective response of a user is taken in temporal proximity to when the user has/had an experience means that the measurement is taken while the user has/had the experience and/or shortly after the user finishes having the experience. Optionally, a measurement of affective response of a user taken in temporal proximity to having an experience may involve taking at least some of the measurement shortly before the user started having the experience (e.g., for calibration and/or determining a baseline).

What window in time constitutes being "shortly before" and/or "shortly after" having an experience may vary in embodiments described herein, and may depend on various factors such as the length of the experience, the type of sensor used to acquire the measurement, and/or the type of physiological signal and/or behavioral cue being measured. In one example, with a short experience (e.g., and experience lasting 10 seconds), "shortly before" and/or "shortly after" may mean at most 10 seconds before and/or after the experience; though in some cases it may be longer (e.g., a minute or more). However, with a long experience (e.g., an experience lasting hours or days), "shortly before" and/or "shortly after" may correspond even to a period of up to a few hours before and/or after the experience (or more). In another example, when measuring a signal that is quick to change, such as brainwaves measured with EEG, "shortly before" and/or "shortly after" may correspond to a period of a few seconds or even up to a minute. However, with a signal that changes slower, such as heart rate or skin temperature, "shortly before" and/or "shortly after" may correspond to a longer period such as even up to ten minutes or more. In still another example, what constitutes "shortly after" an experience may depend on the nature of the experience and how long the affective response to it may last. For example, in one embodiment, measuring affective response to a short segment of content (e.g., viewing a short video clip) may comprise heart-rate measurements taken up to 30 seconds after the segment had been viewed. However, in another embodiment, measuring affective response to eating a meal may comprise measurements taken even possibly hours after the meal, to reflect the effects digesting the meal had on the user's physiology.

In some embodiments, determining the affective response of a user to an event may utilize measurement taking during a fraction of the time corresponding to the event. The affective response of the user may be measured by obtaining values of a physiological signal of the user that in some cases may be slow to change, such as skin temperature, and/or slow to return to baseline values, such as heart rate. In such cases, measuring the affective response does not have to involve continually measuring the user throughout the duration of the event. Since such physiological signals are slow to change, reasonably accurate conclusions regarding the affective response of the user to an event may be reached from samples of intermittent measurements taken at certain periods during the event and/or after it. In one example, measuring the affective response of a user to a vacation destination may involve taking measurements during short intervals spaced throughout the user's stay at the destination (and possibly during the hours or days after it), such as taking a GSR measurement lasting a few seconds, every few minutes or hours.

Additional details regarding measurements of affective response, such as how measurements are taken, processed, and/or what they may comprise may be found in section 2 (Measurements of affective response) in the patent application U.S. Ser. No. 15/184,401.

Experiences

Some embodiments described herein may involve users having "experiences". In different embodiments, "experiences" may refer to different things. In some embodiments, there is a need to identify events involving certain experiences, and/or to characterize them. For example, identifying and/or characterizing what experience a user has may be needed in order to describe an event in which a user has the experience. Having such a description is useful for various tasks. In one example, a description of an event may be used to generate a sample provided to a predictor for predicting affective response to the experience. In another example, descriptions of events may be used to group events into sets involving the same experience (e.g., sets of events described further below in this disclosure).

An experience is typically characterized as being of a certain type. Below is a description comprising non-limiting examples of various categories of types of experiences to which experiences in different embodiments may correspond. This description is not intended to be a partitioning of experiences; e.g., various experiences described in embodiments may fall into multiple categories listed below. This description is not comprehensive; e.g., some experiences in embodiments may not belong to any of the categories listed below.

Location—Various embodiments described herein involve experiences in which a user is in a location. In some embodiments, a location may refer to a place in the physical world. A location in the physical world may occupy various areas in, and/or volumes of, the physical world. For example, a location may be a continent, country, region, city, park, or a business (e.g., a restaurant). In one example, a location is a travel destination (e.g., Paris). In another example, a location may be a portion of another location, such as a specific room in a hotel or a seat in a specific location in a theatre. For example, is some embodiments, being in the living room of an apartment may be considered a different experience than being in a bedroom.

Virtual Location—In some embodiments, a location may refer to a virtual environment such as a virtual world, with at least one instantiation of the virtual environment stored in a memory of a computer. Optionally, a user is considered to be in the virtual environment by virtue of having a value stored in the memory indicating the presence of a representation of the user in the virtual environment. Optionally, different locations in virtual environment correspond to different logical spaces in the virtual environment. For example, different rooms in an inn in a virtual world may be considered different locations.

Route—In some embodiments, an experience may involve traversing a certain route. Optionally, a route is a collection of two or more locations that a user may visit. Optionally, at least some of the two or more locations in the route are places in the physical world. Optionally, at least some of the two or more locations in the route are places in a virtual world. In one embodiment, a route is characterized by the order in which the locations are visited. In another embodiment, a route is characterized by a mode of transportation used to traverse it.

Content—Consuming content is considered an experience in some embodiments. Optionally, the content that is consumed is digital content, and consuming it involves a user interface that presents the content (e.g., a display and/or speakers). In some embodiments, an experience involving consuming content is characterized by the type of medium involved in consuming the content. For example, the experience may be referred to as "watching a movie", "surfing the Internet", and/or "listening to music". In other embodiments, an experience involving consuming content is characterized by content itself. For example, the experience may be referred to as "watching Star Trek 3", "browsing Facebook", and/or "listening to Wish You Were Here" by Pink Floyd.

Activity—In some embodiments, an experience may involve an activity that a user does. In one example, an experience involves a recreational activity (e.g., traveling, going out to a restaurant, visiting the mall, or playing games on a gaming console). In another example, an experience involves a day-to-day activity (e.g., getting dressed, driving to work, talking to another person, sleeping, and/or making dinner). In yet another example, an experience involves a work related activity (e.g., writing an email, boxing groceries, or serving food). In still another example, an experience involves a mental activity such as studying and/or taking an exam. And in still another example, an experience may involve a simple action like sneezing, kissing, or coughing.

Social Interaction—In some embodiments, an experience may involve some sort of social interaction a user has. Optionally, the social interaction may be between the user and another person and/or between the user and a software-based entity (e.g., a software agent or physical robot).

Service Provider—In some embodiments, a social interaction a user has is with a service provider providing a service to the user. Optionally, a service provider may be a human service provider or a virtual service provider (e.g., a robot, a chatbot, a web service, and/or a software agent).

Substance—Various embodiments described herein may involve experiences in which a user consumes a substance and/or a combination of substances. Optionally, a substance is something that the user consumes by having it absorbed in the body of the user. In one example, "substances" may refer to various forms of food and drink that are consumed by eating and drinking. In another example, "substances" may refer to various forms of drugs and/or chemicals that may be consumed by swallowing, injecting, inhaling, and/or by absorption through the skin.

Product—Utilizing a product may be considered an experience in some embodiments. A product may be any object that a user may utilize. Examples of products include appliances, clothing items, footwear, wearable devices, gadgets, jewelry, cosmetics, cleaning products, vehicles, sporting gear and musical instruments.

Environment—Spending time in an environment characterized with certain environmental conditions may also constitute an experience in some embodiments. Optionally, different environmental conditions may be characterized by a certain value or range of values of an environmental parameter. In one example, being in an environment in which the temperature is within a certain range corresponds to a certain experience (e.g., being in temperatures lower than 45° F. may be considered an experience of being in the cold and being in temperatures higher than 90° F. may be considered being in a warm environment). In another example, environments may be characterized by a certain range of humidity, a certain altitude, a certain level of pressure (e.g., expressed in atmospheres), and/or a certain level of felt gravity (e.g., a zero-G environment).

In different embodiments described herein, measurements of affective response of users are utilized in computations involving experiences, such as scoring experiences, ranking experiences, comparing experiences, and/or computing time-dependent trends for experiences. Optionally, the experiences involved in such computations all belong to a set of experiences that includes certain types of experiences. Additionally, in embodiments, there may be one or more types of experiences that are explicitly excluded from the set of experiences, and thus measurements of affective response users utilized in the computations do not include measurements of users corresponding to events involving experiences of the one or more types of experiences.

Events

When a user has an experience, this defines an "event". An event may be characterized according to certain attributes. For example, every event may have a corresponding experience and a corresponding user (who had the corresponding experience). An event may have additional corresponding attributes that describe the specific instantiation of the event in which the user had the experience. Examples of such attributes may include the event's duration (how long the user had the experience in that instantiation), the event's starting and/or ending time, and/or the event's location (where the user had the experience in that instantiation). In some embodiments, an event may have a corresponding measurement of affective response, which is a measurement of the user corresponding to the event, to having the experience corresponding to the event.

An event may be referred to as being an "instantiation" of an experience and the time during which an instantiation of an event takes place may be referred to herein as the "instantiation period" of the event. This relationship between an experience and an event may be considered somewhat conceptually similar to the relationship in programming between a class and an object that is an instantiation of the class. The experience may correspond to some general attributes (that are typically shared by all events that are instantiations of the experience), while each event may have attributes that correspond to its specific instantiation (e.g., a certain user who had the experience, a certain time the experience was experienced, a certain location the certain user had the experience, etc.) Therefore, when the same user has the same experience but at different times, these may be considered different events (with different instantiations periods). For example, a user eating breakfast on Sunday, Feb. 1, 2015 is a different event than the user eating breakfast on Monday, Feb. 2, 2015.

An event may be denoted in this disclosure with the letter $\tau$. An event involving a user u corresponding to the event who has an experience e corresponding to the event, may be represented by a tuple $\tau=(u,e)$. Similarly, an event $\tau$ may have a corresponding measurement of affective response m which is a measurement of the user u corresponding to the event to having the experience e corresponding to the event (as taken during the instantiation period of the event or shortly after it). In this case, the event $\tau$ may be represented by a tuple $\tau=(u,e,m)$. It is to be noted that the same user may have the same experience at multiple different times. These may be represented by multiple different events having possibly different measurement values. For example, two different events in which the same user had the same experience, but with possibly different corresponding measurements of affective response may be denoted herein as events $\tau_1=(u,e,m_1)$ and $\tau_2=\tau_2(u,e,m_2)$. In some cases herein, to emphasize that a measurement m corresponds to an event $\tau$, the measurement will be denoted $m_\tau$. Similarly, the user corresponding to an event $\tau$ may be denoted $u_\tau$ and the experience corresponding to $\tau$ may be denoted $e_\tau$.

In some embodiments, a tuple $\tau$ may correspond to additional information related to the specific instantiation of the event, such as a time $\tau$ of the event (e.g., the time the measurement m is taken), in which case, the tuple may be of the form $\tau=(u,e,m,t)$. Additionally or alternatively, a tuple $\tau$ may further correspond to a weight parameter w, which may represent the importance of the measurement and be indicative of the weight the measurement should be given when training models. In this case, the tuple may be of the form $\tau=(u,e,m,w)$. Additionally or alternatively, a tuple $\tau$ may correspond to other factors related to the user (e.g., demographic characteristics) or the instantiation of the experience (e.g., duration and/or location of the event corresponding to the measurement).

Descriptions of events are used in various embodiments in this disclosure. Typically, a description of an event may include values related to a user corresponding to the event, an experience corresponding to the event, and/or details of the instantiation of the event (e.g., the duration, time, location, and/or conditions of the specific instantiation of the event). Optionally, a description of an event may be represented as feature vector comprising feature values. Additionally or alternatively, a description of an event may include various forms of data such as images, audio, video, transaction records, and/or other forms of data that describe aspects of the user corresponding to the event, the experience corresponding to the event, and/or the instantiation of the event. Additionally, in some embodiments, a description of an event includes, and/or may be used to derive, factors of events (discussed elsewhere in this disclosure).

A description of a user includes values describing aspects of the user. Optionally, the description may be represented as a vector of feature values. Additionally or alternatively, a description of a user may include data such as images, audio, and/or video that includes the user. In some embodiments, a description of a user contains values that relate to general attributes of the user, which are often essentially the same for different events corresponding to the same user, possibly when having different experiences. Examples of such attributes may include demographic information about the user (e.g., age, education, residence, etc.). Additionally or alternatively, the description may include portions of a profile of the user. The profile may describe various details of experiences the user had, such as details of places in the real world or virtual worlds the user visited, details about activities the user participated in, and/or details about content the user consumed. Optionally, the description of the user may include values obtained from modeling the user, such as bias values corresponding to biases the user has.

A description of an experience includes values describing aspects of the experience. Optionally, the description of the experience may be represented as a vector of feature values. Typically, the description of the experience contains values that relate to general attributes of the experience, which are often essentially the same for different events corresponding to the same experience, possibly even when it is experienced at different times and/or by different users. Examples of such information may include attributes related to the type of experience, such as its typical location, cost, difficulty, etc.

The description of an event $\tau$ may include feature values obtained from a description of the user corresponding to the event $\tau$ and/or a description of the experience corresponding to the event $\tau$. Additionally, the description of the event $\tau$ may include values that may vary between different events corresponding to the same experience as $\tau$. These values include values corresponding to the instantiation of the event $\tau$ during the specific time corresponding to $\tau$, when the user u had the experience e. Examples of such values may include the location corresponding to $\tau$ (where the user u had the experience e in the specific instantiation $\tau$), the duration corresponding to $\tau$ (how long the user u had the experience e in the specific instantiation $\tau$), and/or the time frame of $\tau$ (e.g., when $\tau$ started and/or ended). Optionally, the description of the event $\tau$ may include values related to situations the user was in during the time frame of $\tau$ (e.g., the user's mood, alertness, credit status, relationship status, and other factors that may influence the user's state of mind). Optionally, the description of $\tau$ may include values related to experiences the user had, such as the size of portion the user was served, the noise and/or cleanliness level in the user's room, how long it took to deliver a product to the user, and/or other attributes that may differ depending on the embodiment being considered.

Various embodiments described herein involve collecting measurements of affective response of users to experiences (i.e., collecting measurements corresponding to events). Though in some embodiments it may be easy to determine who the users corresponding to the events are (e.g., via knowledge of which sensors, devices, and/or software agents provide the data), it may not always be easy to determine what are the corresponding experiences the users had. Thus, in some embodiments, it is necessary to identify the experiences users have and to be able to associate measurements of affective response of the users with respective experiences to define events. However, this may not always be easily done. In one example, it may not be clear to a system that monitors a user (e.g., a software agent) when the user has an experience and/or what the experience is. In another example, the identity of a user who has an experience may not be known (e.g., by a provider of an experience), and thus, it may be necessary to identify the user too. In general, determining who the user corresponding to an event and/or the experience corresponding to an event are referred to herein as identifying the event.

Identifying an event may also involve, in some embodiments, identifying details describing aspects of the event. Thus, the term "identifying an event" may also refer to determining one or more details related to an event, and as such, in some embodiments, "identifying an event" may be interpreted as "describing an event", and may be used with that term interchangeably. In one example, the one or more details may relate to the user corresponding to the event. In another example, the one or more details may relate to the experience corresponding to the event. And in yet another example, the one or more details may relate to the instantiation of the event. Optionally, the one or more details related to the event may be factors of the event, and/or may comprise values from which factors of the event are derived.

In some embodiments, events are identified by a module referred to herein as an event annotator. Optionally, an event annotator is a predictor, and/or utilizes a predictor, to identify events. Optionally, the event annotator generates a description of an event, which may be used for various purposes such as assigning factors to an event.

Events can have multiple measurements associated with them that are taken during various times. For example, a measurement corresponding to an event may comprise, and/or be based on, values measured when the user corresponding to the event starts having the experience corresponding to the event, throughout the period during which the user has the experience, and possibly sometime after having the experience. In another example, the measurement may be based on values measured before the user starts having the experience (e.g., in order to measure effects of anticipation and/or in order to establish a baseline value based on the measurement taken before the start).

In some embodiments, measurements of affective response corresponding to an event, which are taken at different times and/or are based on values measured by sensors over different time frames, may be used to capture different aspects of the event. For example, when considering an event involving eating a meal, the event may have various corresponding measurements capturing different aspects of the experience of having the meal. A measurement of affective response based on values acquired while the meal is being brought to the table and before a user starts eating may capture an affective response to how the food looks, how it smells, and/or the size of the portion. A measurement of affective response based on values acquired while the user is eating may be associated with how the food tastes, its texture, etc. And a measurement of affective response based on values acquired after the user is done eating may express how the meal influences the body of the user (e.g., how it is digested, whether it causes the user to be lethargic or energetic, etc.).

In some embodiments, an event annotator, such as the event annotator 701, is used to identify an event, such as determining who the user corresponding to the event is, what experience the user had, and/or certain details regarding the instantiation of the event. Optionally, the event annotator generates a description of the event.

Identifying events may involve utilizing information of one or more of various types of information and/or from one or more of various sources of information, as described below. This information may be used to provide context that can help identify at least one of the following: the user corresponding to the event, the experience corresponding to the event, and/or other properties corresponding to the event (e.g., characteristics of the instantiation of the experience involved in the event and/or situations of the user that are relevant to the event). Optionally, at least some of the information is collected by a software agent that monitors a user on behalf of whom it operates. Optionally, at least some of the information is collected by a software agent that operates on behalf of an entity that is not the user corresponding to the event, such as a software agent of another user that shares the experience corresponding to the event with the user, is in the vicinity of the user corresponding to the event when the user has the experience corresponding to the event, and/or is in communication with the user corresponding to the event. Optionally, at least some of the information is collected by providers of experiences. Optionally, at least some of the information is collected by third parties that monitor the user corresponding to the event and/or the environment corresponding to the event.

Following are some examples of information types and/or information sources that may be used to identify events: Location information (e.g., data about a location a user is in and/or data about the change in location of the user), Images and other sensor information (e.g., images and/or sensor measurements taken from a device of a user such as a smartphone or a wearable device such as a smartwatch or a head-mounted augmented or virtual reality glasses), Measurements of the Environment, Information about and/or from objects and/or devices with the user, Communications of the user, a user's calendar and/or schedule, a user's account (e.g., digital wallets, bank accounts, or social media accounts), information from robotic helpers/servers, and/or information from experience providers.

To determine what events users have, and in particular what are the experiences corresponding to events, some embodiments may involve one or more event annotators to perform this task. In one embodiment, an event annotator receives information of one or more of the types or sources described above. For example, this information may include information about the location, time, movement patterns, measurements of affective response of a user, measurements of the environment, objects in the vicinity of a user, communications of a user, calendar entries of a user, account information of a user, and/or information obtained from a software agent and/or robotic server. Optionally, the information is analyzed and used to generate a sample comprising a vector of feature values that may describe an event. Optionally, the feature values describe characteristics of the user corresponding to the event and/or identify the user corresponding to the event. Optionally, the feature values describe characteristics of the experience corresponding to the event (e.g., describe characteristics determined from the information received by the event annotator), but do not explicitly identify the experience corresponding to the event. Optionally, the sample describes details of the event concerning aspects of the instantiation of the experience corresponding to the event, such as the location, duration, and/or other conditions in which the user corresponding to the event was in while having the experience corresponding to the event.

The term "feature values" is typically used herein to represent data that may be provided to a machine learning-based predictor. Thus, a description of an event may be converted to feature values in order to be used to identify events, as described in this section. Typically, but necessarily, feature values may be data that can be represented as a vector of numerical values (e.g., integer or real values), with each position in the vector corresponding to a certain feature. However, in some embodiments, feature values may include other types of data, such as text, images, and/or other digitally stored information.

In some embodiments, the event annotator 701 utilizes the sources of information mentioned above in order to identify events users have (e.g., identify the type of experience). Additionally or alternatively, the event annotator 701 may be utilized to identify aspects of events, referred to herein as "factors of events". Each of these aspects may relate to the user corresponding to the event, the experience corresponding to the event, and/or the instantiation of the event. It is to be noted that the feature values mentioned in this section, which may be utilized to identify events, may themselves be factors of events and/or derived from factors of events (e.g., when factors of events appear in a description of an event).

Given an unlabeled sample, the event annotator may assign the unlabeled sample one or more corresponding labels, each label identifying an experience the user had. Optionally, the event annotator may provide values corresponding to the confidence and/or probability that the user had the experiences identified by at least some of the one or more labels.

Additional discussion regarding events and information that may be used to identify events may be found in section 4 (Events) and section 5 (Identifying events) in the patent application U.S. Ser. No. 15/184,401.

Predictors and Emotional State Estimators

In some embodiments, a module that receives a query that includes a sample (e.g., a vector including one or more feature values) and computes a label for that sample (e.g., a class identifier or a numerical value), is referred to as a "predictor" and/or an "estimator". Optionally, a predictor and/or estimator may utilize a model to assign labels to samples. In some embodiments, a model used by a predictor and/or estimator is trained utilizing a machine learning-based training algorithm. Optionally, when a predictor and/or or estimator return a label that corresponds to one or more classes that are assigned to the sample, these modules may be referred to as "classifiers".

The terms "predictor" and "estimator" may be used interchangeably in this disclosure. Thus, a module that is referred to as a "predictor" may receive the same type of inputs as a module that is called an "estimator", it may utilize the same type of machine learning-trained model, and/or produce the same type of output. However, as commonly used in this disclosure, the input to an estimator typically includes values that come from measurements, while a predictor may receive samples with arbitrary types of input. For example, a module that identifies what type of emotional state a user was likely in based on measurements of affective response of the user, is referred to herein as an Emotional State Estimator (ESE), while a module that predicts the likely emotional response of a user to an event is referred to herein as an Emotional Response Predictor (ERP). An example of the ERP discussed below may be the ERP 731 which is comprised in some embodiments described in this disclosure. Additionally, a model utilized by an ESE and/or an ERP may be referred to as an "emotional state model" and/or an "emotional response model".

A sample provided to a predictor and/or an estimator in order to receive a label for it may be referred to as a "query sample" or simply a "sample". A value returned by the predictor and/or estimator, which it computed from a sample given to it as an input, may be referred to herein as a "label", a "predicted value", and/or an "estimated value". A pair that includes a sample and a corresponding label may be referred to as a "labeled sample". A sample that is used for the purpose of training a predictor and/or estimator may be referred to as a "training sample" or simply a "sample". Similarly, a sample that is used for the purpose of testing a predictor and/or estimator may be referred to as a "testing sample" or simply a "sample". In typical embodiments, samples used by the same predictor and/or estimator for various purposes (e.g., training, testing, and/or a query) are assumed to have a similar structure (e.g., similar dimensionality) and are assumed to be generated in a similar process (e.g., they undergo the same type of preprocessing).

In some embodiments, a sample for a predictor and/or estimator includes one or more feature values. Optionally, at least some of the feature values are numerical values (e.g., integer and/or real values). Optionally, at least some of the feature values may be categorical values that may be represented as numerical values (e.g., via indices for different categories). Optionally, the one or more feature values comprised in a sample may be represented as a vector of values. Various preprocessing, processing, and/or feature extraction techniques known in the art may be used to generate the one or more feature values comprised in a sample. Additionally, in some embodiments, samples may contain noisy or missing values. There are various methods known in the art that may be used to address such cases.

In some embodiments, a label that is a value returned by a predictor and/or an estimator in response to receiving a query sample, may include one or more types of values. For example, a label may include a discrete categorical value (e.g., a category), a numerical value (e.g., a real number), a set of categories and/or numerical values, and/or a multidimensional value (e.g., a point in multidimensional space, a database record, and/or another sample).

Predictors and estimators may utilize, in various embodiments, different types of models in order to compute labels for query samples. A plethora of machine learning algorithms is available for training different types of models that can be used for this purpose. Some of the algorithmic approaches that may be used for creating a predictor and/or estimator include classification, clustering, function prediction, regression, and/or density estimation. Those skilled in the art can select the appropriate type of model and/or training algorithm depending on the characteristics of the training data (e.g., its dimensionality or the number of samples), and/or the type of value used as labels (e.g., a discrete value, a real value, or a multidimensional value).

In some embodiments, predictors and/or estimators may be described as including and/or utilizing models. A model that is included in a predictor and/or an estimator, and/or utilized by a predictor and/or an estimator, may include parameters used by the predictor and/or estimator to compute a label. Non-limiting examples of such parameters include: support vectors (e.g., used by an SVM), points in a multidimensional space (e.g., used by a Nearest-Neighbor predictor), regression coefficients, distribution parameters (e.g., used by a graphical model), topology parameters, and/or weight parameters (e.g., used by a neural network). When a model contains parameters that are used to compute a label, such as in the examples above, the terms "model", "predictor", and/or "estimator" (and derivatives thereof) may at times be used interchangeably herein. Thus, for example, language reciting "a model that predicts" or "a model used for estimating" is acceptable. Additionally, phrases such as "training a predictor" and the like may be interpreted as training a model utilized by the predictor. Furthermore, when a discussion relates to parameters of a predictor and/or an estimator, this may be interpreted as relating to parameters of a model used by the predictor and/or estimator.

The type and quantity of training data used to train a model utilized by a predictor and/or estimator can have a dramatic influence on the quality of the results they produce. Generally speaking, the more data available for training a model, and the more the training samples are similar to the samples on which the predictor and/or estimator will be used (also referred to as test samples), the more accurate the results for the test samples are likely to be. Therefore, when training a model that will be used with samples involving a specific user, it may be beneficial to collect training data from the user (e.g., data comprising measurements of the specific user). In such a case, a predictor may be referred to as a "personalized predictor", and similarly, an estimator may be referred to as a "personalized estimator".

Training a predictor and/or an estimator, and/or utilizing the predictor and/or the estimator, may be done utilizing various computer system architectures. In particular, some architectures may involve a single machine (e.g., a server) and/or single processor, while other architectures may be distributed, involving many processors and/or servers (e.g., possibly thousands or more processors on various machines). For example, some predictors may be trained utilizing distributed architectures such as Hadoop, by running distributed machine learning-based algorithms. In this example, it is possible that each processor will only have access to a portion of the training data. Another example of a distributed architecture that may be utilized in some embodiments is a privacy-preserving architecture in which users process their own data. In this example, a distributed machine learning training algorithm may allow a certain portion of the training procedure to be performed by users, each processing their own data and providing statistics computed from the data rather than the actual data itself. The distributed training procedure may then aggregate the statistics in order to generate a model for the predictor.

A predictor that predicts affective response to an event based on attributes of the event is referred to herein as an Emotional Response Predictor (ERP). Samples used for training an ERP and/or provided to an ERP for prediction may include feature values derived from descriptions of events (descriptions of events are described in further detail at least in section 4—Events). For example, in some embodiments, each sample corresponding to an event $\tau=(u, e)$ is derived from a description of the event $\tau$, and the label for the sample is derived from a measurement m corresponding to τ (i.e., a measurement of the user u to having the experience e). Optionally, a sample corresponding to an event τ(u,e) includes feature values describing the user u corresponding to the event, the experience e corresponding to the event, and/or conditions related to the instantiation of the event τ. In some embodiments, at least some of the feature values that are part of the samples provided to an ERP may be factors of events, and/or are derived from the factors of the events (factors of events are discussed in more detail further below in this disclosure).

Various machine learning-based predictors may be used by ERPs, in embodiments described herein. Examples include nearest neighbor predictors, support vector regression (SVR), regression models, neural networks, and/or decision trees, to name a few. Furthermore, training these predictors may be done using various supervised or semi-supervised methods, where at least some or all of the training data includes samples comprising feature values derived from event descriptions, and labels derived from measurements of affective response corresponding to the events. Additional information regarding training predictors such as ERPs is given above in the discussion about predictors.

In some embodiments, a sample for an ERP may include one or more feature values that describe a baseline value of the user corresponding to the event to which the sample corresponds. Optionally, the baseline affective response value may be derived from a measurement of affective response of the user (e.g., an earlier measurement taken before the instantiation of the event) and/or it may be a predicted value (e.g., computed based on measurements of other users and/or a model for baseline affective response values). Optionally, the baseline is a situation-specific baseline, corresponding to a certain situation the user corresponding to the event is in when having the experience corresponding to the event.

A predictor and/or an estimator that receives a query sample that includes features derived from a measurement of affective response of a user, and returns a value indicative of an emotional state corresponding to the measurement, may be referred to as a predictor and/or estimator of emotional state based on measurements, an Emotional State Estimator, and/or an ESE. Optionally, an ESE may receive additional values as input, besides the measurement of affective response, such as values corresponding to an event to which the measurement corresponds. Optionally, a result returned by the ESE may be indicative of an emotional state of the user that may be associated with a certain emotion felt by the user at the time such as happiness, anger, and/or calmness, and/or indicative of level of emotional response, such as the extent of happiness felt by the user. Additionally or alternatively, a result returned by an ESE may be an affective value, for example, a value indicating how well the user feels on a scale of 1 to 10.

In some embodiments, a label returned by an ESE may represent an affective value. In particular, in some embodiments, a label returned by an ESE may represent an affective response, such as a value of a physiological signal (e.g., skin conductance level, a heart rate) and/or a behavioral cue (e.g., fidgeting, frowning, or blushing). In other embodiments, a label returned by an ESE may be a value representing a type of emotional response and/or derived from an emotional response. For example, the label may indicate a level of interest and/or whether the response can be classified as positive or negative (e.g., "like" or "dislike"). In another example, a label may be a value between 0 and 10 indicating a level of how much an experience was successful from a user's perspective (as expressed by the user's affective response).

There are various methods that may be used by an ESE to estimate emotional states from a measurement of affective response. Examples of general purpose machine learning algorithms that may be utilized are given above in the general discussion about predictors and/or estimators. In addition, there are various methods specifically designed for estimating emotional states based on measurements of affective response. Some non-limiting examples of methods described in the literature, which may be used in some embodiments include: (i) physiological-based estimators as described in Table 2 in van den Broek, E. L., et al. (2010) "Prerequisites for Affective Signal Processing (ASP)—Part II." in: *Third International Conference on Bio Inspired Systems and Signal Processing, Biosignals* 2010; (ii) Audio- and image-based estimators as described in Tables 2-4 in Zeng, Z., et al. (2009) "A Survey of Affect Recognition Methods: Audio, Visual, and Spontaneous Expressions." in *IEEE Transaction on Pattern Analysis and Machine Intelligence*, Vol. 31(1), 39-58; (iii) emotional state estimations based on EEG signals may be done utilizing methods surveyed in Kim et al. (2013) "A review on the computational methods for emotional state estimation from the human EEG" in *Computational and mathematical methods in medicine*, Vol. 2013, Article ID 573734; (iv) emotional state estimations from EEG and other peripheral signals (e.g., GSR) may be done utilizing the teachings of Chanel, Guillaume, et al. "Emotion assessment from physiological signals for adaptation of game difficulty" in *IEEE Transactions on Systems, Man and Cybernetics, Part A: Systems and Humans*, 41.6 (2011): 1052-1063; and/or (v) emotional state estimations from body language (e.g., posture and/or body movements), may be done using methods described by Dael, et al. (2012), "Emotion expression in body action and posture", in *Emotion,* 12(5), 1085.

In some embodiments, an ESE may make estimations based on a measurement of affective response that comprises data from multiple types of sensors (often referred to in the literature as multiple modalities). This may optionally involve fusion of data from the multiple modalities. Different types of data fusion techniques may be employed, for example, feature-level fusion, decision-level fusion, or model-level fusion, as discussed in Nicolaou et al. (2011), "Continuous Prediction of Spontaneous Affect from Multiple Cues and Modalities in Valence-Arousal Space", *IEEE Transactions on Affective Computing*. Another example of the use of fusion-based estimators of emotional state may be found in Schels et al. (2013), "Multi-modal classifier-fusion for the recognition of emotions", Chapter 4 in *Coverbal Synchrony in Human-Machine Interaction*. The benefits of multimodal fusion typically include more resistance to noise (e.g., noisy sensor measurements) and missing data, which can lead to better affect detection when compared to affect detection from a single modality. For example, in meta-analysis described in D'mello and Kory (2015) "A Review and Meta-Analysis of Multimodal Affect Detection Systems" in *ACM Computing Surveys* (CSUR) 47.3: 43, multimodal affect systems were found to be more accurate than their best unimodal counterparts in 85% of the systems surveyed.

In one embodiment, in addition to a measurement of affective response of a user, an ESE may receive as input a baseline affective response value corresponding to the user. Optionally, the baseline affective response value may be derived from another measurement of affective response of the user (e.g., an earlier measurement) and/or it may be a predicted value (e.g., based on measurements of other users and/or a model for baseline affective response values). Accounting for the baseline affective response value (e.g., by normalizing the measurement of affective response according to the baseline), may enable the ESE, in some embodiments, to more accurately estimate an emotional state of a user based on the measurement of affective response.

Additional discussion regarding predictors, ERPs, and ESEs may be found in section 6 (Predictors and Emotional State Estimators) in the patent application U.S. Ser. No. 15/184,401.

Software Agents

As used herein, "software agent" may refer to one or more computer programs that operate on behalf of an entity. For example, an entity may be a person, a group of people, an institution, a computer, and/or computer program (e.g., an artificial intelligence). Software agents may be sometimes referred to by terms including the words "virtual" and/or "digital", such as "virtual agents", "virtual helpers", "digital assistants", and the like.

In some embodiments, a software agent acting on behalf of an entity is implemented, at least in part, via a computer program that is executed with the approval of the entity. The approval to execute the computer program may be explicit, e.g., a user may initiate the execution of the program (e.g., by issuing a voice command, pushing an icon that initiates the program's execution, and/or issuing a command via a terminal and/or another form of a user interface with an operating system). Additionally or alternatively, the approval may be implicit, e.g., the program that is executed may be a service that is run by default for users who have a certain account and/or device (e.g., a service run by an operating system of the device). Optionally, explicit and/or implicit approval for the execution of the program may be given by the entity by accepting certain terms of service and/or another form of contract whose terms are accepted by the entity.

In some embodiments, a software agent operating on behalf of an entity is implemented, at least in part, via a computer program that is executed in order to advance a goal of the entity, protect an interest of the entity, and/or benefit the entity. In one example, a software agent may seek to identify opportunities to improve the well-being of the entity, such as identifying and/or suggesting activities that may be enjoyable to a user, recommending food that may be a healthy choice for the user, and/or suggesting a mode of transportation and/or route that may be safe and/or time saving for the user. In another example, a software agent may protect the privacy of the entity it operates on behalf of, for example, by preventing the sharing of certain data that may be considered private data with third parties. In another example, a software agent may assess the risk to the privacy of a user that may be associated with contributing private information of the user, such as measurements of affective response, to an outside source. Optionally, the software agent may manage the disclosure of such data, as described in more detail elsewhere in this disclosure.

A software agent may operate with at least some degree of autonomy, in some of the embodiments described herein, and may be capable of making decisions and/or taking actions in order to achieve a goal of the entity of behalf of whom it operates, protect an interest of the entity, and/or benefit the entity. Optionally, a computer program executed to implement the software agent may exhibit a certain degree of autonomous behavior; for example, it may perform certain operations without receiving explicit approval of the entity on behalf of whom it operates each time it performs the certain operations. Optionally, these actions fall within the scope of a protocol and/or terms of service that are approved by the entity.

A software agent may function as a virtual assistant and/or "virtual wingman" that assists a user by making decisions on behalf of a user, making suggestions to the user, and/or issuing warnings to the user. Optionally, the software agent may make the decisions, suggestions, and/or warnings based on a model of the users' biases. Optionally, the software agent may make decisions, suggestions, and/or warnings based on crowd-based scores for experiences. In one example, the software agent may suggest to a user certain experiences to have (e.g., to go biking in the park), places to visit (e.g., when on a vacation in an unfamiliar city), and/or content to select. In another example, the software agent may warn a user about situations that may be detrimental to the user or to the achievement of certain goals of the user. For example, the agent may warn about experiences that are bad according to crowd-based scores, suggest the user take a certain route to avoid traffic, and/or warn a user about excessive behavior (e.g., warn when excessive consumption of alcohol is detected when the user needs to get up early the next day). In still another example, the software agent may make decisions for the user on behalf of whom it operates and take actions accordingly, possibly without prior approval of the user. For example, the software agent may make a reservation for a user (e.g., to a restaurant), book a ticket (e.g., that involves traveling a certain route that is the fastest at the time), and/or serve as a virtual secretary, which filters certain calls to the user (e.g., sending voicemail) and allows others to get through to the user.

Communication between a software agent and a user on behalf of whom the software agent operates may take various forms in different embodiments described herein. Following is a non-limiting and non-exhaustive list of examples; in some embodiments other forms of communication may be used in addition to, or instead of these examples. In one example, communication between a software agent and a user on behalf of whom it operates involves sending textual messages such as emails, SMSs, social media messages, and/or other forms of text content. In another example, communication between a software agent and a user on behalf of whom it operates involves displaying a message on display of the user, such as a monitor, a handheld device, a wearable device with a screen, an augmented reality and/or virtual reality display, and/or another form of device that may convey visual data to the user's brain (e.g., neural implants). Optionally, the message may include 2D and/or 3D images. Optionally, the message may include 2D and/or 3D videos. Optionally, the messages may include sound that is provided via a speaker that emits sound waves and/or vibrational signals (e.g., involving bone conduction). In another example, communication between a software agent and a user on behalf of whom it operates may involve haptic signals, such as applying pressure, heat, electrical current, and/or vibrations by a device or garment worn by the user, and/or a device implanted in the user. In yet another example, communication between a software agent and a user on behalf of whom it operates may involve exciting areas in the brain of the user in order to generate electrical signals in the user (e.g., involving synaptic signaling), which are interpreted by the user as information.

There are also various ways in which a user may communicate with a software agent in embodiments described herein. Following is a non-limiting and non-exhaustive list of examples; in some embodiments other forms of communication may be used in addition to, or instead of these examples. In one example, a user may communicate with a software agent via a user interface that involves providing a textual message such as by typing a message (e.g., on a keyboard or touchscreen) and/or writing a message (e.g., that is interpreted using a camera, touch screen, or a smart pen that tracks movements of the pen). Additionally or alternatively, the user interface may involve pointing and/or selecting objects presented on a screen (e.g., via touching the screen or using a pointing device such as a computer mouse). In another example, a user may communicate with a software agent by tracing (e.g., by tracing a finger on a touchscreen or in the air). In yet another example, a user may communicate with a software agent by making sounds, e.g., by speaking, whistling, clapping and/or making other sounds that may be detected using a microphone. In still another example, a user may communicate by making gestures, such as pointing or moving hands, making facial expressions, sign language, and/or making other movements that may be detected using a camera, a motion sensor, an accelerometer, and/or other sensors that may detect movement. Optionally, the gestures may involve movements of the user's tongue in the user's mouth, the clicking of teeth, and/or various forms of subvocalization that may be detected by sensors such as movement sensors, microphones, and/or pressure sensors. And in another example, a user may communicate with a software agent by thinking certain thoughts that may be detected by a device that reads electrical signals in the brain. Optionally, the certain thoughts correspond to electrical signals in the brain that have characteristic patterns (e.g., certain amplitudes and/or excitation in certain areas of the brain). Optionally, the electrical signals are read via EEG, and interpreted using signal processing algorithms in order to determine the meaning of the user's thought (e.g., a desire of the user for a certain object, a certain action, and/or to move in a certain direction).

In some embodiments, communication between a software agent and a user may be done in such a way that the content exchanged between the software agent and the user (and/or vice versa) may not be known to an entity that is not the user or the software agent, even if the entity is in the vicinity of the user at the time of communication. For example, the software agent may send a message displayed on augmented reality glasses and/or play message via headphones. In another example, a user may communicate with a software agent via subvocalization and/or selecting of options by pointing at a virtual menu seen using augmented reality glasses. Optionally, the communication may take place in such a way that an entity that is in the vicinity of the user is not likely to identify that such a communication is taking place.

In some embodiments, a software agent, and/or one or more of the programs it may comprise, may simultaneously operate on behalf of multiple entities. In one example, a single process running on a CPU or even a single execution thread, may execute commands that represent actions done on behalf of multiple entities. In another example, a certain running program, such as a server that responds to queries, may be considered comprised in multiple software agents operating on behalf of multiple entities.

In some embodiments, a single service, which in itself may involve multiple programs running on multiple servers, may be considered a software agent that operates on behalf of a user or multiple users. Optionally, a software agent may be considered a service that is offered as part of an operating system. Following are some examples of services that may be considered software agents or may be considered to include a software agent. In one example, a service simply called "Google", "Google Now", or some other variant such as "Google Agent" may be services that implement software agents on behalf of users who have accounts with Google™ Similarly, Ski® or "Proactive Assistant" may be considered software agents offered by Apple™ In another example, "Cortana" may be considered a software agent offered by Microsoft™. In yet another example, "Viv" may be considered a software agent from Viv Labs. And in another example, "Watson" may be considered a software agent developed and/or offered by IBM™.

Implementation of a software agent may involve executing one or more programs on a processor that belongs to a device of a user, such as a processor of a smartphone of the user or a processor of a wearable and/or implanted device of the user. Additionally or alternatively, the implementation of a software agent may involve execution of at least one or more programs on a processor that is remote of a user, such as a processor belonging to a cloud-based server.

Additional discussion regarding predictors, ERPs, and ESEs may be found in section 7 (Software Agents) in the patent application U.S. Ser. No. 15/184,401.

Factors of Events

As typically used herein, a factor of an event (also called an "event factor") represents an aspect of an event (also referred to as an attribute related to the event). When the context is clear, a factor of an event may be referred to as simply a "factor". The user corresponding to the event may have bias to the aspect represented by the factor, such that when the user is exposed to, and/or aware of, the factor, this may influence the affective response corresponding to the event (e.g., as determined from a measurement of the user corresponding to the event). Optionally, in a case in which an aspect of an event is expected (e.g., according to a model) to influence the affective response to the event, the factor corresponding to the aspect may be considered relevant to the event. Similarly, if an aspect of an event is not expected to influence the affective response to the event, the factor corresponding to the aspect may be considered irrelevant to the event. Herein, when a factor is considered relevant to an event, it may also be considered to "characterize" the event, and in a similar fashion, the event may be considered to be "characterized" by the factor.

An aspect of an event may relate to the user corresponding to the event, the experience corresponding to the event, and/or to the instantiation of the event. In addition to referring to a factor of an event as "representing an aspect of an event", a factor of an event may also be referred to as "describing the aspect of the event", and/or "corresponding to the aspect of the event". Additionally, by corresponding to certain aspects of an event, it may also be said that factors describe the event and/or correspond to it. In such a case, a factor may said to be "a factor of a certain event".

The terms "factor", "factor of an event", and the like, are to be interpreted similar to how the term "variable" may be used in the arts of programming and/or statistics. That is a factor may have an attribute it describes (i.e., the aspect of the event). For example, the attribute may describe the height of the user, the difficulty of the experience, and/or the temperature outside when the user had the experience. In some embodiments, factors may also have values, which are also referred to as weights. These values can describe a quantitative properties of the aspects to which the factors correspond. For example, values corresponding to the latter examples may be: 6'2", 8 on a scale from 1 to 10, and 87°

F. Additionally or alternatively, a value associated to a factor of an event may be indicative of the importance and/or dominance of an aspect to which the factor corresponds (in this case the value is often referred to as a weight). Optionally, the weight associated with a factor of an event is indicative of the extent of influence the factor is likely to have on the affective response of the user corresponding to the event. Optionally, the weight associated with a factor of an event is indicative of how relevant that factor is to the event. For example, the higher the weight, the more relevant the factor is considered. Optionally, a factor that is irrelevant to an event receives a weight that is below a threshold. Optionally, a factor that is irrelevant to an event receives a weight of zero. Setting a value and/or weight of a factor may also be referred to herein as assigning the factor with a value and/or weight.

In some embodiments, a factor of an event may have an associated value that is an indicator of whether a certain aspect of the event happened. Optionally, the indicator may be a binary weight, which is zero if the aspect didn't happen and one if it did. For example, a factor of an event may correspond to the user missing a train (it either happened or not), to the user having slept at least eight hours the night before, or to the user having taken prescribed medicine for the day. Depending on the embodiment, some factors corresponding to indicators may instead, or in addition, be represented by a weight describing quantitative properties of the aspects to which the factors correspond. For example, instead of having an indicator on the hours of sleep as described in the example above, the weight of such a factor may be the value representing the actual number of hours of sleep the user had.

In some embodiments, factors of events are derived from descriptions of the events. Optionally, descriptions of events are produced by an event annotator (e.g., event annotator 701) and/or utilize data from various sources, as described in this disclosure. In one embodiment, a description of an event in itself includes factors of the event and/or values of weights of factors. In another embodiment, analysis of the description, possibly involving various programs and/or predictors as described below, may be required in order to be able to assign factors to the event and/or determine weights of factors.

In some embodiments, assigning factors to events is done, at least in part, by software agents. For example, a software agent may perform some of the monitoring and/or analysis involved in generating a description of an event. Optionally, a software agent operating on behalf of a user may participate in the process of selecting which factors are relevant to an event and/or assigning weights to the factors. For example, the software agent may narrow down a list of possible factors provided by another program and select certain ones that best represent factors that may influence the affective response of the user. Optionally, this selection is based on past events corresponding to the user. Additionally or alternatively, the selection may be based on models of the user such as models describing biases of the user (e.g., the software agent may select factors for which the user has a bias that is not insignificant).

The following are non-limiting examples of some of the types of factors that may be utilized in some embodiments. These examples are presented for illustrative purposes, and are not comprehensive (other types of factors may be utilized in embodiments). Additionally, different embodiments may involve different subsets of the factors described below, and/or involve different variants of these factors.

Each event that involves having a certain experience may, in some embodiment, be characterized by factors corresponding to the certain experience. Optionally, at least one of the factors simply represents that fact that the event involved the certain experience. Optionally, a bias value that corresponds to that factor may express how a user feels about having the certain experience (thus, such a value may be considered a "personal score" of a user towards the certain experience). Below are additional examples of factors that may be related to the experience corresponding to an event.

In some embodiments, a factor of an event may describe an aspect of the experience corresponding to the event, such as what type of experience it is (e.g., mental activity, physical activity, a chore, or recreational), or where it takes place (e.g., at home, outside, at work). Factors may correspond to various attributes regarding the instantiation of the event, such as how long it took, its level of difficulty (e.g., game level), or its cost. Additional examples of factors may relate to the environment in which the experience took place, such as the temperature, noise level, and/or presence or absence of different people when the experience took place (e.g., was the user with a friend or alone).

A factor of an event may correspond to an object that is part of the experience corresponding to the event. In one example, the object might have been used by the user corresponding to the event (e.g., a broom, a ball, or sunscreen). In another example, the object may be something viewed by the user (e.g., an object the user sees while browsing a virtual store). In still another example, the experience corresponding to the event is a computer-related experience, and the factor may correspond to what hardware was used (e.g., what gadget or user-interface were involved) and/or what software was used as part of having the experience.

Furthermore, in some embodiments, factors of an event may correspond to a specific characteristic of an object involved in the experience corresponding to the event. Examples of characteristics that may be addressed in some embodiments include the following: weight, volume, size, time, shape, color, position, texture, density, smell, value, consistency, depth, temperature, function, appearance, price, age, and significance. For example, a factor corresponding to an experience involving buying a shirt may be the color of the shirt or the softness of the fabric. In another example, a factor corresponding to an experience involving drinking soup may be the temperature of the soup. In still another example, a factor corresponding to an experience involving drinking a glass of wine may be the age of the wine and/or the variety of the wine. In yet another example, a factor corresponding to an experience of buying a piece of jewelry may be the price of the piece of jewelry.

In some embodiments, factors may correspond to low-level features of content, such as illumination, color scheme, tempo, sound energy, and the like. Factors may also correspond to high-level concepts of an experience such as genre of content.

When an experience involves a substance that is consumed by the user corresponding to an event (e.g., a food item, a beverage, and/or another type of substance), a factor of the event may relate to the chemical composition of the substance, a nutritional value of the substance, and/or other physical properties of the substance. In one example, a factor describes properties such as the caloric intake involved in consuming the substance, the weight of carbohydrates in the substance, and/or the percentage of saturated fats in the substance. In another example, a factor may relate to certain ingredients in the substance (e.g., whether it includes alcohol, peanuts, or cilantro). In still another example, a factor may relate to the concentration of certain molecules and/or groups of chemicals in the substance (e.g., how many ppm of mercury or what concentration of salts).

Many experiences may involve people or other entities (e.g., robots or avatars) with whom a user having an experience may interact. Additionally or alternatively, the entities may be part of the experience in other ways (e.g., the experience involves viewing an image or video of an entity). Thus, in some embodiments, a factor corresponding to an experience may identify an entity (person or other) that is part of the experience a user has. Optionally, the factor may correspond to certain person (e.g., a certain friend of the user corresponding to an event or a certain teacher of the user) or to a certain entity that is not a real person (e.g., a certain robot, a certain operating system, and/or a certain software agent). A factor of an event may also correspond to groups of entities (e.g., a factor may correspond to the presence of policemen, party-goers, or experienced gamers, who are part of an experience in some way).

A factor of an event may correspond to a characteristic of an entity (person or other) that is part of the experience corresponding to the event. Examples of characteristics may include ethnicity, age, gender, appearance, religion, occupation, height, weight, hairstyle, spoken language, or demeanor. Additionally, a characteristic may correspond to the mood or emotional state of the entity and/or various behavioral traits (e.g., mannerisms that may be considered to be obsessive-compulsive). Optionally, determining behavioral traits may be done from observation of the entity, semantic analysis of communications involving the entity, analysis of voice and body language, reports from the user or other users. For example, U.S. Pat. No. 9,019,174 titled "Wearable emotion detection and feedback system" describes a device comprising cameras mounted on a user's headwear (e.g., glasses) which can be used to determine emotional states of people interacting with the user.

In some embodiments, the quality of the experience corresponding to an event may be considered a factor of the event. Optionally, the quality of the experience corresponding to the event is based on a score computed for the experience corresponding to the event. For example, the score may be a crowd-based score computed based on measurements of affective response of multiple users, such as at least 3, 5, 10, 100, or at least 1000 users, each of whom contributed a measurement of affective response corresponding to the experience towards the computation of the score.

In one example, affective response corresponding to an event that involves watching a live show may be dependent on the quality of the show, with a poor performance yielding a negative affective response to the show, while a good show may make the affective response more positive. It is to be noted that different users may react differently to a factor such as this, with some users, for example, being more disappointed than others by a low quality experience. In this example, the quality of the show may be determined based on a score computed from measurements of affective response of multiple users that are viewing the live show.

In another example, affective response corresponding to an event that involves eating a meal at a restaurant may be dependent on the quality of the food and/or the service at the restaurant. Optionally, the quality of the food and/or service is represented by a score computed based on measurements of affective response of other users who ate at the same restaurant.

In some embodiments, a factor of an event may describe an aspect of the user corresponding to the event, such as a situation in which the user is in during the instantiation of the event. The situation may refer to one or more various conditions that may influence the affective response of the user. Optionally, the situation may refer to a physical and/or mental state of the user. In one example, a situation of the user may be a physiological state such as having high blood pressure or a certain level of sugar in the blood. In another example, the situation may refer to a mental state of the user, such as being intoxicated, depressed, euphoric, or exhausted.

Factors of events may be represented in different ways in different embodiments described herein. For example, factors may be represented as a subset and/or list of relevant factors, as vectors of values, and/or using other representations of information (e.g., a structured database record). In some embodiments, there may be a plurality of factors that can potentially be relevant to an event. However, typically, only a fraction of the potential factors are relevant to the event to the extent that they are likely to affect the affective response of the user to the experience corresponding to the event.

In one embodiment, relevant factors of an event are a subset of the plurality of the factors that may possibly be used to characterize the event. Optionally, the subset of factors comprises less than half of the plurality of the factors. The subset of factors may be represented in various ways. In one example, the subset may be represented as a list containing the factors in the subset (or information identifying them such as names, codes, indexes, etc.). Optionally, the list is ordered according to the perceived impact of the factors on the affective response of the user. In another example, the subset may be represented as a vector of values, each indicating whether a certain factor belongs to the subset or not (e.g., a vector of indicators in which a "1" indicates that the corresponding factor is relevant and a "0" indicates that it is not).

In another embodiment, a degree of relevancy may be assigned to at least some factors from among the plurality of potential factors. Optionally, the degree of relevancy of a factor is represented by a weight of the factor which may be represented as a numerical value. For example, factors may be represented by a vector of weights, each position in the vector corresponding to a certain factor and the value in each position indicating the weight of the certain factor in the instantiation of the event. Optionally, at least half the plurality of factors have a lower weight than other the rest of the plurality of factors. Optionally, a weight that is below a certain threshold may be indicative that the corresponding factor is not relevant and/or is not likely to have an impact on the affective response of the user corresponding to the event. Optionally, a weight that equals zero is indicative that the corresponding factor is not relevant and/or is not likely to have an impact on the affective response of the user corresponding to the event.

In some embodiments, factors of an event τ may be represented by a vector $\vec{F}_\tau$ that contains weights that are numerical values (with each position storing the weight corresponding to a certain factor). Optionally, the larger the value of the weight, the more the corresponding factor is expected to influence the affective response of the user corresponding to the event. It is to be noted that the process of assigning weights to factors may be considered a form of selection of relevant factors, since it is possible to determine that factors with a weight above a certain threshold are to be considered factors that are relevant to the event, while the other factors (with lower associated weights), may be considered to be less relevant (or irrelevant). In another example, a certain number of factors with the highest weights are considered relevant to the event, while the other factors (with possibly lower weights) are considered less relevant, or irrelevant, to the event.

In one embodiment, the values in the vector $\vec{F}_\tau$ are binary. For example, a weight of zero in certain position represents that the factor corresponding to the certain position is not relevant, and a weight of one in that position represents that the factor is considered relevant. In another embodiment, the values in the vector $\vec{F}_\tau$ may come from a larger set of numerical values, such as integer or real values. Optionally, the values in $\vec{F}_\tau$ may be non-negative, (e.g., representing that event values may be relevant or non-relevant). Optionally, the values in $\vec{F}_\tau$ may be positive or negative values.

A more comprehensive discussion factors of events and their properties may be found in section 12 (Factors of Events) in the patent application U.S. Ser. No. 15/184,401.

Modeling Bias

There are various ways in which the effects of user biases on affective response may be modeled and/or represented in embodiments described herein. Following is a discussion about different ways to model bias which starts with "bias values" and continues with "bias functions". The models described below may be considered models of the user 101, such as the model 912 or other models of users described in this disclosure.

In particular, in some embodiments, biases may be considered to have values that are referred to as "bias values".

Optionally, bias values may be random variables (e.g., the bias values are represented via parameters of distributions) and/or bias values may be scalar values or vectors. In some embodiments, the bias values are determined from parameters of models trained data that includes measurements of affective response corresponding to events. Below are descriptions of bias values and various ways they may be used in some embodiments, including notations and ways in which data may be utilized in order to learn bias values and/or correct measurements of affective response with respect to bias values. The description is provided for illustrative purposes; those skilled in the art will recognize that there may be other methods of notation that may be used, and other ways of handling, learning, and/or correcting biases that may be employed to achieve similar results.

Bias values may be expressed in various ways. In some embodiments, bias values are expressed in the same units as measurements of affective response and/or scores for experiences are expressed. For example, bias values may be expressed as affective values. Optionally, a bias value may represent a positive or negative value that is added to a measurement and may change the value of the measurement. In one example, a bias value represents a number of heart beats per minute (or a change in the number of heartbeats), e.g., a first bias may equal +5 beats per minute (PBM), while a second bias equal −10 BPM. In another example, a bias value represents a change in emotional response. In this example, emotional responses are expressed as points in the two-dimensional Valence/Arousal plane. A bias value may be expressed as an offset to points on this plane, such as an adding +2 to the Valence and +1 to the Arousal. Thus, in this example, the bias value is a vector that may be used to perform a transformation on a representation of the emotional response. In yet another example, a measurement of affective response may be a time series, such as a brainwave pattern of a certain frequency (band) that is recorded over a period of time. In this example, a bias value may also be expressed as a pattern which may be superposed on the measurement in order to change the pattern (i.e., incorporate the effect of the bias). And in still another example, a bias value may a factor added to a score, such as a factor of −0.5 added to a value on a scale from 1 to 10 that expresses a level of user satisfaction.

In some embodiments, measurements of affective response of users who had experiences are used to train a model that includes biases expressed via bias values; each of the experiences may correspond to something akin to visiting a location, participation in an activity, or utilizing a product. In the embodiments, each of those measurements of affective response may correspond to an event in which a certain user had a certain experience.

Following is a description of an embodiment in which a user's biases are modeled as bias values that correspond to factors. Thus, the effect of each factor on the affective response of the user is represented by its corresponding bias value. Given an event τ, the user corresponding to the event is denoted below $u_\tau$, the experience corresponding to the event is denoted $e_\tau$ and the measurement of affective response corresponding to the event is denoted $m_\tau$. The set of factors of the event τ is represented below by the vector $\vec{F}_\tau = (f_1, f_2, \ldots, f_n)$. Optionally, $\vec{F}_\tau$ represents a vector of weights associated with factors of the event τ, such that weight of factor i is $f_i$ (with some of the weights possibly being zero). $\vec{F}_\tau$ may contain various types of values, such as binary values or real values. If factors of an event are given as a set of factors, they may be still represented via a vector of factors, e.g., by having $\vec{F}_\tau$ be a vector with weights of one at positions corresponding to factors in the set, and a weight of zero in other positions.

The full set of bias values of a user u are represented below by a vector $\vec{B}$, with each value in a position in the vector $\underline{B}$ corresponding to a certain factor. When referring to a certain event τ, the vector of bias values corresponding to the factors that characterize τ may be denoted $\vec{B}_\tau = (b_1, b_2, \ldots b_n)$. Both the vectors $\vec{F}_\tau$ and $\vec{B}_\tau$ are assumed to be of the same length n. If $\vec{F}_\tau$ contains only a subset of all possible factors (e.g., it include only factors that are relevant to τ, at least to a certain degree), it is assumed that the vector $\vec{B}_\tau$ includes the corresponding bias values to the factors in $\vec{F}_\tau$, and not the full set of bias values $\vec{B}_u$ (assuming the user u is the user corresponding to the event τ). Therefore, in Eq. (1) to Eq. (5), the same dimensionality is maintained for both vectors $\vec{F}_\tau$ and $\vec{B}_\tau$ corresponding to each event τ.

In some embodiments, a measurement corresponding to an event τ, denoted $m_\tau$, may be expressed as function that takes into account the accumulated effect of factors represented by $\vec{F}_\tau$ with respect to the bias values represented by $\vec{B}_\tau$, according to the following equation:

$$m_\tau = \mu_\tau + \vec{F}_\tau \cdot \vec{B}_\tau + \varepsilon = \mu_\tau + \left(\sum_{i=1}^{n} f_i \cdot b_i\right) + \varepsilon \quad (1)$$

where $\mu_\tau$ is a value representing an expected measurement value (e.g., a baseline), and $\epsilon$ is a noise factor drawn from a certain distribution that typically has a mean of zero, and is often, but not necessarily, a zero-mean Gaussian distribution such that $\epsilon \sim N(0, \sigma^2)$, for some $\sigma > 0$.

Depending on the embodiment, $\mu_\tau$ may represent different values. For example, in some embodiments $\mu_\tau$ may be set to zero; this may indicate that the measurement of affective response $m_\tau$ is modeled as being dependent on the bias reaction of the user to factors representing the event. In other embodiments, $\mu_\tau$ may be given values that may be non-zero; for example, $\mu_\tau$ may represent a baseline value. In one embodiment, $\mu_\tau$ is the same for all events (e.g., a baseline value for a certain user or of a group of users). In other embodiments, $\mu_\tau$ may be different for different events. For example, $\mu_\tau$ may be a baseline computed for the user $\mu_\tau$ based on measurements of affective response of $\mu_\tau$ taken a certain time before the instantiation of $\mu_\tau$. In another example, $\mu_\tau$ may represent an expected measurement value for the experience $e_\tau$. For example, $\mu_\tau$ may be a baseline computed based on prior measurements of the user $\mu_\tau$ and/or other users to having the experience $e_\tau$.

In some embodiments, $\epsilon$ from Eq. (1) may represent a sum of multiple noise factors that may be relevant to a certain event $\tau$. Optionally, each of the multiple noise factors is represented by a zero-mean distribution, possibly each having a different standard deviation.

It is to be noted that discussions herein regarding bias values are not meant to be limited to measurements and bias values that are scalar values. Measurements of affective response, as well as biases, may be expressed as affective values, which can represent various types of values, such as scalars, vectors, and/or time series. Additionally, though Eq. (1) describes the measurement $m_\tau$ corresponding to an event $\tau$ as being the results of a linear combination of factors $\vec{F}_\tau$ and their corresponding bias values $\vec{B}_\tau$, other relationships between factors of events and bias values may exist.

In some embodiments, in which measurements of affective response corresponding to events are modeled as additive functions of factors of the events and corresponding bias values, as described in Eq. (1), the bias values may be learned from training data. This learning may involve various approaches that utilize objectives such as minimizing squared error associated with the assignment to $\vec{B}$. To this end, various computational approaches may be utilized such as linear regression techniques, gradient-based approaches, and/or randomized explorations of the search space of possible assignments of values to $\vec{B}$.

The likelihood of the data is another example of an objective that may be optimized in order to determine bias values for a user. In some embodiments, each of the bias values in $\vec{B}$ may be assumed to be a random variable, drawn from a distribution that has a certain set of parameters. Depending on the type of distributions used to represent the bias values, a closed-form expression may be obtained for the distribution of a weighted sum of a subset of the bias values. Thus, with a given set of training data that includes events with their corresponding factors and measurements of affective response, it is possible to find values of the parameters of the bias values which maximize the likelihood of the training data.

In some embodiments, which involve bias values, the bias values may be assumed to be independent of each other. Similarly, in some embodiments, bias values modeled as random variables may be assumed to be i.i.d random variables. There may be embodiments in which such independence assumptions do not hold in practice, but rather are only violated to a certain (acceptable) degree. Thus, the bias modeling approaches described above are still applicable and useful in embodiments where the independence assumptions may not always hold. Optionally, in some embodiments, dependencies between bias values may be modeled utilizing joint distributions of bias values. For example, the likelihood of data may be modeled utilizing a graphical model (e.g., a Bayesian network) having a structure that takes into account at least some of the dependencies between biases. In another example, certain factors may be generated by combining other factors; thus a bias value corresponding to the combination of factors will take into account dependencies between bias values.

In some embodiments, finding the values of bias values in $\vec{B}$ may be done utilizing a general function of the form $f(\vec{B}, V)$, which returns a value indicative of the merit of the bias values of $\vec{B}$ given the measurement data corresponding to the events in $V$. Depending on the nature of the function $f(\vec{B}, V)$ various numerical optimization approaches may be used. Additionally, an assignment of bias values for $\vec{B}$ may be searched utilizing various random and/or heuristic approaches (e.g., simulated annealing or genetic algorithms), regardless of the exact form of $f$, which may even not be known in some cases (e.g., when $f$ is computed externally and is a "black box" as far as the system is concerned).

A common characteristic of some embodiments using such an approach is that the effect of the biases is modeled as being governed by a structured, relatively simple, closed-form formula, such as Eq. (1). The formula typically reflects an assumption of independence between factors and between bias values, and is often linear in the values of the relevant bias values and weights of factors. However, in some embodiments, the effects of biases may be modeled without such assumptions about the independence of factors, and a formula involving factors and bias values that is additive and/or linear. In particular, in some embodiments, the effects of biases may be complex and reflect various dependencies between factors that may influence affective response of users in a non-linear way.

In some embodiments, bias functions, described in this section, model effects of biases while making less restricted assumptions (e.g., of independency and/or linearity of effects), compared to linear functions of bias values and factors described in the previous section. Optionally, bias functions are implemented using machine learning-based predictors, such as emotional response predictors like ERPs.

In some embodiments, implementing a bias function is done utilizing an ERP that receives as input a sample comprising feature values that represent factors related to an event $\tau = (u, e)$. For example, a sample may comprise values of factors, such as values from $\vec{F}_\tau$ described in previous sections, and/or values derived from the factors. Additionally or alternatively, the sample may include various other values derived from a description of the event $\tau$. These other values may include values describing the user $u$, the experience $e$, and/or values corresponding to attributes involved in the instantiation of the event $\tau$ (e.g., the location where it happened, how long it took, who participated, etc.). The ERP may then utilize the sample to predict an affective response corresponding to the event, which represents the value $m$ of a measurement of affective response of the user $u$ to having the experience $e$ (had such a measurement been taken).

Many types of machine learning-based predictors, including predictors that may be used to implement an ERP, are capable of representing non-linear functions of feature values that may reflect dependencies between some of the feature values. These dependencies may be between factors and/or other values such as values characterizing the user or experience corresponding to an event. As such, the predictors may be used to model a user's biases (i.e., the user's "bias function"), in which factors may influence the value of affective response to an experience in a wider array of ways than may be modeled with bias values alone, as described in the previous section. This wider capability may be used, in some embodiments, to offer a modeling of various complex thought processes the user may have with respect to relevant factors. The nature of these thought processes and/or their results may be characteristic of the user's psyche, world view, moral values, etc.

In some embodiments, biases of a user modeled using an ERP are learned from data comprising samples derived from a set of events V. Optionally, each sample based an event $\tau \in V$ comprises feature values corresponding to the event $\tau$ and a label that is based on $m_\tau$, which is a measurement of affective response corresponding to $\tau$ (i.e., a measurement of $u_\tau$, the user corresponding to $\tau$, to having $e_\tau$ the experience corresponding to $\tau$). In one example, the feature values may include factors taken from the vector $\vec{F}_\tau$ described above. In another example, the feature values may include values derived from the description of the event T, such as values describing aspects of the user $u_\tau$ the experience $e_\tau$, and/or aspects of the instantiation of the event $\tau$).

As discussed herein, there may be various machine learning approaches that can be used to train an ERP. Additionally, depending on the composition of events in V, the ERP may be generalizable and be able to predict affective response to certain events that may not be well represented in V (or represented in V at all). Optionally, an ERP may be generalizable because the samples it is trained with include feature values that describe various aspects of an event. These aspects may come from a description of an event, and not necessarily be factors of the event. Thus, while the user may not have a direct reaction to these aspects, they may help in determining the reaction of the users to other aspects of the event. In one example, feature values in a sample may describe demographic characteristics of a user (e.g., age, occupation, ethnicity, level of education, region of residence, etc.) These aspects are not aspects that a user typically reacts to (since they are the same in all events which involve the user). However, knowing these aspects may help predict the affective response of a user to an event since for example, it is likely that people from a similar background may react similarly to having a certain experience.

In some embodiments, the set V of events, from which the samples used to train an ERP are derived, includes events corresponding to multiple users, and at least some of the samples include feature values that are based on one or more scores. For example, each sample, from among the at least some of the samples, may include a feature value that corresponds to the quality of an experience corresponding to the event the sample represents, which is determined from a score for the experience corresponding to the event. Optionally, the score is computed based on measurements of affective response of multiple users, where depending on the embodiment, the multiple users include at least 2, 3, 5, 10, 100, 1000, 10000, or at least 100000 different users. Optionally, at least some of the multiple users are corresponding users for events in V. Alternatively, not one of the multiple users is the corresponding user of an event in V. Additionally, in some embodiments, the measurements of affective response of the multiple users may all be taken within a certain window of time. For example, the window of time may span a second, thirty seconds, a minute, fifteen minutes, an hour, a day, a week, a month, a year, more than a year, or some other time frame between one second and one year.

Bias functions may be utilized, in some embodiments, to learn bias values corresponding to individual factors and/or combinations of factors. For example, once an ERP that implements a bias function is trained, it can be used to make various predictions that may teach the bias values a user likely has.

In one embodiment, the bias value corresponding to a certain factor is determined utilizing an ERP. Let $f'$ denote the weight of the certain factor. In this embodiment, the ERP is utilized to compute the corresponding bias value $b'$. Computing $b'$ is done as follows. Given an event, two related samples are generated for the ERP. The first sample is a sample that contains all factors and their corresponding weights, which would typically be included in a sample corresponding to the event. The second sample is a sample identical to the first, except for the certain factor, whose values is set to zero (i.e., in the second sample $f'=0$). After providing both samples to the ERP, the difference between the first sample (which includes the certain factor) and the second sample (which does not include the certain factor) represents the effect of the certain factor, from which an estimate of $b'$ may be derived. That is, the difference between the prediction of emotional response to the first sample and the prediction of emotional response to the second sample is the term $f' \cdot b'$. By dividing the difference by the weight of $f'$, an estimate of the value of $b'$ may be obtained.

In one embodiment, computing an estimate of the bias value using the process described above is repeated n times utilizing different events, where n>1 (e.g., n may be 5, 10, 100, 1000, or 1000). Optionally, the value of $b'$ is determined based on the n estimates of $b'$ computed from pairs of samples generated for the n different events, such as the average of those n estimates. Optionally, additional statistics are computed from the n estimates, such as the variance of $b'$. Optionally, probability density function of $b'$ is computed from the n estimates.

Additional Considerations

Figure 8:
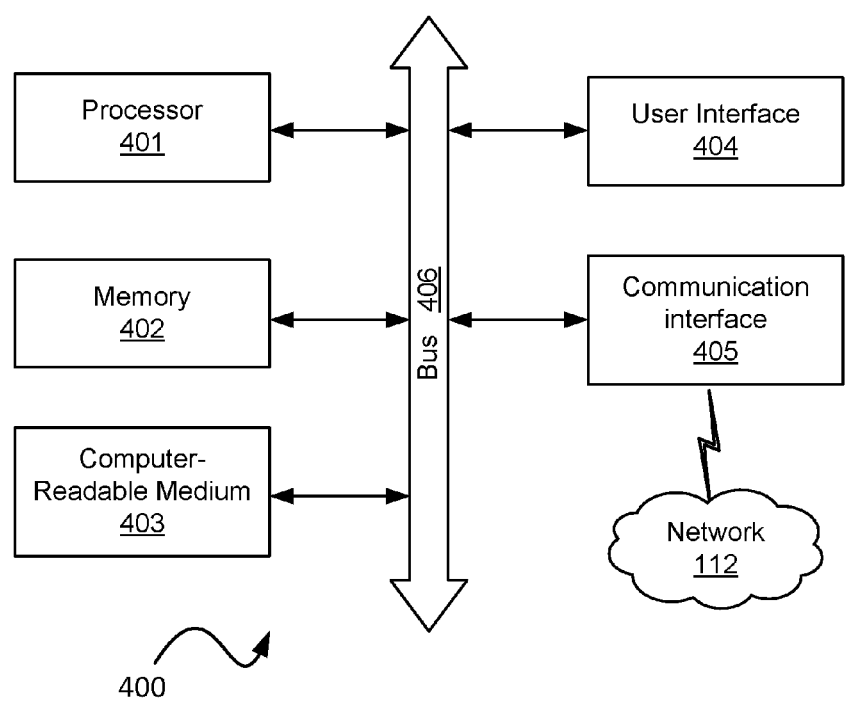
FIG. 8 illustrates a computer system architecture that may be utilized in various embodiments in this disclosure.

FIG. 8 is a schematic illustration of a computer 400 that is able to realize one or more of the embodiments discussed herein. The computer 400 may be implemented in various ways, such as, but not limited to, a server, a client, a personal computer, a set-top box (STB), a network device, a handheld device (e.g., a smartphone), computing devices embedded in wearable devices (e.g., a smartwatch or a computer embedded in clothing), computing devices implanted in the human body, and/or any other computer form capable of executing a set of computer instructions. Further, references to a computer include any collection of one or more computers that individually or jointly execute one or more sets of computer instructions to perform any one or more of the disclosed embodiments.

The computer 400 includes one or more of the following components: processor 401, memory 402, computer readable medium 403, user interface 404, communication interface 405, and bus 406. In one example, the processor 401 may include one or more of the following components: a general-purpose processing device, a microprocessor, a central processing unit, a complex instruction set computing (CISC) microprocessor, a reduced instruction set computing (RISC) microprocessor, a very long instruction word (VLIW) microprocessor, a special-purpose processing device, an application specific integrated circuit (ASIC), a field programmable gate array (FPGA), a digital signal processor (DSP), a distributed processing entity, and/or a network processor. Continuing the example, the memory 402 may include one or more of the following memory components: CPU cache, main memory, read-only memory (ROM), dynamic random access memory (DRAM) such as synchronous DRAM (SDRAM), flash memory, static random access memory (SRAM), and/or a data storage device. The processor 401 and the one or more memory components may communicate with each other via a bus, such as bus 406.

Still continuing the example, the communication interface 405 may include one or more components for connecting to one or more of the following: LAN, Ethernet, intranet, the Internet, a fiber communication network, a wired communication network, and/or a wireless communication network. Optionally, the communication interface 405 is used to connect with the network 112. Additionally or alternatively, the communication interface 405 may be used to connect to other networks and/or other communication interfaces. Still continuing the example, the user interface 404 may include one or more of the following components: (i) an image generation device, such as a video display, an augmented reality system, a virtual reality system, and/or a mixed reality system, (ii) an audio generation device, such as one or more speakers, (iii) an input device, such as a keyboard, a mouse, a gesture based input device that may be active or passive, and/or a brain-computer interface.

Functionality of various embodiments may be implemented in hardware, software, firmware, or any combination thereof. If implemented at least in part in software, implementing the functionality may involve a computer program that includes one or more instructions or code stored or transmitted on a computer-readable medium and executed by one or more processors. Computer-readable media may include computer-readable storage media, which corresponds to a tangible medium such as data storage media, or communication media including any medium that facilitates transfer of a computer program from one place to another. Computer-readable medium may be any media that can be accessed by one or more computers to retrieve instructions, code and/or data structures for implementation of the described embodiments. A computer program product may include a computer-readable medium.

In one example, the computer-readable medium 403 may include one or more of the following: RAM, ROM, EEPROM, optical storage, magnetic storage, biologic storage, flash memory, or any other medium that can store computer readable data. Additionally, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of a medium. It should be understood, however, that computer-readable medium does not include connections, carrier waves, signals, or other transient media, but are instead directed to non-transient, tangible storage media.

A computer program (also known as a program, software, software application, script, program code, or code) can be written in any form of programming language, including compiled or interpreted languages, declarative or procedural languages. The program can be deployed in any form, including as a standalone program or as a module, component, subroutine, object, or another unit suitable for use in a computing environment. A computer program may correspond to a file in a file system, may be stored in a portion of a file that holds other programs or data, and/or may be stored in one or more files that may be dedicated to the program. A computer program may be deployed to be executed on one or more computers that are located at one or more sites that may be interconnected by a communication network.

Computer-readable medium may include a single medium and/or multiple media (e.g., a centralized or distributed database, and/or associated caches and servers) that store the one or more sets of instructions. In various embodiments, a computer program, and/or portions of a computer program, may be stored on a non-transitory computer-readable medium. The non-transitory computer-readable medium may be implemented, for example, via one or more of a volatile computer memory, a non-volatile memory, a hard drive, a flash drive, a magnetic data storage, an optical data storage, and/or any other type of tangible computer memory to be invented that is not transitory signals per se. The computer program may be updated on the non-transitory computer-readable medium and/or downloaded to the non-transitory computer-readable medium via a communication network such as the Internet. Optionally, the computer program may be downloaded from a central repository such as Apple App Store and/or Google Play. Optionally, the computer program may be downloaded from a repository such as an open source and/or community run repository (e.g., GitHub).

At least some of the methods described in this disclosure, which may also be referred to as "computer-implemented methods", are implemented on a computer, such as the computer 400. When implementing a method from among the at least some of the methods, at least some of the steps belonging to the method are performed by the processor 401 by executing instructions. Additionally, at least some of the instructions for running methods described in this disclosure and/or for implementing systems described in this disclosure may be stored on a non-transitory computer-readable medium.

Some of the embodiments described herein include a number of modules. Modules may also be referred to herein as "components" or "functional units". Additionally, modules and/or components may be referred to as being "computer executed" and/or "computer implemented"; this is indicative of the modules being implemented within the context of a computer system that typically includes a processor and memory. Generally, a module is a component of a system that performs certain operations towards the implementation of a certain functionality. Examples of functionalities include receiving measurements (e.g., by a collection module), computing a score for an experience (e.g., by a scoring module), and various other functionalities described in embodiments in this disclosure. Though the name of many of the modules described herein includes the word "module" in the name, this is not the case with all modules; some names of modules described herein do not include the word "module" in their name (e.g., the event annotator 701).

The following is a general comment about the use of reference numerals in this disclosure. It is to be noted that in this disclosure, as a general practice, the same reference numeral is used in different embodiments for a module when the module performs the same functionality (e.g., when given essentially the same type/format of data). Thus, as typically used herein, the same reference numeral may be used for a module that processes data even though the data may be collected in different ways and/or represent different things in different embodiments.

It is to be further noted that though the use of the convention described above that involves using the same reference numeral for modules is a general practice in this disclosure, it is not necessarily implemented with respect to all embodiments described herein. Modules referred to by a different reference numeral may perform the same (or similar) functionality, and the fact they are referred to in this disclosure by a different reference numeral does not necessarily mean that they might not have the same functionality.

Executing modules included in embodiments described in this disclosure typically involves hardware. For example, a module may comprise dedicated circuitry or logic that is permanently configured to perform certain operations (e.g., as a special-purpose processor, or an application-specific integrated circuit (ASIC)). Additionally or alternatively, a module may comprise programmable logic or circuitry (e.g., as encompassed within a general-purpose processor or a field programmable gate array (FPGA)) that is temporarily configured by software/firmware to perform certain operations. For example, a computer system such as the computer system illustrated in FIG. 8 may be used to implement one or more modules. In some instances, a module may be implemented using both dedicated circuitry and programmable circuitry. For example, a collection module may be implemented using dedicated circuitry that preprocesses signals obtained with a sensor (e.g., circuitry belonging to a device of the user) and in addition the collection module may be implemented with a general purpose processor that organizes and coalesces data received from multiple users.

It will be appreciated that the decision to implement a module in dedicated permanently configured circuitry and/or in temporarily configured circuitry (e.g., configured by software) may be driven by various considerations such as considerations of cost, time, and ease of manufacturing and/or distribution. In any case, the term "module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which modules are temporarily configured (e.g., programmed), not every module has to be configured or instantiated at every point in time. For example, a general-purpose processor may be configured to run different modules at different times.

In some embodiments, a processor implements a module by executing instructions that implement at least some of the functionality of the module. Optionally, a memory may store the instructions (e.g., as computer code), which are read and processed by the processor, causing the processor to perform at least some operations involved in implementing the functionality of the module. Additionally or alternatively, the memory may store data (e.g., measurements of affective response), which is read and processed by the processor in order to implement at least some of the functionality of the module. The memory may include one or more hardware elements that can store information that is accessible to a processor. In some cases, at least some of the memory may be considered part of the processor or on the same chip as the processor, while in other cases, the memory may be considered a separate physical element than the processor. Referring to FIG. 8 for example, one or more processors 401, may execute instructions stored in memory 402 (that may include one or more memory devices), which perform operations involved in implementing the functionality of a certain module.

The one or more processors may also operate to support performance of the relevant operations in a "cloud computing" environment or as a "software as a service" (SaaS). For example, at least some of the operations involved in implementing a module, may be performed by a group of computers accessible via a network (e.g., the Internet) and/or via one or more appropriate interfaces (e.g., application program interfaces (APIs)). Optionally, some of the modules may be executed in a distributed manner among multiple processors. The one or more processors may be located in a single geographic location (e.g., within a home environment, an office environment, or a server farm), and/or distributed across a number of geographic locations. Optionally, some modules may involve execution of instructions on devices that belong to the users and/or are adjacent to the users. For example, procedures that involve data preprocessing and/or presentation of results may run, in part or in full, on processors belonging to devices of the users (e.g., smartphones and/or wearable computers). In this example, preprocessed data may further be uploaded to cloud-based servers for additional processing. Additionally, preprocessing and/or presentation of results for a user may be performed by a software agent that operates on behalf of the user.

In some embodiments, modules may provide information to other modules, and/or receive information from other modules. Accordingly, such modules may be regarded as being communicatively coupled. Where multiple of such modules exist contemporaneously, communications may be achieved through signal transmission (e.g., over appropriate circuits and buses). In embodiments in which modules are configured or instantiated at different times, communications between such modules may be achieved, for example, through the storage and retrieval of information in memory structures to which the multiple modules have access. For example, one module may perform an operation and store the output of that operation in a memory device to which it is communicatively coupled. A different module may then, at a later time, access the memory device to retrieve and process the stored output.

It is to be noted that in the claims, when a dependent system claim is formulated according to a structure similar to the following: "further comprising module X configured to do Y", it is to be interpreted as: "the memory is further configured to store module X, the processor is further configured to execute module X, and module X is configured to do Y".

Modules and other system elements (e.g., databases or models) are typically illustrated in figures in this disclosure as geometric shapes (e.g., rectangles) that may be connected via lines. A line between two shapes typically indicates a relationship between the two elements the shapes represent, such as a communication that involves an exchange of information and/or control signals between the two elements. This does not imply that in every embodiment there is such a relationship between the two elements, rather, it serves to illustrate that in some embodiments such a relationship may exist. Similarly, a directional connection (e.g., an arrow) between two shapes may indicate that, in some embodiments, the relationship between the two elements represented by the shapes is directional, according the direction of the arrow (e.g., one element provides the other with information). However, the use of an arrow does not indicate that the exchange of information between the elements cannot be in the reverse direction too.

The illustrations in this disclosure depict some, but not necessarily all, the connections between modules and/or other system element. Thus, for example, a lack of a line connecting between two elements does not necessarily imply that there is no relationship between the two elements, e.g., involving some form of communication between the two. Additionally, the depiction in an illustration of modules as separate entities is done to emphasize different functionalities of the modules. In some embodiments, modules that are illustrated and/or described as separate entities may in fact be implemented via the same software program, and in other embodiments, a module that is illustrates and/or described as being a single element may in fact be implemented via multiple programs and/or involve multiple hardware elements possibly in different locations.

As used herein, any reference to "one embodiment" or "an embodiment" means that a particular element, feature, structure, or characteristic described in connection with the embodiment is included in at least one embodiment. Moreover, separate references to "one embodiment" or "some embodiments" in this description do not necessarily refer to the same embodiment. Additionally, references to "one embodiment" and "another embodiment" may not necessarily refer to different embodiments, but may be terms used, at times, to illustrate different aspects of an embodiment. Similarly, references to "some embodiments" and "other embodiments" may refer, at times, to the same embodiments.

Herein, a predetermined value, such as a threshold, a predetermined rank, or a predetermined level, is a fixed value and/or a value determined any time before performing a calculation that compares a certain value with the predetermined value. Optionally, a first value may be considered a predetermined value when the logic (e.g., circuitry, computer code, and/or algorithm), used to compare a second value to the first value, is known before the computations used to perform the comparison are started.

Some embodiments may be described using the expression "coupled" and/or "connected", along with their derivatives. For example, some embodiments may be described using the term "coupled" to indicate that two or more elements are in direct physical or electrical contact. The term "coupled," however, may also mean that two or more elements are not in direct contact with each other, but yet still cooperate or interact with each other. The embodiments are not limited in this context.

Some embodiments may be described using the verb "indicating", the adjective "indicative", and/or using variations thereof. For example, a value may be described as being "indicative" of something. When a value is indicative of something, this means that the value directly describes the something and/or is likely to be interpreted as meaning that something (e.g., by a person and/or software that processes the value). Verbs of the form "indicating" or "indicate" may have an active and/or passive meaning, depending on the context. For example, when a module indicates something, that meaning may correspond to providing information by directly stating the something and/or providing information that is likely to be interpreted (e.g., by a human or software) to mean the something. In another example, a value may be referred to as indicating something (e.g., a determination indicates that a risk reaches a threshold), in this case, the verb "indicate" has a passive meaning: examination of the value would lead to the conclusion to which it indicates (e.g., analyzing the determination would lead one to the conclusion that the risk reaches the threshold).

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

In addition, use of the "a" or "an" is employed to describe one or more elements/components/steps/modules/things of the embodiments herein. This description should be read to include one or at least one, and the singular also includes the plural unless it is obvious that it is meant otherwise. Additionally, the phrase "based on" is intended to mean "based, at least in part, on". For example, stating that a score is computed "based on measurements" means that the computation may use, in addition to the measurements, additional data that are not measurements, such as models, billing statements, and/or demographic information of users.

Though this disclosure in divided into sections having various titles, this partitioning is done just for the purpose of assisting the reader and is not meant to be limiting in any way. In particular, embodiments described in this disclosure may include elements, features, components, steps, and/or modules that may appear in various sections of this disclosure that have different titles. Furthermore, section numbering and/or location in the disclosure of subject matter are not to be interpreted as indicating order and/or importance. For example, a method may include steps described in sections having various numbers. These numbers and/or the relative location of the section in the disclosure are not to be interpreted in any way as indicating an order according to which the steps are to be performed when executing the method.

With respect to computer systems described herein, various possibilities may exist regarding how to describe systems implementing a similar functionality as a collection of modules. For example, what is described as a single module in one embodiment may be described in another embodiment utilizing more than one module. Such a decision on separation of a system into modules and/or on the nature of an interaction between modules may be guided by various considerations. One consideration, which may be relevant to some embodiments, involves how to clearly and logically partition a system into several components, each performing a certain functionality. Thus, for example, hardware and/or software elements that are related to a certain functionality may belong to a single module. Another consideration that may be relevant for some embodiments, involves grouping hardware elements and/or software elements that are utilized in a certain location together. For example, elements that operate at the user end may belong to a single module, while other elements that operate on a server side may belong to a different module. Still another consideration, which may be relevant to some embodiments, involves grouping together hardware and/or software elements that operate together at a certain time and/or stage in the lifecycle of data. For example, elements that operate on measurements of affective response may belong to a first module, elements that operate on a product of the measurements may belong to a second module, while elements that are involved in presenting a result based on the product, may belong to a third module.

It is to be noted that essentially the same embodiments may be described in different ways. In one example, a first description of a computer system may include descriptions of modules used to implement it. A second description of essentially the same computer system may include a description of operations that a processor is configured to execute (which implement the functionality of the modules belonging to the first description). The operations recited in the second description may be viewed, in some cases, as corresponding to steps of a method that performs the functionality of the computer system. In another example, a first description of a computer-readable medium may include a description of computer code, which when executed on a processor performs operations corresponding to certain steps of a method. A second description of essentially the same computer-readable medium may include a description of modules that are to be implemented by a computer system having a processor that executes code stored on the computer-implemented medium. The modules described in the second description may be viewed, in some cases, as producing the same functionality as executing the operations corresponding to the certain steps of the method.

While the methods disclosed herein may be described and shown with reference to particular steps performed in a particular order, it is understood that these steps may be combined, sub-divided, and/or reordered to form an equivalent method without departing from the teachings of the embodiments. Accordingly, unless specifically indicated herein, the order and grouping of the steps is not a limitation of the embodiments. Furthermore, methods and mechanisms of the embodiments will sometimes be described in singular form for clarity. However, some embodiments may include multiple iterations of a method or multiple instantiations of a mechanism unless noted otherwise. For example, when a processor is disclosed in one embodiment, the scope of the embodiment is intended to also cover the use of multiple processors. Certain features of the embodiments, which may have been, for clarity, described in the context of separate embodiments, may also be provided in various combinations in a single embodiment. Conversely, various features of the embodiments, which may have been, for brevity, described in the context of a single embodiment, may also be provided separately or in any suitable sub-combination.

Some embodiments described herein may be practiced with various computer system configurations, such as cloud computing, a client-server model, grid computing, peer-to-peer, hand-held devices, multiprocessor systems, microprocessor-based systems, programmable consumer electronics, minicomputers, and/or mainframe computers. Additionally or alternatively, some of the embodiments may be practiced in a distributed computing environment where tasks are performed by remote processing devices that are linked through a communication network. In a distributed computing environment, program components may be located in both local and remote computing and/or storage devices. Additionally or alternatively, some of the embodiments may be practiced in the form of a service, such as infrastructure as a service (IaaS), platform as a service (PaaS), software as a service (SaaS), and/or network as a service (NaaS).

Embodiments described in conjunction with specific examples are presented by way of example, and not limitation. Moreover, it is evident that many alternatives, modifications, and variations will be apparent to those skilled in the art. It is to be understood that other embodiments may be utilized and structural changes may be made without departing from the scope of the appended claims and their equivalents.

What is claimed is:

1. A system configured to notify a user about a cause of emotional imbalance, comprising:
   a sensor configured to take measurements of affective response of the user; and
   a computer configured to:
   receive from the sensor a measurement corresponding to an event, and to make a determination of whether the measurement indicates a state of emotional imbalance of the user;
   receive factors characterizing the event and to select a certain factor that, based on a model of the user, has an effect on the user that is congruous with the measurement of affective response of the user; wherein the model was trained based on data comprising: measurements of affective response of the user corresponding to events involving the user having various experiences, and descriptions of the events; and
   notify the user about the certain factor that characterizes the event, responsive to a determination that the measurement indicates the state of emotional imbalance of the user.

2. The system of claim 1, wherein the measurement comprises at least one of the following values: a physiological signal of the user, a behavioral cue of the user.

3. The system of claim 1, wherein the certain factor represents at least one of the following: interacting with a certain person, partaking in a certain activity, being at a certain location, and a certain situation of the user; and wherein the certain situation is one of the following: being hungry, being tired, being late to an appointment, having insufficient funds, being too cold, and being too warm.

4. The system of claim 1, wherein when the user is in the state of emotional imbalance, the measurement of affective response corresponding to the event indicates that an extent to which the user felt a certain emotion reaches a threshold; and wherein the certain emotion is at least one of the following emotions: anger, contempt, disgust, distress, and fear.

5. The system of claim 1, wherein when the user is in the state of emotional imbalance, the measurement of affective response corresponding to the event indicates that a level of stress felt by the user reaches a threshold.

6. The system of claim 1, wherein the angle between a vector representation of the effect of the certain factor on the user and a vector representation of the measurement of affective response is an acute angle.

7. The system of claim 1, wherein the measurement of affective response is indicative of a certain emotional response and the model indicates that, on average, the effect of the certain factor amounts to an increase in an extent to which the user has the certain emotional response; and wherein the certain emotional response comprises feeling at least one of the following emotions: anger, contempt, disgust, distress, and fear.

8. The system of claim 1, wherein the computer is further configured to receive a prior measurement of affective response of the user taken with the sensor before the event and to utilize the prior measurement to determine whether the measurement corresponding to the event is indicative of the user transitioning to the state of emotional imbalance.

9. The system of claim 1, wherein the computer is further configured to generate a description of the event that comprises the factors characterizing the event; and wherein the event involves the user having an experience, and each of the factors corresponds to at least one of the following: the user, the experience, and the instantiation of the event.

10. The system of claim 9, wherein having the experience involves doing at least one of the following: spending time at a certain location, consuming certain digital content, having a social interaction with a certain entity in the physical world, having a social interaction with a certain entity in a virtual world, viewing a certain live performance, performing a certain exercise, traveling a certain route, and consuming a certain product.

11. The system of claim 1, wherein the model comprises bias values of the user corresponding to factors.

12. The system of claim 1, wherein the model comprises parameters utilized by an Emotional Response Predictor (ERP).

13. A method for notifying a user about a cause of emotional imbalance, comprising:
  taking, utilizing a sensor coupled to a user, a measurement of affective response of the user, which corresponds to an event;
  determining whether the measurement indicates a state of emotional imbalance of the user;
  receiving factors that characterize the event;
  selecting a certain factor that characterizes the event which, based on a model of the user, has an effect on the user that is congruous with the measurement;
  wherein the model was trained based on data comprising: measurements of affective response of the user corresponding to events involving the user having various experiences, and descriptions of the events; and
  responsive to a determination that the measurement indicates the state of emotional imbalance of the user, notifying the user about the certain factor.

14. The method of claim 13, further comprising making the determination that the measurement indicates the state of emotional imbalance of the user based on the measurement of affective response corresponding to the event indicating that an extent to which the user felt a certain emotion reaches a threshold; and wherein the certain emotion is at least one of the following emotions: anger, contempt, disgust, distress, and fear.

15. The method of claim 13, further comprising making the determination that the measurement indicates the state of emotional imbalance of the user based on the measurement of affective response corresponding to the event indicating that a level of stress felt by the user reaches a threshold.

16. The method of claim 13, further comprising receiving a prior measurement of affective response of the user taken with the sensor before the event and utilizing the prior measurement for the determining of whether the measurement corresponding to the event is indicative of the user transitioning to the state of emotional imbalance.

17. The method of claim 13, further comprising generating a description of the event that comprises the factors characterizing the event; wherein the event involves the user having an experience, and each of the factors corresponds to at least one of the following: the user, the experience, and the instantiation of the event.

18. A non-transitory computer-readable medium having instructions stored thereon that, in response to execution by a system including a processor and memory, causes the system to perform operations comprising:
  taking, utilizing a sensor coupled to a user, a measurement of affective response of the user, which corresponds to an event;
  determining whether the measurement indicates a state of emotional imbalance of the user;
  receiving factors that characterize the event;
  selecting a certain factor that characterizes the event which, based on a model of the user, has an effect on the user that is congruous with the measurement;
  wherein the model was trained based on data comprising: measurements of affective response of the user corresponding to events involving the user having various experiences, and descriptions of the events; and
  responsive to a determination that the measurement indicates the state of emotional imbalance of the user, notifying the user about the certain factor.

19. The non-transitory computer-readable medium of claim 18, further comprising instructions defining a step of making the determination that the measurement indicates the state of emotional imbalance of the user based on the measurement of affective response corresponding to the event indicating that an extent to which the user felt a certain emotion reaches a threshold; and wherein the certain emotion is at least one of the following emotions: anger, contempt, disgust, distress, and fear.

20. The method of claim 13, wherein the model comprises bias values of the user corresponding to factors.

21. The method of claim 13, wherein the model comprises parameters utilized by an Emotional Response Predictor (ERP).

* * * * *